US010869924B2

(12) United States Patent
Andrews et al.

(10) Patent No.: US 10,869,924 B2
(45) Date of Patent: Dec. 22, 2020

(54) PD-L1 ANTAGONIST COMBINATION TREATMENTS

(71) Applicants: MERCK PATENT GMBH, Darmstadt (DE); PFIZER INC., New York, NY (US)

(72) Inventors: Glen Ian Andrews, San Diego, CA (US); Shihao Chen, Foster City, CA (US); Alessandra Di Pietro, Opera (IT); David Fontana, Clyde Hill, WA (US); Zelanna Goldberg, San Diego, CA (US); Chia-Yang Lin, Palo Alto, CA (US); Hua Long, San Carlos, CA (US); Marcella Martignoni, Milan (IT); Dimitry Serge Antoine Nuyten, San Francisco, CA (US); Aron David Thall, San Diego, CA (US); Adrian Woolfson, New York, NY (US)

(73) Assignees: MERCK PATENT GMBH, Darmstadt (DE); PFIZER INC., New York, NY (US)

(*) Notice: Subject to any disclaimer, the term of this patent is extended or adjusted under 35 U.S.C. 154(b) by 143 days.

(21) Appl. No.: 15/736,615

(22) PCT Filed: Jun. 15, 2016

(86) PCT No.: PCT/US2016/037498
§ 371 (c)(1),
(2) Date: Dec. 14, 2017

(87) PCT Pub. No.: WO2016/205277
PCT Pub. Date: Dec. 22, 2016

(65) Prior Publication Data
US 2018/0169232 A1 Jun. 21, 2018

Related U.S. Application Data

(60) Provisional application No. 62/180,543, filed on Jun. 16, 2015, provisional application No. 62/219,995, filed on Sep. 17, 2015, provisional application No. 62/286,501, filed on Jan. 25, 2016, provisional application No. 62/337,489, filed on May 17, 2016.

(51) Int. Cl.
| *A61K 39/00* | (2006.01) |
| *A61K 39/395* | (2006.01) |
| *A61K 31/4439* | (2006.01) |
| *C07K 16/24* | (2006.01) |
| *C07K 16/28* | (2006.01) |
| *A61K 45/06* | (2006.01) |
| *A61P 35/00* | (2006.01) |
| *A61K 31/4184* | (2006.01) |
| *A61K 31/706* | (2006.01) |
| *A61K 33/24* | (2019.01) |

(52) U.S. Cl.
CPC ...... *A61K 39/3955* (2013.01); *A61K 31/4184* (2013.01); *A61K 31/4439* (2013.01); *A61K 31/706* (2013.01); *A61K 33/24* (2013.01); *A61K 39/39558* (2013.01); *A61K 45/06* (2013.01); *A61P 35/00* (2018.01); *C07K 16/243* (2013.01); *C07K 16/2827* (2013.01); *C07K 16/2878* (2013.01); *C07K 16/2887* (2013.01); *A61K 2039/505* (2013.01); *A61K 2039/507* (2013.01); *C07K 2317/21* (2013.01); *C07K 2317/76* (2013.01)

(58) Field of Classification Search
CPC .............................. A61P 35/00; A61K 39/00
USPC ...................................................... 424/133.1
See application file for complete search history.

(56) References Cited

U.S. PATENT DOCUMENTS

| 4,816,567 | A | 3/1989 | Cabilly |
| 5,545,806 | A | 8/1996 | Lonberg |
| 5,545,807 | A | 8/1996 | Surani |
| 5,569,825 | A | 10/1996 | Lonberg |
| 5,625,126 | A | 4/1997 | Lonberg |
| 5,633,425 | A | 5/1997 | Lonberg |
| 5,641,870 | A | 6/1997 | Rinderknecht |
| 5,661,061 | A | 8/1997 | Usuami |
| 6,075,181 | A | 6/2000 | Kucherlapati |
| 6,150,584 | A | 11/2000 | Kucherlapati |
| 6,534,524 | B1 | 3/2003 | Kania et al. |
| 6,884,890 | B2 | 4/2005 | Kania et al. |
| 6,982,321 | B2 | 1/2006 | Winter |
| 7,087,409 | B2 | 8/2006 | Barbas |
| 7,141,581 | B2 | 11/2006 | Bender |
| 7,232,910 | B2 | 6/2007 | Ewanicki et al. |
| 7,326,414 | B2 | 2/2008 | Bedian et al. |

(Continued)

FOREIGN PATENT DOCUMENTS

| EP | 0404097 | 12/1990 |
| WO | WO1991010741 | 7/1991 |

(Continued)

OTHER PUBLICATIONS

Amin et al (Journal of Clinical Oncology, 2014, 32 (No. 15 suppl): Abstract 5010).*

(Continued)

*Primary Examiner* — Sean E Aeder
(74) *Attorney, Agent, or Firm* — Haley Guiliano LLP; James F. Haley, Jr.; Brian M. Gummow

(57) ABSTRACT

The present disclosure describes combination therapies comprising an antagonist of Programmed Death Ligand 1 receptor (PD-L1) and another therapeutic agent, and the use of the combination therapies for the treatment of cancer.

24 Claims, 3 Drawing Sheets
Specification includes a Sequence Listing.

(56) References Cited

U.S. PATENT DOCUMENTS

| | | |
|---|---|---|
| 7,488,802 B2 | 2/2009 | Collins |
| 7,521,051 B2 | 4/2009 | Collins |
| 7,794,710 B2 | 9/2010 | Chen |
| 7,960,515 B2 | 6/2011 | Min et al. |
| 8,008,449 B2 | 8/2011 | Korman |
| 8,168,757 B2 | 5/2012 | Finnefrock |
| 8,337,850 B2 | 12/2012 | Ahrens et al. |
| 8,354,509 B2 | 1/2013 | Carven |
| 8,383,796 B2 | 2/2013 | Korman et al. |
| 8,552,154 B2 | 10/2013 | Freeman et al. |
| 8,779,108 B2 | 7/2014 | Queva et al. |
| 8,791,140 B2 | 7/2014 | Campeta |
| 8,993,731 B2 | 3/2015 | Tyson |
| 9,045,545 B1 | 6/2015 | Clube |
| 9,073,994 B2 | 7/2015 | Honjo |
| 9,457,019 B2 | 10/2016 | Flynn |
| 9,539,245 B2 | 1/2017 | Peters |
| 9,624,298 B2 | 4/2017 | Nastri |
| 9,682,143 B2 | 6/2017 | Chang |
| 9,683,048 B2 | 6/2017 | Freeman |
| 9,765,147 B2 | 9/2017 | Wong |
| 1,000,475 A1 | 6/2018 | Wang |
| 9,993,551 B2 | 6/2018 | Lebwohl |
| 1,013,829 A1 | 11/2018 | Cogswell |
| 1,032,309 A1 | 6/2019 | Cogswell |
| 1,057,020 A1 | 2/2020 | Martini |
| 2004/0224988 A1 | 11/2004 | Freddo et al. |
| 2006/0091067 A1 | 5/2006 | Fan et al. |
| 2006/0094763 A1 | 5/2006 | Ye et al. |
| 2007/0203196 A1 | 8/2007 | Ewanicki et al. |
| 2008/0274192 A1 | 11/2008 | Friesen et al. |
| 2010/0179329 A1 | 7/2010 | Campeta et al. |
| 2012/0089541 A1 | 4/2012 | Patel |
| 2013/0078240 A1 | 3/2013 | Ahrens et al. |
| 2013/0309250 A1 | 11/2013 | Cogswell |
| 2014/0242071 A1 | 8/2014 | Liu et al. |
| 2014/0248347 A1 | 9/2014 | Morgado |
| 2014/0288125 A1 | 9/2014 | Murray |
| 2014/0341917 A1 | 11/2014 | Nastri |
| 2015/0190506 A1 | 7/2015 | Cheung et al. |
| 2015/0210769 A1 | 7/2015 | Freeman |
| 2015/0273033 A1 | 10/2015 | Bosch |
| 2016/0009805 A1 | 1/2016 | Kowanetz |
| 2016/0083401 A1 | 3/2016 | Fuchss |
| 2016/0108123 A1 | 4/2016 | Freeman |
| 2016/0152715 A1 | 6/2016 | Wong |
| 2016/0159905 A1 | 6/2016 | Abdiche |
| 2017/0008971 A1 | 1/2017 | Dennis |
| 2017/0088626 A1 | 3/2017 | Jure-Kunkel |
| 2017/0158776 A1 | 6/2017 | Feltquate |
| 2017/0166641 A1 | 6/2017 | Martini |
| 2017/0209574 A1 | 7/2017 | Cao |
| 2017/0296659 A1 | 10/2017 | Lebwohl |
| 2017/0298106 A1 | 10/2017 | Roschke |
| 2017/0320930 A1 | 11/2017 | Matzke-Ogi |
| 2018/0162941 A1 | 6/2018 | Thanavala |
| 2018/0186882 A1 | 7/2018 | Freeman |
| 2018/0244781 A1 | 8/2018 | Cuillerot |
| 2018/0282415 A1 | 10/2018 | Lin |
| 2019/0144545 A1 | 5/2019 | Nuyten |
| 2019/0330352 A1 | 10/2019 | Andrews |
| 2020/0048352 A1 | 2/2020 | Zimmerman |

FOREIGN PATENT DOCUMENTS

| | | |
|---|---|---|
| WO | WO1993011161 | 6/1993 |
| WO | WO1996033735 | 10/1996 |
| WO | WO1996034096 | 10/1996 |
| WO | WO1998024893 | 6/1998 |
| WO | WO2004072286 | 8/2001 |
| WO | WO2004004771 | 1/2004 |
| WO | WO2004056875 | 7/2004 |
| WO | 2006/048745 A1 | 5/2006 |
| WO | 2007/005874 A2 | 1/2007 |
| WO | WO2007005874 | 1/2007 |
| WO | WO2008100562 | 8/2008 |
| WO | WO2008156712 | 12/2008 |
| WO | WO2010027827 | 3/2010 |
| WO | 2010/036959 A2 | 4/2010 |
| WO | WO2010036959 | 4/2010 |
| WO | 2010/077634 A1 | 7/2010 |
| WO | WO2010077634 | 7/2010 |
| WO | 2010/089411 A2 | 8/2010 |
| WO | WO2010089411 | 8/2010 |
| WO | WO2011066342 | 6/2011 |
| WO | WO2011068561 | 6/2011 |
| WO | 2013/019906 A1 | 2/2013 |
| WO | 2013/028231 A1 | 2/2013 |
| WO | WO2013019906 | 2/2013 |
| WO | 2013/046133 A1 | 4/2013 |
| WO | 2013/119202 A1 | 8/2013 |
| WO | WO2013164754 | 11/2013 |
| WO | WO2013181452 | 12/2013 |
| WO | 2014/100079 A1 | 6/2014 |
| WO | WO2014100079 | 6/2014 |
| WO | 2014/167088 A1 | 10/2014 |
| WO | WO2014163684 | 10/2014 |
| WO | 2015/061668 A1 | 4/2015 |
| WO | WO2015061668 | 4/2015 |
| WO | WO2015069266 | 5/2015 |
| WO | 2015/095410 A1 | 6/2015 |
| WO | 2015/095423 A2 | 6/2015 |
| WO | WO2015088847 | 6/2015 |
| WO | WO2014151006 | 9/2015 |
| WO | WO2015134605 | 9/2015 |
| WO | WO2016014148 | 1/2016 |
| WO | WO2016032927 | 3/2016 |
| WO | WO2016059602 | 4/2016 |
| WO | 2016/081384 A1 | 5/2016 |
| WO | WO2016089873 | 6/2016 |
| WO | WO2016100882 | 6/2016 |
| WO | WO2016137985 | 9/2016 |
| WO | WO2016205277 | 12/2016 |
| WO | WO2015036499 | 3/2017 |
| WO | WO2017197140 | 11/2017 |

OTHER PUBLICATIONS

Gross-Goupil et al (Clinical Medicine Insights: Oncology, 2013, 7: 269-277).*

Heery et al (Journal of Clinical Oncology, 2014, 32 (No. 15 suppl): Abstract 3064).*

Cohen et al (Journal of Clinical Oncology, 2008, 26(29): 4708-4713).*

International Search Report, dated Sep. 29, 2016, in PCT/US2016/037498.

Ahmadzadeh, et al., Tumor antigen-specific CD8 T cells infiltrating the tumor express high levels of PD-1 and are functionally impaired, Blood, 114(8):1537-44 (2009).

Anonymous, "Avelumab in Metastatic or Locally Advanced Solid Tumors," (JAVELIN Solid Tumor)—Full Text View—ClinicalTrials. gov, Jan. 14, 2013, URL:https://clinicaltrials.gov/ct2/show/NCT01772004?term=Avelumab&cond=HNSCC&rank=5 [retrieved on Jun. 23, 2017] the whole document (11 pages).

Anonymous, "Avelumab in Patients With Previously Treated Advanced Stage Classical Hodgkin's Lymphoma (JAVELIN HODGKINS)—Full Text View—ClinicalTrials.gov", Nov. 9, 2015 (Nov. 9, 2015), XP055384712, Retrieved from the Internet. URL:https://clinicaltrials.gov/ct2/show/NC T02603419?term=Avelumab&draw=1&rank=38 [retrieved on Jun. 23, 2017] the whole document (10 pages).

Anonymous, "Avelumab in Previously Untreated Patients With Epithelial Ovarian Cancer (JAVELIN OVARIAN 100)—Full Text View—ClinicalTrials.gov", Mar. 12, 2016 (Mar. 12, 2016), XP055384715, Retrieved from the Internet: URL:https://clinicaltrials.gov/ct2/show/NC T02718417?term=Avelumab&draw=1&rank=41 [retrieved on Jun. 23, 2017] the whole document (10 pages).

Anonymous: NCT02511184, Clinical Trials.gov, Archive, Sep. 25, 2015 (11 pages).

(56) References Cited

OTHER PUBLICATIONS

Boyerinas, et al., "Antibody-Dependent Cellular Cytotoxicity Activity of a Novel Anti-PD-L1 Antibody Avelumab (MSB0010718C) on Human Tumor Cells," Cancer Immunology Research, 3(10):1148-1157 (2015).
Brahmer et al., "Safety and activity of anti-PD-L1 antibody in patients with advanced cancer", The New England Journal of Medicine, 366:2455-2465 (2012).
Brown, et al., "Targeting DNA Repair in Cancer: Beyond PARP Inhibitors," Cancer Discovery 7(1):20-37 (2017).
Dong, et al., "B7-H1, a third member of the B7 family, co-stimulates T-cell proliferation and interleukin-10 secretion," Nature Medicine, 5(12):1365-9 (1999).
Fellouse, et al., "Synthetic antibodies from a four-amino-acid code: a dominant role for tyrosine in antigen recognition," PNAS, 101(34):12467-72 (2004).
Freeman, et al., "Engagement of the PD-1 immunoinhibitory receptor by a novel B7 family member leads to negative regulation of lymphocyte activation," Journal of Experimental Medicine, 192(7):1027-34 (2000).
Fury, et al., "Clinical Activity And Safety Of Medi4736, An Anti-Pd-L1 Antibody, In Patients With Head And Neck Cancer", Annals of Oncology, 25(Suppl 4)iv340-iv365 (2014).
Gadiot, et al., "Overall survival and PD-L1 expression in metastasized malignant melanoma," Cancer 117(10):2192-201 (2011).
Goytisolo, et al., "The absence of the DNA-dependent protein kinase catalytic subunit in mice results in anaphase bridges and in increased telomeric fusions with normal telomere length and G-strand overhang," Molecular and Cellular Biology, 21(11):3642-51 (2001).
Gulley, et al., "Exposure-response and PD-L1 expression analysis of second-line avelumab in patients with advanced NSCLC: Data from the JAVELIN Solid Tumor trial," Journal Of Clinical Oncology, 35(15 Supp):9086 (2017)(2 pages).
Heery, et al., "Avelumab for metastatic or locally advanced previously treated solid tumours (JAVELIN Solid Tumor): a phase 1a, multicohort, dose-escalation trial" Lancet Oncology, 19(5):587-598 (2017).
Higuchi, et al., "CTLA-4 Blockade Synergizes Therapeutically with PARP Inhibition in BRCA1-Deficient Ovarian Cancer," Cancer Immunology Research, 3(11):1257-68 (2015).
Higuchi, et al., "PARP inhibition synergizes with anti-CTLA-4 immune therapy to promote rejection of peritoneal tumors in mouse models of ovarian cancer," Gynecologic Oncology, 133:115-116 (2014).
Iwai, et al., "Involvement of PD-L1 on tumor cells in the escape from host immune system and tumor immunotherapy by PD-L1 blockade," PNAS, 99(19):12293-7 (2002).
Keir, et al., "PD-1 and its ligands in tolerance and immunity," Annual Review of Immunology, 26:677-704 (2008).
Kelly, et al., "Avelumab (MSB00010718C; anti-PD-L1) in patients with advanced cancer: Safety data from 1300 patients enrolled in the phase 1b JAVELIN Solid Tumor Trial," Journal of Clinical Oncology, 343(15):3055 (4 pages) (2016).
Kohler, et al., "Continuous cultures of fused cells secreting antibody of predefined specificity," Nature, 256(5517):495-7 (1975).
Latchman, et al., "PD-L2 is a second ligand for PD-1 and inhibits T cell activation," Nature Immunology, 2(3):261-8 (2001).
Le, et al., Human antibodies for immunotherapy development generated via a human B cell hybridoma technology, PNAS, 103(10):3557-62 (2006).
Le, et al., "PD-1 Blockade in Tumors with Mismatch-Repair Deficiency," New England Journal of Medicine, 372(26):2509-20 (2015).
Liao et al., "Treating patients with ALK-positive non-small cell lung cancer: latest evidence and management strategy," Therapeutics Advances in Medical Oncology, 7(5):274-290 (2015).
Lutzky et al., "A Phase 1 study of MEDI4736, an anti-PD-L1 antibody, in patients with advanced solid tumors," Journal of Clinical Oncology; 2014 ASCO Annual Meeting, American Society of Clinical Oncology, 32(15 Suppl):3001 (2014) (1 page).
Okazaki, et al., "PD-1 and PD-1 ligands: from discovery to clinical application," International Immunology, 19(7):813-24 (2007).
Pal, et al., "Programmed death-1 inhibition in renal cell carcinoma: clinical insights and future directions," Clinical Advances in hematology and Oncology, 12(2):90-99 (2014).
Passiglia,et al., "PD-L1 expression as predictive biomarker in patients with NSCLC: a pooled analysis," Oncotarget, 7(15): 19738-19747 (2016).
Powles et al., "Inhibition of PD-L1 by MPDL3280A and clinical activity in pts with metastatic urothelial bladder cancer (UBC)," Journal of Clinical Oncology, 2014 ASCO Annual Meeting Abstracts, No. 15 (2014) (1 page).
Segal et al., "Preliminary data from a multi-arm expansion study of MEDI4736, an anti-PD-L1 antibody," Journal of Clinical Oncology, 32(15):Abstract (2014) (1 page).
Shitara, et al., "Phase I, open-label, multi-ascending dose trial of avelumab (MSB0010718C), an anti-PD-L1 monoclonal antibody, in Japanese patients with advanced solid tumors," Journal of Clinical Oncology, 22(15 Supp):3023 (2015) (2 pages).
Smith, et al., "The DNA-dependent protein kinase," Genes and Development, 13(8):916-34 (1999).
Taube, et al., "Colocalization of inflammatory response with B7-hl expression in human melanocytic lesions supports an adaptive resistance mechanism of immune escape," Science Translational Medicine, 4(127):127ra37 (2012).
Thompson, et al., "Costimulatoiy B7-H1 in renal cell carcinoma patients: Indicator of tumor aggressiveness and potential therapeutic target," PNAS 101(49):17174-9 (2004).
Thompson, et al., "Tumor B7-H1 is associated with poor prognosis in renal cell carcinoma patients with long-term follow-up," Cancer Research, 66(7):3381-5 (2006).
Toplian, et al., "Safety, activity, and immune correlates of anti-PD-1 antibody in cancer," New England Journal of Medicine, 366 (26):2443 (2012).
Williams et al., "Telomere dysfunction and DNA-PKcs deficiency: characterization and consequence," Cancer Research, 69(5):2100-7 (2009).
Powles et al., "MPDL3280A (anti-PD-L1) Treatment Leads to Clinical Activity in Metastatic Bladder Cancer," Nature, 515(7528):558-562 (2014).
Tanaka et al., "Anti-PD-1 Antibody: Basics and Clinical Application," Japanese Journal of Cancer and Chemotherapy, 40(9):1145-1149 (2013).
Atkins et al., "Axitinib in Combination with Pembrolizumab in Patients with Advanced Renal Cell Carcinoma," presented at the European Society of Medical Oncology (ESM), Oct. 7-11, 2016, Copenhagen Denmark (1 page).
Atkins, et al., "Axitinib in Combination with Pembrolizumab in Patients with Advanced Renal Cell Cancer: a Non-Randomised, Open-Label, Dose-Finding, and Dose-Expansion Phase 1b Trial," The Lancet Oncology, 19(3):405-415 (2018).
Bai, et al., "A Guide to Rational Dosing of Monoclonal Antibodies," Clinical Pharmacokinetics, 51(2):119-135 (2012).
Bailey, et al., "Immune Checkpoint Inhibitors as Novel Targets for Renal Cell Carcinoma Therapeutics," The Cancer Journal, 19(4):348-352 (2013).
Choueiri, et al., "Trial in Progress: Phase 1b Dose-Finding Study of Axitinib Plus Pembrolizumab for First-Line Treatment of Advanced Renal Cell Carcinoma (RCC)," BJU International, 114(Supp. 4):4-5 (2014).
Clinical Trials NCT01472081, "Nivolumab (BMS-936558; MDX-1106) in Combination with Sunitinib, Pazopanib, or Ipilimumab in Subjects with Metastatic Renal Cell Carcinoma (RCC) (CheckMate 016)" (12 pages) (Study record version available online at clinicaltrials(dot)govict2/history/NCTO 1472081, submitted Jun. 12, 2019).
Clinical Trials NCT01472081, "Nivolumab (BMS-936558; MDX-1106) in Combination with Sunitinib, Pazopanib, or Ipilimumab in Subjects with Metastatic Renal Cell Carcinoma (RCC) (CheckMate 016)" (5 pages) (Study record version available online at clinicaltrials(dot)govict2/history/NCTO 1472081, submitted Jun. 12, 2019).

(56) References Cited

OTHER PUBLICATIONS

Clinical Trials NCT01984242, "A Study of Atezolizumab (an Engineered Anti-Programmed Death-Ligand 1 [PD-L1] Antibody) as Monotherapy or in Combination with Bevacizumab (Avastin® ) Compared to Sunitinib (Sutent® ) in Participants with Untreated Advanced Renal Cell Carcinoma (IMmotion150)" (5 pages) (Study record version available online at clinicaltrials(dot)govict2/history/NCT019 84242, submitted Jun. 12, 2019).

Clinical Trials NCT02036502, "A study of Pembrolizumab (MK-3475) in Combination with Standard of Care Treatments in Participants with Multiple Myeloma (MK-3475-023/KEYNOTE-023)" (11 pages) (Study record version available online at ClinicalTrials(dot)gov archive, submitted Apr. 24, 2018).

Clinical Trials NCT02036502, "A study of Pembrolizumab (MK-3475) in Combination with Standard of Care Treatments in Participants with Multiple Myeloma (MK-3475-023/KEYNOTE-023)" (5 pages) (Study record version available online at clinicaltrials(dot)gov/ct2/history/NCT02036502, submitted Apr. 24, 2018).

Clinical Trials NCT02039674, "A Study of Pembrolizumab (MK-3475) in Combination with Chemotherapy or Immunotherapy in Participants with Non-Small Cell Lung Cancer (MK-3475-021/KEYNOTE-021)" (5 pages) (Study record version available online at clinicaltrials(dot)govict2/history/NCT02039674, submitted Jun. 12, 2019).

Clinical Trials NCT02039674, "A Study of Pembrolizumab (MK-3475) in Combination with Chemotherapy or Immunotherapy in Participants with Non-Small Cell Lung Cancer (MK-3475-021/KEYNOTE-021)," (6 pages) (Study record version available online at clinicaltrials(dot)govict2/history/NCT02039674, submitted Jan. 11, 2019).

Clinical Trials NCT02133742, "A Dose Finding Study to Evaluate Safety, Drug Interaction, Tumor Markers of Axitinib in Combination with MK-3475 in Adult Patients with Previously Untreated Advanced Renal Cell Cancer" (1 page) (Study record version available online at clinicaltrials(dot)govict2/history/NCT02133742, submitted Jun. 20, 2019).

Clinical Trials NCT02133742, "A Dose Finding Study to Evaluate Safety, Drug Interaction, Tumor Markers of Axitinib in Combination with MK-3475 in Adult Patients with Previously Untreated Advanced Renal Cell Cancer" (8 pages) (Study record version available online at clinicaltrials(dot)govict2/history/NCT02133742, submitted Jun. 20, 2019).

Clinical Trials NCT02331368, "Phase 2 Multi-Center Study of Anti-PD-1 during Lymphopenic State after HDT/ASCT for Multiple Myeloma" (4 pages) (Study record version available online at clinicaltrials(dot)govict2/history/NCT02331368, submitted Jul. 2, 2018).

Clinical Trials NTC02014636, "Safety and Efficacy Study of Pazopanib and MK 3475 in Advanced Renal Cell Carcinoma (RCC; KEYNOTE-018)" (6 pages) (Study record version available online at https:clinicaltrials(dot)gov/ct2/histoiy/NCT02014636, submitted Apr. 26, 2019).

Clinical Trials: NCT02014636, "A Phase I/II Study to Assess the Safety and Efficacy of Pazopanib and MK 34 75 in Subjects With Advanced Renal Cell Carcinoma," Clinical Trials.gov (Jan. 24, 2014), pp. 1-11. Retrieved from the Internet URL: https//clinicaltrials.gov/archive/NCT02014636/2014 01 24 [retrieved on Mar. 31, 2015] (11 pages).

Clinical Trials: NCT02133742, "A Phase 1 B, Open Label, Dose Finding Study to Evaluate Safety, Pharmacokinetics And Pharmacodynamics Of Axitinib (AG-013736) In Combination With MK-34 75 In Patients With Advanced Renal Cell Cancer," ClinicalTrials.gov archive, (May 7, 2014), Retrieved from the Internet: URL:httpsjjclinicaltrials.govjarchive/NCT02133742/2014 05 07 [retrieved on Mar. 30, 2015] (3 pages).

Clinical Trials: NCT02179918, "A Phase 1 Study of the 4-1B Agonist PF-05082566 in Combination with the PD-1 Inhibitor MK-3475 in Patients with Advanced Solidy Tumors," Clinical Trials.gov (Jul. 1, 2014), pp. 1-6. Retrieved from the Internet URL: https://clinicaltrials.gov/archive/NCT02179918/2014 07 01 (6 pages).

Czarnecka, et al., "The Activity of Tyrosine Kinase Inhibitors on Clear Cell Renal Cell Carcinoma Tumor Initiating Cells in Hypoxic Microenvironment," BJUI Supplements, The 11th International Kidney Cancer Symposium Annual Meeting Proceedings, 110(Suppl. 2):1-20 (2012).

Domblides, et al., "Emerging Antiangiogenics for Renal Cancer," Expert Opinion on Emerging Drugs, 18(4):495-511 (2013) (published online Dec. 2, 2013).

Dong et al., "Tumor-associated B7-H1 promotes T-cell apoptosis: a potential mechanism of immune evasion," Nature Medicine, 8(8):793-800 (2002).

Dorff, et al., "Novel Tyrosine Kinase Inhibitors for Renal Cell Carcinoma," Expert Review of Clinical Pharmacology, 7(1):67-73 (2014).

Duraiswamy, et al., "Therapeutic PD-1 pathway blockade augments with other modalities of immunotherapy T-cell function to prevent immune decline in ovarian cancer," Cancer Research, 73(23):6900-6912 (2013).

Escudier, et al., "Axitinib for the management of metastatic renal cell carcinoma," Drugs in R&D 11(2):113-126 (2011).

Escudier, et al., "Optimal Management of Metastatic Renal Cell Carcinoma: Current Status," Drugs, 73:427-438 (2013).

European Search Report in European Application No. 18205542, dated Mar. 21, 2019 (8 pages).

FDA-Approved Patient Labeling for INLYTA, referenceID:3078397 (Jan. 2012) (22 pages).

Gao et al., "Overexpression of PD-L1 significantly associates with tumor aggressiveness and postoperative recurrence in human hepatocellular carcinoma," Clinical Cancer Research, 15(3):971-979 (2009).

Ghebeh et al., "FOXP3+ Tregs and B7-H1+/PD-1+ T lymphocytes co-infiltrate the tumor tissues of high-risk breast cancer patients: Implication for immunotherapy," BMC Cancer, 8:57 (12 pages) (2008).

Ghebeh et al., "The B7-H1 (PD-L1) T lymphocyte-inhibitory molecule is expressed in breast cancer patients with infiltrating ductal carcinoma: correlation with important high-risk prognostic factors," Neoplasia, 8(3):190-198 (2006).

Hamanishi et al., "Programmed cell death 1 ligand 1 and tumor-infiltrating CD8+ T lymphocytes are prognostic factors of human ovarian cancer," Proceeding of the National Academy of Sciences, 104(9):3360-3365 (2007).

Hamid et al., "Safety and tumor responses with lambrolizumab (anti-PD-1) in melanoma," New England Journal of Medicine, 369(2):134-144 (2013).

Hino et al., "Tumor cell expression of programmed cell death-1 ligand 1 is a prognostic factor for malignant melanoma," Cancer, 116(7):1757-1766 (2010).

Hu-Lowe et al., "Nonclinical antiangiogenesis and antitumor activities of axitinib (AG-013736), an oral, potent, and selective inhibitor of vascular endothelial cell growth factor receptor tyrosine kinases 1, 2, 3," Clinical Cancer Research, 14(22): 7272-7283 (2008).

Inman et al., "PD-L1 (B7-H1) expression by urothelial carcinoma of the bladder and BCG-induced granulomata: associates with localized stage progression," Cancer, 109(8):1499-1505 (2007).

Joshi, "ASCO GU 2018: Safety and Efficacy of Axitinib in Combination with Pembrolizumab in Patients with Advanced Renal Cell Cancer" available at www.urotoday.com (downloaded Oct. 19, 2018) (2 pages).

Kaufman, et al., "The Society for Immunotherapy of Cancer Consensus Statement on Tumour Immunotherapy for the Treatment of Cutaneous Melanoma," Nature, 10:588-598 (2013).

Lipson, et al., "Durable Cancer Regression Off-Treatment and Effective Reinduction Therapy with an Anti-PD-1 Antibody," Clinical Cancer Research, 19:462-468 (2013).

Massari, et al., "PD-1 Blockade Therapy in Renal Cell Carcinoma: Current Studies and Future Promises," Cancer Treatment Reviews, 41:114-121 (2015).

McDermott et al., "PD-1 as a potential target in cancer therapy," Cancer Medicine, 2(5):662-673 (2013).

Nakanishi et al., "Overexpression of B7-H1 (PD-L1) significantly associates with tumor grade and postoperative prognosis in human urothelial cancers," Cancer Immunology, 56(8):1173-1182 (2007).

(56) References Cited

OTHER PUBLICATIONS

Nomi et al., "Clinical significance and therapeutic potential of the programmed death-1 ligand/programmed death-1 pathway in human pancreatic cancer," Clinical Cancer Research, 13(7):2151-2157 (2007).
Ohigashi et al., "Clinical significance of programmed death-1 ligand-1 and programmed death-1 ligand-2 expression in human esophageal cancer," Clinical Cancer Research, 11(8):2947-2953 (2005).
Pal, et al., "Novel Therapies for Metastatic Renal Cell Carcinoma: Efforts to Expand beyond the VEGF/mTOR Signaling Paradigm," Molecular Cancer Therapeutics, 11(3):526-537 (2012).
Pardoll, "The Blockade of Immune Checkpoints in Cancer Immunotherapy," Nature, 12:252-264 (2016).
Patel, et al., "Clinical Cancer Advances 2013: Annual Report on Progress Against Cancer from the American Society of Clinical Oncology," Journal of Clinical Oncology, 32(2):129-160 (2014) (published online Dec. 10, 2013).
Patnaik et al., "Phase I Study of MK-3475 (Anti-PD-1 Monoclonal Antibody) in Patients with Advanced Solid Tumors," J. Clin. Oncol., 30(Supp.15):2512 (2012) (2 pages).
Patnaik et al., "Phase I Study of Pembrolizumab (MK-3475; Anti-PD-1 Monoclonal Antibody) in Patients with Advanced Solid Tumors," Clinical Cancer Research; 21(19) (2015) (9 pages).
PCT International Search Report, International Application No. PCT/US2015/014212, dated Apr. 10, 2015 (12 pages).
Procopio, et al., "Combination Therapies for Patients with Metastatic Renal Cell Carcinoma," Lancet, 19:281-283 (2018).
Rini, et al., "Five-Year Survival in Patients with Cytokine-Refractory Metastatic Renal Cell Carcinoma Treated with Axitinib," Clinical Genitourinary Cancer, 11(2):107-114 (2013).
Rini, et al., "Pembrolizumab Plus Axitinib Versus Sunitinib for Advanced Renal-Cell Carcinoma," The New England Journal of Medicine, 380:1116-1127 (2019).
Robert, et al., "Drug of the Year: Programmed Death-1 Receptor/Programmed Death-1 Ligand-1 Receptor Monoclonal Antibodies," European Journal of Cancer, 49:2968-2971 (2013).
Robert, et al., "LBA34-Pembrolizumab (Pembro:MK-3475) for Advanced Melanoma (MEL): Randomized Comparison of Two Dosing Schedules," Annals of Oncology, 25(Suppl.4):1-41 (Sep. 2014).
Rothermundt, et al., "Successful treatment with an anti-PD-1 antibody for progressing brain metastases in renal cell cancer," Annals of Oncology, 25:544-552 (2016).
Seliger, et al., "Abstracts from the 25th Annual Scientific Meeting of the International Society for Biological Therapy of Cancer (now the Society of Immunotherapy of Cancer)", Journal of Immunotherapy, 34(2):221-227 (2011).
Sequence Listing from International Application No. PCT/US2008/007463, filed Jun. 13, 2008 (24 pages).

Sharpe, et al., "The function of programmed cell death 1 and its ligands in regulating autoimmunity and infection," Nature Immunology, 8(3):239-245 (2007).
Shimauchi, et al., "Augmented expression of programmed death-1 in both neoplastic and non-neoplastic CD4+ T-cells in adult T-cell leukemia/lymphoma," International Journal of Cancer, 121(12):2585-2590 (2007).
Sliwkowski, et al., "Antibody Therapeutics in Cancer," Science, 341:1192-1198 (2013).
Solowiej, et al., "Characterizing the effects of the juxtamembrane domain on vascular endothelial growth factor receptor-2 enzymatic activity, autophosphorylation, and inhibition by axitinib," Biochemistry, 48(29):7019-31 (2009).
Stehle, et al., "Reduced Immunosuppressive Properties of Axitinib in Comparison with Other Tyrosine Kinase Inhibitors," J. Biol. Chem., 288(23):16334-16347 (2013).
Sznol, et al., "Phase 1b evaluation of MPDL3280A (anti-PDFL1) in connection with bevacizumab (bev) in patients (pts) with metastatic renal cell carcinoma (mRCC)," Journal of Clinical Oncology, 33(7):Abstract (2015) (3 pages).
Taiwan Search Report for Application No. CN104103603, dated Sep. 11, 2018 (14 pages).
Tang, et al., "Programmed Death 1 Pathway Inhibition in Metastatic Renal Cell Cancer and Prostate Cancer," Current Oncology Reports, 15:98-104 (2013).
Thompson, et al., "PD-1 is expressed by tumor-infiltrating immune cells and is associated with poor outcome for patients with renal cell carcinoma," Clinical Cancer Research, 13(6):1757 1761 (2007).
Thompson, et al., "Significance of B7-H1 overexpression in kidney cancer," Clinical Genitourin Cancer, 5(3):206-211 (2006).
Tykodi, "Progress and Potential of Immune Checkpoint Blockage for Treating Advanced Renal Cell Carcinoma," Immunotherapy, 5(6):607-619 (2013).
Van Geel, et al.," Concise Drug Review: Pazopanib and Axitinib," The Oncologist, 17:1081-1089 (2012).
Wei, et al., "Combinatorial PD-1 blockade and CD137 activation has therapeutic efficacy in murine cancer models and synergizes with cisplatin," PLOS One, 8(12):e84927 (11 pages) (2013).
WHO Drug Information, vol. 27, No. 2, pp. 161-162 (2013).
Yang, et al., "PD-L1: PD-1 interaction contributes to the functional suppression of T-cell responses to human uveal melanoma cells in vitro," Investigative Ophthalmology & Visual Science, 49(6):2518-2525 (2008).
Yasuda et al., "Simultaneous blockade of programmed death 1 and vascular endothelial growth factor receptor 2 (VEGFR2) induces synergistic anti-tumour effect in vivo," Clinical and Experimental Immunology, 172(3):500-506 (2013).
Yousaf, et al., "Axitinib in advanced renal-cell carcinoma," The Lancet Oncology, 12(13):1245-1246 (2013).

* cited by examiner

SEQUENCE LISTING

```
<160> NUMBER OF SEQ ID NOS: 41

<210> SEQ ID NO 1
<211> LENGTH: 290
<212> TYPE: PRT
<213> ORGANISM: homo sapiens

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190
```

```
Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
                275                 280                 285

Glu Thr
    290

<210> SEQ ID NO 2
<211> LENGTH: 5
<212> TYPE: PRT
<213> ORGANISM: homo sapiens

<400> SEQUENCE: 2

Ser Tyr Ile Met Met
1               5

<210> SEQ ID NO 3
<211> LENGTH: 11
<212> TYPE: PRT
<213> ORGANISM: homo sapiens

<400> SEQUENCE: 3

Ser Ile Tyr Pro Ser Gly Gly Ile Thr Phe Tyr
1               5                   10

<210> SEQ ID NO 4
<211> LENGTH: 11
<212> TYPE: PRT
<213> ORGANISM: homo sapiens

<400> SEQUENCE: 4

Ile Lys Leu Gly Thr Val Thr Thr Val Asp Tyr
1               5                   10

<210> SEQ ID NO 5
<211> LENGTH: 14
<212> TYPE: PRT
<213> ORGANISM: homo sapiens

<400> SEQUENCE: 5

Thr Gly Thr Ser Ser Asp Val Gly Gly Tyr Asn Tyr Val Ser
1               5                   10

<210> SEQ ID NO 6
<211> LENGTH: 7
<212> TYPE: PRT
<213> ORGANISM: homo sapiens

<400> SEQUENCE: 6

Asp Val Ser Asn Arg Pro Ser
1               5

<210> SEQ ID NO 7
<211> LENGTH: 10
```

```
<212> TYPE: PRT
<213> ORGANISM: homo sapiens

<400> SEQUENCE: 7

Ser Ser Tyr Thr Ser Ser Ser Thr Arg Val
1               5                   10

<210> SEQ ID NO 8
<211> LENGTH: 118
<212> TYPE: PRT
<213> ORGANISM: homo sapiens

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Ile Lys Leu Gly Thr Val Thr Val Asp Tyr Trp Gly Gln Gly Thr
            100                 105                 110

Leu Val Thr Val Ser Ser
            115

<210> SEQ ID NO 9
<211> LENGTH: 110
<212> TYPE: PRT
<213> ORGANISM: Homo sapiens

<400> SEQUENCE: 9

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110

<210> SEQ ID NO 10
<211> LENGTH: 450
<212> TYPE: PRT
<213> ORGANISM: Homo sapiens

<400> SEQUENCE: 10

Glu Val Gln Leu Leu Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Ser Ser Tyr
         20                  25                  30
Ile Met Met Trp Val Arg Gln Ala Pro Gly Lys Gly Leu Glu Trp Val
             35                  40                  45
Ser Ser Ile Tyr Pro Ser Gly Gly Ile Thr Phe Tyr Ala Asp Thr Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Ile Lys Leu Gly Thr Val Thr Val Asp Tyr Trp Gly Gln
             100                 105                 110
Gly Thr Leu Val Thr Val Ser Ser Ala Ser Thr Lys Gly Pro Ser Val
             115                 120                 125
Phe Pro Leu Ala Pro Ser Ser Lys Ser Thr Ser Gly Gly Thr Ala Ala
 130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                 165                 170                 175
Leu Gln Ser Ser Gly Leu Tyr Ser Leu Ser Ser Val Val Thr Val Pro
             180                 185                 190
Ser Ser Ser Leu Gly Thr Gln Thr Tyr Ile Cys Asn Val Asn His Lys
             195                 200                 205
Pro Ser Asn Thr Lys Val Asp Lys Lys Val Glu Pro Lys Ser Cys Asp
 210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                 245                 250                 255
Ser Arg Thr Pro Glu Val Thr Cys Val Val Val Asp Val Ser His Glu
             260                 265                 270
Asp Pro Glu Val Lys Phe Asn Trp Tyr Val Asp Gly Val Glu Val His
             275                 280                 285
Asn Ala Lys Thr Lys Pro Arg Glu Glu Gln Tyr Asn Ser Thr Tyr Arg
 290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                 325                 330                 335
Lys Thr Ile Ser Lys Ala Lys Gly Gln Pro Arg Glu Pro Gln Val Tyr
             340                 345                 350
Thr Leu Pro Pro Ser Arg Asp Glu Leu Thr Lys Asn Gln Val Ser Leu
             355                 360                 365
Thr Cys Leu Val Lys Gly Phe Tyr Pro Ser Asp Ile Ala Val Glu Trp
 370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                 405                 410                 415
Lys Ser Arg Trp Gln Gln Gly Asn Val Phe Ser Cys Ser Val Met His
             420                 425                 430
```

Glu Ala Leu His Asn His Tyr Thr Gln Lys Ser Leu Ser Leu Ser Pro
                435                 440                 445

Gly Lys
    450

<210> SEQ ID NO 11
<211> LENGTH: 216
<212> TYPE: PRT
<213> ORGANISM: Homo sapiens

<400> SEQUENCE: 11

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 12
<211> LENGTH: 6
<212> TYPE: PRT
<213> ORGANISM: Artificial Sequence
<220> FEATURE:
<223> OTHER INFORMATION: Humanized antibody sequence

<400> SEQUENCE: 12

Ser Thr Tyr Trp Ile Ser
1               5

<210> SEQ ID NO 13
<211> LENGTH: 17
<212> TYPE: PRT
<213> ORGANISM: Artificial Sequence
<220> FEATURE:
<223> OTHER INFORMATION: Humanized antibody sequence

<400> SEQUENCE: 13

-continued

```
Lys Ile Tyr Pro Gly Asp Ser Tyr Thr Asn Tyr Ser Pro Ser Phe Gln
1               5                   10                  15

Gly
```

<210> SEQ ID NO 14
<211> LENGTH: 8
<212> TYPE: PRT
<213> ORGANISM: Artificial Sequence
<220> FEATURE:
<223> OTHER INFORMATION: Humanized antibody sequence

<400> SEQUENCE: 14

```
Arg Gly Tyr Gly Ile Phe Asp Tyr
1               5
```

<210> SEQ ID NO 15
<211> LENGTH: 11
<212> TYPE: PRT
<213> ORGANISM: Artificial Sequence
<220> FEATURE:
<223> OTHER INFORMATION: Humanized antibody sequence

<400> SEQUENCE: 15

```
Ser Gly Asp Asn Ile Gly Asp Gln Tyr Ala His
1               5                   10
```

<210> SEQ ID NO 16
<211> LENGTH: 7
<212> TYPE: PRT
<213> ORGANISM: Artificial Sequence
<220> FEATURE:
<223> OTHER INFORMATION: Humanized antibody sequence

<400> SEQUENCE: 16

```
Gln Asp Lys Asn Arg Pro Ser
1               5
```

<210> SEQ ID NO 17
<211> LENGTH: 11
<212> TYPE: PRT
<213> ORGANISM: Artificial Sequence
<220> FEATURE:
<223> OTHER INFORMATION: Humanized antibody sequence

<400> SEQUENCE: 17

```
Ala Thr Tyr Thr Gly Phe Gly Ser Leu Ala Val
1               5                   10
```

<210> SEQ ID NO 18
<211> LENGTH: 116
<212> TYPE: PRT
<213> ORGANISM: Artificial Sequence
<220> FEATURE:
<223> OTHER INFORMATION: Humanized antibody sequence

<400> SEQUENCE: 18

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60
```

```
Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Tyr Gly Ile Phe Asp Tyr Trp Gly Gln Gly Thr Leu Val
            100                 105                 110

Thr Val Ser Ser
        115

<210> SEQ ID NO 19
<211> LENGTH: 108
<212> TYPE: PRT
<213> ORGANISM: Artificial Sequence
<220> FEATURE:
<223> OTHER INFORMATION: Humanized antibody sequence

<400> SEQUENCE: 19

Ser Tyr Glu Leu Thr Gln Pro Pro Ser Val Ser Val Ser Pro Gly Gln
 1               5                  10                  15

Thr Ala Ser Ile Thr Cys Ser Gly Asp Asn Ile Gly Asp Gln Tyr Ala
                20                  25                  30

His Trp Tyr Gln Gln Lys Pro Gly Gln Ser Pro Val Leu Val Ile Tyr
            35                  40                  45

Gln Asp Lys Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Ala Thr Tyr Thr Gly Phe Gly Ser Leu
                 85                  90                  95

Ala Val Phe Gly Gly Gly Thr Lys Leu Thr Val Leu
            100                 105

<210> SEQ ID NO 20
<211> LENGTH: 442
<212> TYPE: PRT
<213> ORGANISM: Artificial Sequence
<220> FEATURE:
<223> OTHER INFORMATION: Humanized antibody sequence

<400> SEQUENCE: 20

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Ser Phe Ser Thr Tyr
                20                  25                  30

Trp Ile Ser Trp Val Arg Gln Met Pro Gly Lys Gly Leu Glu Trp Met
            35                  40                  45

Gly Lys Ile Tyr Pro Gly Asp Ser Tyr Thr Asn Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Tyr Gly Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140
```

-continued

```
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Asn Phe
        180                 185                 190

Gly Thr Gln Thr Tyr Thr Cys Asn Val Asp His Lys Pro Ser Asn Thr
    195                 200                 205

Lys Val Asp Lys Thr Val Glu Arg Lys Cys Cys Val Glu Cys Pro Pro
210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser His Glu Asp Pro Glu Val Gln Phe Asn Trp
        260                 265                 270

Tyr Val Asp Gly Val Glu Val His Asn Ala Lys Thr Lys Pro Arg Glu
    275                 280                 285

Glu Gln Phe Asn Ser Thr Phe Arg Val Val Ser Val Leu Thr Val Val
290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
            325                 330                 335

Gln Pro Arg Glu Pro Gln Val Tyr Thr Leu Pro Pro Ser Arg Glu Glu
        340                 345                 350

Met Thr Lys Asn Gln Val Ser Leu Thr Cys Leu Val Lys Gly Phe Tyr
    355                 360                 365

Pro Ser Asp Ile Ala Val Glu Trp Glu Ser Asn Gly Gln Pro Glu Asn
370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
            405                 410                 415

Val Phe Ser Cys Ser Val Met His Glu Ala Leu His Asn His Tyr Thr
        420                 425                 430

Gln Lys Ser Leu Ser Leu Ser Pro Gly Lys
    435                 440
```

<210> SEQ ID NO 21
<211> LENGTH: 214
<212> TYPE: PRT
<213> ORGANISM: Artificial Sequence
<220> FEATURE:
<223> OTHER INFORMATION: Humanized antibody sequence

<400> SEQUENCE: 21

```
Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60
```

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 22
<211> LENGTH: 466
<212> TYPE: PRT
<213> ORGANISM: Homo sapiens

<400> SEQUENCE: 22

Met Glu Leu Gly Leu Cys Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Phe Ser Met Thr Trp Val Arg Gln Ala Pro Gly Lys Gly Leu
    50                  55                  60

Glu Trp Val Ser Tyr Ile Ser Ser Arg Ser Thr Ile Ser Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Asp Glu Asp Thr Ala Val
            100                 105                 110

Tyr Tyr Cys Ala Arg Asp Pro Leu Leu Ala Gly Ala Thr Phe Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
            275                 280                 285

Asp Pro Glu Val Gln Phe Asn Trp Tyr Val Asp Gly Val Glu Val His
        290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 23
<211> LENGTH: 235
<212> TYPE: PRT
<213> ORGANISM: Homo sapiens

<400> SEQUENCE: 23

Met Glu Thr Pro Ala Gln Leu Leu Phe Leu Leu Leu Leu Trp Leu Pro
1               5                   10                  15

Asp Thr Thr Gly Glu Phe Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

```
Gly Ser Ser Pro Leu Thr Phe Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 24
<211> LENGTH: 5
<212> TYPE: PRT
<213> ORGANISM: Homo sapiens

<400> SEQUENCE: 24

Ser Phe Ser Met Thr
1               5

<210> SEQ ID NO 25
<211> LENGTH: 17
<212> TYPE: PRT
<213> ORGANISM: Homo sapiens

<400> SEQUENCE: 25

Tyr Ile Ser Ser Arg Ser Ser Thr Ile Ser Tyr Ala Asp Ser Val Lys
1               5                   10                  15

Gly

<210> SEQ ID NO 26
<211> LENGTH: 12
<212> TYPE: PRT
<213> ORGANISM: Homo sapiens

<400> SEQUENCE: 26

Asp Pro Leu Leu Ala Gly Ala Thr Phe Phe Asp Tyr
1               5                   10

<210> SEQ ID NO 27
<211> LENGTH: 12
<212> TYPE: PRT
<213> ORGANISM: Homo sapiens

<400> SEQUENCE: 27

Arg Ala Ser Gln Ser Val Ser Ser Ser Tyr Leu Ala
1               5                   10

<210> SEQ ID NO 28
<211> LENGTH: 7
<212> TYPE: PRT
<213> ORGANISM: Artificial Sequence
<220> FEATURE:
<223> OTHER INFORMATION: MCSF antibody CDRL2 sequence

<400> SEQUENCE: 28
```

```
Gly Ala Ser Ser Arg Ala Thr
1               5

<210> SEQ ID NO 29
<211> LENGTH: 9
<212> TYPE: PRT
<213> ORGANISM: Homo sapiens

<400> SEQUENCE: 29

Gln Gln Tyr Gly Ser Ser Pro Leu Thr
1               5

<210> SEQ ID NO 30
<211> LENGTH: 141
<212> TYPE: PRT
<213> ORGANISM: Artificial Sequence
<220> FEATURE:
<223> OTHER INFORMATION: MCSF antibody heavy chain variable region
      sequence

<400> SEQUENCE: 30

Met Glu Leu Gly Leu Cys Trp Val Phe Leu Val Ala Ile Leu Glu Gly
1               5                   10                  15

Val Gln Cys Glu Val Gln Leu Val Glu Ser Gly Gly Leu Val Gln
            20                  25                  30

Pro Gly Gly Ser Leu Arg Leu Ser Cys Ala Ala Ser Gly Phe Thr Phe
        35                  40                  45

Ser Ser Phe Ser Met Thr Trp Val Arg Gln Ala Pro Gly Lys Gly Leu
    50                  55                  60

Glu Trp Val Ser Tyr Ile Ser Ser Arg Ser Ser Thr Ile Ser Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Asp Glu Asp Thr Ala Val
            100                 105                 110

Tyr Tyr Cys Ala Arg Asp Pro Leu Leu Ala Gly Ala Thr Phe Phe Asp
        115                 120                 125

Tyr Trp Gly Gln Gly Thr Leu Val Thr Val Ser Ser Ala
    130                 135                 140

<210> SEQ ID NO 31
<211> LENGTH: 128
<212> TYPE: PRT
<213> ORGANISM: Homo sapiens

<400> SEQUENCE: 31

Met Glu Thr Pro Ala Gln Leu Leu Phe Leu Leu Leu Trp Leu Pro
1               5                   10                  15

Asp Thr Thr Gly Glu Phe Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95
```

Ser Arg Leu Glu Pro Glu Asp Phe Ala Val Tyr Tyr Cys Gln Gln Tyr
            100                 105                 110

Gly Ser Ser Pro Leu Thr Phe Gly Gly Gly Thr Lys Val Glu Ile Lys
        115                 120                 125

<210> SEQ ID NO 32
<211> LENGTH: 5
<212> TYPE: PRT
<213> ORGANISM: Homo sapiens

<400> SEQUENCE: 32

Ser Tyr Ser Met Asn
1               5

<210> SEQ ID NO 33
<211> LENGTH: 17
<212> TYPE: PRT
<213> ORGANISM: Homo sapiens

<400> SEQUENCE: 33

Tyr Ile Ser Ser Ser Ser Ser Thr Ile Asp Tyr Ala Asp Ser Val Lys
1               5                   10                  15

Gly

<210> SEQ ID NO 34
<211> LENGTH: 9
<212> TYPE: PRT
<213> ORGANISM: Homo sapiens

<400> SEQUENCE: 34

Glu Ser Gly Trp Tyr Leu Phe Asp Tyr
1               5

<210> SEQ ID NO 35
<211> LENGTH: 11
<212> TYPE: PRT
<213> ORGANISM: Homo sapiens

<400> SEQUENCE: 35

Arg Ala Ser Gln Gly Ile Ser Ser Trp Leu Ala
1               5                   10

<210> SEQ ID NO 36
<211> LENGTH: 7
<212> TYPE: PRT
<213> ORGANISM: Homo sapiens

<400> SEQUENCE: 36

Ala Ala Ser Ser Leu Gln Ser
1               5

<210> SEQ ID NO 37
<211> LENGTH: 9
<212> TYPE: PRT
<213> ORGANISM: Homo sapiens

<400> SEQUENCE: 37

Gln Gln Tyr Asn Ser Tyr Pro Pro Thr
1               5

<210> SEQ ID NO 38
<211> LENGTH: 118
<212> TYPE: PRT
<213> ORGANISM: Homo sapiens

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Ser Gly Trp Tyr Leu Phe Asp Tyr Trp Gly Gln Gly Thr
            100                 105                 110

Leu Val Thr Val Ser Ser
            115

<210> SEQ ID NO 39
<211> LENGTH: 107
<212> TYPE: PRT
<213> ORGANISM: Homo sapiens

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
            100                 105

<210> SEQ ID NO 40
<211> LENGTH: 444
<212> TYPE: PRT
<213> ORGANISM: Homo sapiens

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Asp Glu Asp Thr Ala Val Tyr Tyr Cys
                 85                  90                  95

Ala Arg Glu Ser Gly Trp Tyr Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 41
<211> LENGTH: 214
<212> TYPE: PRT
<213> ORGANISM: Homo sapiens

<400> SEQUENCE: 41

Asp Ile Gln Met Thr Gln Ser Pro Ser Ser Leu Ser Ala Ser Val Gly
1               5                  10                  15
```

```
Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
210
```

PD-L1 ANTAGONIST COMBINATION TREATMENTS

CROSS-REFERENCE TO RELATED APPLICATIONS

This application is a US National Stage Application of International Application PCT/US2016/037498 filed Jun. 15, 2016 (published as WO 2016/205277 on Dec. 22, 2016), which claims priority to U.S. Provisional Application No. 62/180,543 filed Jun. 16, 2015, U.S. Provisional Application No. 62/219,995 filed Sep. 17, 2015, U.S. Provisional Application No. 62/286,501 filed Jan. 25, 2016, and U.S. Provisional Application No. 62/337,489 filed May 17, 2016, each of which is herein incorporated by reference in its entirety.

FIELD

The present invention relates to combination therapies useful for the treatment of cancer. In particular, the invention relates to a combination therapy which comprises an antagonist of a Programmed Death-Ligand 1 protein (PD-L1) and one or more additional therapeutic agent(s).

BACKGROUND

Renal cell carcinoma (RCC) is the most common kidney cancer and constitutes about 3% of all malignant tumors in adults. Until 2005, interferon-alpha (IFN-α) and high-dose interleukin (IL)-2 therapies were the standards of care for patients with advanced RCC (aRCC), albeit with modest efficacy. Since then, development and approval of multiple vascular endothelial growth factor (VEGF) pathway and mammalian target of rapamycin (mTOR) inhibitors have significantly improved the outcomes of aRCC patients. These agents include the VEGF receptor (VEGFR) tyrosine kinase inhibitors (TKIs) sunitinib, pazopanib, axitinib and sorafenib, the mTOR inhibitors temsirolimus and everolimus, and the anti-VEGF monoclonal antibody bevacizumab. However, despite the substantial improvement of patient outcomes with these agents, durable and complete responses in aRCC patients are uncommon; the majority of patients will eventually develop resistance, exhibit disease progression while on therapy, and succumb to death due to metastatic disease.

The programmed death 1 (PD-1) receptor and PD-1 ligands 1 and 2 (PD-L1 and PD-L2, respectively) play integral roles in immune regulation. Expressed on activated T cells, PD-1 is activated by PD-L1 (also known as B7-H1) and PD-L2 expressed by stromal cells, tumor cells, or both, initiating T-cell death and localized immune suppression (Dong et al., Nat Med 1999; 5:1365-69; Freeman et al. J Exp Med 2000; 192:1027-34), potentially providing an immune-tolerant environment for tumor development and growth. Conversely, inhibition of this interaction can enhance local T-cell responses and mediate antitumor activity in nonclinical animal models (Iwai Y, et al. Proc Natl Acad Sci USA 2002; 99:12293-97). Avelumab is a fully human mAb of the IgG1 isotype that specifically targets and blocks PD-L1. Avelumab is the International Nonproprietary Name (INN) for the anti-PD-L1 monoclonal antibody MSB0010718C.

Axitinib is a VEGF receptor (VEGFR) TKI. The antitumor activity of single-agent axitinib 5 mg twice daily (BID) in previously untreated patients with clear cell aRCC was assessed against sorafenib in a randomized, open-label, Phase 3 trial. Although the study did not demonstrate a statistically significant difference in progression-free survival (PFS) between patients treated with axitinib or sorafenib, axitinib was associated with a longer median PFS (mPFS) time (mPFS of 10.1 months (95% CI 7.2,12.1) with axitinib vs. 6.5 months (95% CI 4.7, 8.3) with sorafenib, stratified hazard ratio 0.77 (95% CI 0.56, 1.05)).

4-1BB (CD137 and TNFRSF9), which was first identified as an inducible costimulatory receptor expressed on activated T cells, is a membrane spanning glycoprotein of the Tumor Necrosis Factor (TNF) receptor superfamily. Current understanding of 4-1BB indicates that expression is generally activation dependent and encompasses a broad subset of immune cells including activated NK and NKT cells; regulatory T cells; dendritic cells (DC) including follicular DC; stimulated mast cells, differentiating myeloid cells, monocytes, neutrophils, eosinophils, and activated B cells. 4-1BB expression has also been demonstrated on tumor vasculature (19-20) and atherosclerotic endothelium. The ligand that stimulates 4-1BB (4-1BBL) is expressed on activated antigen presenting cells (APCs), myeloid progenitor cells and hematopoietic stem cells. 4-1BB agonist mAbs increase costimulatory molecule expression and markedly enhance cytolytic T lymphocyte responses, resulting in anti-tumor efficacy in various models. 4-1BB agonist mAbs have demonstrated efficacy in prophylactic and therapeutic settings and both monotherapy and combination therapy tumor models and have established durable anti-tumor protective T cell memory responses.

Macrophage colony stimulating factor (M-CSF) is a member of the family of proteins referred to as colony stimulating factors (CSFs). M-CSF, also known as CSF-1, is a secreted or a cell surface glycoprotein comprised of two subunits that are joined by a disulfide bond with a total molecular mass varying from 40 to 90 kD (Stanley E. R., et al., Mol. Reprod. Dev., 46:4-10 (1997)). Similar to other CSFs, M-CSF is produced by macrophages, monocytes, and human joint tissue cells, such as chondrocytes and synovial fibroblasts, in response to proteins such as interleukin-1 or tumor necrosis factor-alpha. M-CSF stimulates the formation of macrophage colonies from pluripotent hematopoietic progenitor stem cells (Stanley E. R., et al., Mol. Reprod. Dev., 46:4-10 (1997)). M-CSF typically binds to its receptor, c-fms, in order to exert a biological effect. c-fms contains five extracellular Ig domains, one transmembrane domain, and an intracellular domain with two kinase domains. Upon M-CSF binding to c-fms, the receptor homo-dimerizes and initiates a cascade of signal transduction pathways including the JAK/STAT, PI3K, and ERK pathways.

The OX40 receptor (OX40, also known as CD134, TNFRSF4, ACT-4, ACT35, and TXGP1L) is a member of the TNF receptor superfamily. OX40 is found to be expressed on activated CD4+ T-cells. High numbers of OX40+ T cells have been demonstrated within tumors (tumor infiltrating lymphocytes) and in the draining lymph nodes of cancer patients (Weinberg, A. et al., J. Immunol. 164: 2160-69, 2000; Petty, J. et al., Am. J. Surg. 183: 512-518, 2002). It was shown in tumor models in mice that engagement of OX40 in vivo during tumor priming significantly delayed and prevented the appearance of tumors as compared to control treated mice (Weinberg et al., 2000). Therefore, it has been contemplated to enhance the immune response of a mammal to an antigen by engaging OX40 through the use of an OX40 binding agent (WO 99/42585; Weinberg et al., 2000).

The rituximab antibody is a genetically engineered chimeric murine/human monoclonal antibody directed against the CD20 antigen. Rituximab is the antibody called "C2B8" in U.S. Pat. No. 5,736,137 issued Apr. 7, 1998 (Anderson et al.). Rituximab is indicated for the treatment of patients with relapsed or refractory low-grade or follicular, CD20 positive, B cell non-Hodgkin's lymphoma. In vitro mechanism of action studies have demonstrated that rituximab binds human complement and lyses lymphoid B cell lines through complement-dependent cytotoxicity (CDC) (Reff et al. *Blood* 83(2):435-445 (1994)). Additionally, it has significant activity in assays for antibody-dependent cellular cytotoxicity (ADCC).

There is a need for improved therapies for the treatment of cancers. Furthermore, there is a need for therapies having greater efficacy than existing therapies. Preferred combination therapies of the present invention show greater efficacy than treatment with either therapeutic agent alone.

SUMMARY

This invention relates to therapeutic regimens for the treatment of cancer.

Provided herein are methods for treating a cancer in a subject. Also provided are methods of inhibiting tumor growth or progression in a subject who has malignant cells. Also provided are methods of inhibiting metastasis of malignant cells in a subject. Also provided are methods of inducing tumor regression in a subject who has malignant cells.

In some embodiments, the method comprises administering to the subject a combination therapy which comprises a PD-L1 antagonist and a VEGFR inhibitor. In some embodiments, the invention provides a medicament comprising a PD-L1 antagonist for use in combination with a VEGFR inhibitor for treating a cancer. In some embodiments, the invention provides a medicament comprising a VEGFR inhibitor for use in combination with a PD-L1 antagonist for treating a cancer. Other embodiments provide for the use of a PD-L1 antagonist in the manufacture of a medicament for treating a cancer in a subject when administered in combination with a VEGFR inhibitor and use of a VEGFR inhibitor in the manufacture of a medicament for treating a cancer in a subject when administered in combination with a PD-L1 antagonist. In some embodiments, the invention provides use of a PD-L1 antagonist and a VEGFR inhibitor in the manufacture of medicaments for treating a cancer in a subject. In some embodiments, the medicaments comprise a kit, and the kit also comprises a package insert comprising instructions for using the PD-L1 antagonist in combination with a VEGFR inhibitor to treat a cancer in a subject. In all of the above embodiments of the treatment method, medicaments and uses herein, the VEGFR inhibitor is N-methyl-2-[3-((E)-2-pyridin-2-yl-vinyl)-1H-indazol-6-ylsulfanyl]-benzamide or a pharmaceutically acceptable salt thereof.

Also provided are kits comprising a first container, a second container and a package insert, wherein the first container comprises at least one dose of a medicament comprising an anti-PD-L1 antagonist, the second container comprises at least one dose of a medicament comprising a VEGFR inhibitor, and the package insert comprises instructions for treating a subject for cancer using the medicaments.

In some embodiments of the above methods, medicaments, uses or kits, the VEGFR inhibitor can be axitinib and can be formulated as a 1 mg tablet, 3 mg tablet, or a 5 mg tablet.

In some embodiments, the method comprises administering to the subject a combination therapy which comprises a PD-L1 antagonist and an anti-4-1 BB antibody. In some embodiments, the method comprises administering to the subject a combination therapy which comprises a PD-L1 antagonist and an anti-M-CSF antibody. In some embodiments, the method comprises administering to the subject a combination therapy which comprises a PD-L1 antagonist and an anti-OX40 antibody. In some embodiments, the method comprises administering to the subject a combination therapy which comprises a PD-L1 antagonist, an anti-4-1BB antibody, and an anti-M-CSF antibody. In some embodiments, the method comprises administering to the subject a combination therapy which comprises a PD-L1 antagonist, an anti-4-1BB antibody, and an anti-OX40 antibody.

In some embodiments, the method comprises administering to the subject a combination therapy which comprises a PD-L1 antagonist and a CD20 antagonist. In some embodiments, the method comprises administering to the subject a combination therapy which comprises a PD-L1 antagonist, a CD20 antagonist, and an anti-4-1BB antibody. In some embodiments, the PD-L1 antagonist is avelumab and the CD20 antagonist is rituximab. In some embodiments, the anti-4-1BB antibody is PF-05082566. In some embodiments, the method comprises administering rituximab at a dose of 375 mg/m$^2$ IV on Day 1 of a 28 day cycle, PF-05082566 at a fixed dose of 100 mg as a 1 hour IV infusion on Day 2 of each cycle, and avelumab as a 1 hour IV infusion on Day 2 and Day 16 of each cycle at a dose of 10 mg/kg. In some embodiments, the method comprises administering rituximab at a dose of 375 mg/m$^2$ IV on Day 1 of a 28 day cycle, PF-05082566 at a fixed dose of 100 mg as a 1 hour IV infusion on Day 1 of each cycle, and avelumab as a 1 hour IV infusion on Day 2 and Day 16 of each cycle at a dose of 10 mg/kg. In some embodiments, the method comprises administering rituximab at a dose of 375 mg/m$^2$ IV on Day 1 of a 28 day cycle, PF-05082566 at a fixed dose of 100 mg as a 1 hour IV infusion on Day 1 of each cycle, and avelumab as a 1 hour IV infusion on Day 1 and Day 15 of each cycle at a dose of 10 mg/kg. In some embodiments, the method comprises administering rituximab at a dose of 375 mg/m$^2$ IV on Day 1 of a 28 day cycle, PF-05082566 at a fixed dose of 100 mg as a 1 hour IV infusion on Day 2 of each cycle, and avelumab as a 1 hour IV infusion on Day 1 and Day 15 of each cycle at a dose of 10 mg/kg. In some embodiments, avelumab is administered at least 3 hours after PF-05082566 when avelumab and PF-05082566 are administered on the same day. In some embodiments, avelumab is administered about 60 minutes after PF-05082566 when avelumab and PF-05082566 are administered on the same day. In some embodiments, avelumab is administered about 30 minutes after PF-05082566 when avelumab and PF-05082566 are administered on the same day. In some embodiments, the cancer is R/R DLBCL.

In some embodiments, the method comprises administering to the subject a combination therapy which comprises a PD-L1 antagonist, a CD20 antagonist, and bendamustine. In some embodiments, the method comprises administering to the subject a combination therapy which comprises a PD-L1 antagonist, a CD20 antagonist, and bendamustine. In some embodiments, the PD-L1 antagonist is avelumab and the CD20 antagonist is rituximab. In some embodiments, the method comprises administering rituximab at a dose of 375 mg/m$^2$ IV on Day 1 of a 28 day cycle, bendamustine at a dose of 90 mg/m$^2$ IV on Day 2 and Day 3 of each 28 day cycle, and avelumab as a 1 hour IV infusion on Day 2 and Day 16 of each cycle at a dose of 10 mg/kg. In some embodiments, the method comprises administering rituximab at a dose of 375 mg/m$^2$ IV on Day 1 of a 28 day cycle, bendamustine at a dose of 90 mg/m$^2$ IV on Day 1 and Day 2 of each 28 day cycle, and avelumab as a 1 hour IV infusion on Day 2 and Day 16 of each cycle at a dose of 10 mg/kg. In some embodiments, the method comprises administering rituximab at a dose of 375 mg/m² IV on Day 1 of a 28 day cycle, bendamustine at a dose of 90 mg/m² IV on Day 2 and Day 3 of each 28 day cycle, and avelumab as a 1 hour IV infusion on Day 1 and Day 15 of each cycle at a dose of 10 mg/kg. In some embodiments, the method comprises administering rituximab at a dose of 375 mg/m² IV on Day 1 of a 28 day cycle, bendamustine at a dose of 90 mg/m² IV on Day 1 and Day 2 of each 28 day cycle, and avelumab as a 1 hour IV infusion on Day 1 and Day 15 of each cycle at a dose of 10 mg/kg. In some embodiments, avelumab is administered at least 3 hours after bendamustine when avelumab and bendamustine are administered on the same day. In some embodiments, the cancer is R/R DLBCL.

In some embodiments, the method comprises administering to the subject a combination therapy which comprises a PD-L1 antagonist, azacitidine, and an anti-4-1BB antibody. In some embodiments, the method comprises administering to the subject a combination therapy which comprises avelumab, azacitidine, and PF-05082566. In some embodiments, the method comprises administering azacitidine at a daily dose of 75 mg/m² subcutaneously (SC) each day from Day 1 to Day 7 of a 28 day cycle, PF-05082566 at a fixed dose of 100 mg as a 1 hour IV infusion on Day 2 of each cycle, and avelumab as a 1 hour IV infusion on Day 2 and Day 16 of each cycle at a dose of 10 mg/kg. In some embodiments, the method comprises administering azacitidine at a daily dose of 75 mg/m² SC each day from Day 1 to Day 7 of a 28 day cycle, PF-05082566 at a fixed dose of 100 mg as a 1 hour IV infusion on Day 1 of each cycle, and avelumab as a 1 hour IV infusion on Day 2 and Day 16 of each cycle at a dose of 10 mg/kg. In some embodiments, the method comprises administering azacitidine at a daily dose of 75 mg/m² SC each day from Day 1 to Day 7 of a 28 day cycle, PF-05082566 at a fixed dose of 100 mg as a 1 hour IV infusion on Day 1 of each cycle, and avelumab as a 1 hour IV infusion on Day 1 and Day 15 of each cycle at a dose of 10 mg/kg. In some embodiments, the method comprises administering azacitidine at a daily dose of 75 mg/m² SC each day from Day 1 to Day 7 of a 28 day cycle, PF-05082566 at a fixed dose of 100 mg as a 1 hour IV infusion on Day 2 of each cycle, and avelumab as a 1 hour IV infusion on Day 1 and Day 15 of each cycle at a dose of 10 mg/kg. In some embodiments, on the days when avelumab is administered on the same day as azacitidine, avelumab is administered at least 3 hours after administration of azacitidine. In some embodiments, avelumab is administered at least 3 hours after PF-05082566 when avelumab and PF-05082566 are administered on the same day. In some embodiments, avelumab is administered about 60 minutes after PF-05082566 when avelumab and PF-05082566 are administered on the same day. In some embodiments, avelumab is administered about 30 minutes after PF-05082566 when avelumab and PF-05082566 are administered on the same day. In some embodiments, the cancer is R/R DLBCL.

In some embodiments, the method comprises administering to the subject a combination therapy which comprises avelumab and PF-05082566. In some embodiments, the cancer is advanced NSCLC, RCC, or urothelial cancer which was resistant (responded and then progressed) or refractory (never responded) to prior therapy(ies), including for example a single-agent immune checkpoint inhibitor (e.g., anti-PD-1 antibody, anti-PD-L1 antibody, or anti-CTLA-4 antibody treatment). In some embodiments, avelumab is administered as a 1 hour IV infusion every 2 weeks at a dose of 10 mg/kg, PF-05082566 is administered at a fixed dose of 10 mg as a 1 hour IV infusion once every four weeks on Day 1 of each cycle, and on days when both avelumab and PF-05082566 are administered, PF-05082566 is administered first, followed by avelumab infusion within 30 minutes after the end of the PF-05082566 infusion.

In some embodiments, the method comprises administering to the subject a combination therapy which comprises avelumab and chemoradiotherapy. In some embodiments, the chemoradiotherapy comprises cisplatin and definitive radiation therapy. In some embodiments, subject has locally-advanced squamous cell carcinoma of the head and neck (SCCHN). In some embodiments, the SCCHN is localized to the oral cavity, oropharynx, larynx, or hypopharynx. In some embodiments, the method comprises a lead-in phase and a chemoradiotherapy (CRT) phase, wherein the lead-in phase begins seven days prior to initiation of the CRT phase. In some embodiments, avelumab is administered at a dose of 10 mg/kg on Day 1 of the lead-in phase' and on Day 8, Day 29, and Day 39 of the CRT phase; cisplatin is administered at a dose of 100 mg/m² on Day 1, Day 22, and Day 23 of the CRT phase; and radiation therapy is 70 Gy/33-35 fractions/day, 5 fractions/week intensity modulated radiation therapy (IMRT). In some embodiments, the method comprises a maintenance phase which begins two weeks after completion of the CRT phase. In some embodiments, the maintenance phase comprises administration of avelumab at a dose of 10 mg/kg every two weeks (Q2W) after completion of the CRT phase.

In all of the above treatment methods, medicaments and uses, the PD-L1 antagonist inhibits the binding of PD-L1 to PD-1. In some embodiments of the above treatment methods, medicaments and uses, the PD-L1 antagonist is a monoclonal antibody, or an antigen binding fragment thereof, which specifically binds to PD-L1 or to PD-1 and blocks the binding of PD-L1 to PD-1. In some embodiments, the PD-L1 antagonist is an anti-PD-L1 antibody which comprises three complementarity determining regions (CDRs) from a heavy chain variable region comprising the amino acid sequence shown in SEQ ID NO: 8 and three CDRs from a light chain variable region comprising the amino acid sequences shown in SEQ ID NO: 9. In some embodiments, the PD-L1 antagonist is an anti-PD-L1 antibody which comprises heavy and light chain variable regions comprising the amino acid sequences shown in SEQ ID NO: 8 and SEQ ID NO: 9, respectively.

In some embodiments, the invention provides a medicament comprising a PD-L1 antagonist for use in combination with an anti-4-1BB antibody for treating a cancer.

In some embodiments, the invention provides a medicament comprising an anti-4-1BB antibody for use in combination with a PD-L1 antagonist for treating a cancer.

Other embodiments provide for the use of a PD-L1 antagonist in the manufacture of a medicament for treating a cancer in a subject when administered in combination with an anti-4-1BB antibody and use of an anti-4-1BB antibody in the manufacture of a medicament for treating a cancer in a subject when administered in combination with a PD-L1 antagonist.

In some embodiments, the invention provides use of a PD-L1 antagonist and an anti-4-1BB antibody in the manufacture of medicaments for treating a cancer in a subject. In some embodiments, the medicaments comprise a kit, and the kit also comprises a package insert comprising instructions for using the PD-L1 antagonist in combination with an anti-4-1BB antibody to treat a cancer in a subject.

In some embodiments, the invention provides a medicament comprising a PD-L1 antagonist for use in combination with an anti-M-CSF antibody for treating a cancer.

In some embodiments, the invention provides a medicament comprising an anti-M-CSF antibody for use in combination with a PD-L1 antagonist for treating a cancer.

Other embodiments provide for the use of a PD-L1 antagonist in the manufacture of a medicament for treating a cancer in a subject when administered in combination with an anti-M-CSF antibody and use of an anti-M-CSF antibody in the manufacture of a medicament for treating a cancer in a subject when administered in combination with a PD-L1 antagonist.

In some embodiments, the invention provides use of a PD-L1 antagonist and an anti-M-CSF antibody in the manufacture of medicaments for treating a cancer in a subject. In some embodiments, the medicaments comprise a kit, and the kit also comprises a package insert comprising instructions for using the PD-L1 antagonist in combination with an anti-M-CSF antibody to treat a cancer in a subject.

In some embodiments, the invention provides a medicament comprising a PD-L1 antagonist for use in combination with an anti-OX40 antibody for treating a cancer.

In some embodiments, the invention provides a medicament comprising an anti-OX40 antibody for use in combination with a PD-L1 antagonist for treating a cancer.

Other embodiments provide for the use of a PD-L1 antagonist in the manufacture of a medicament for treating a cancer in a subject when administered in combination with an anti-OX40 antibody and use of an anti-OX40 antibody in the manufacture of a medicament for treating a cancer in a subject when administered in combination with a PD-L1 antagonist.

In some embodiments, the invention provides for the use of a PD-L1 antagonist and an anti-OX40 antibody in the manufacture of medicaments for treating a cancer in a subject. In some embodiments, the medicaments comprise a kit, and the kit also comprises a package insert comprising instructions for using the PD-L1 antagonist in combination with an anti-OX40 antibody to treat a cancer in a subject.

In some embodiments, the invention provides a medicament comprising a PD-L1 antagonist for use in combination with an anti-M-CSF antibody for treating a cancer.

In some embodiments, the invention provides a medicament comprising an anti-M-CSF antibody for use in combination with a PD-L1 antagonist for treating a cancer.

Other embodiments provide for the use of a PD-L1 antagonist in the manufacture of a medicament for treating a cancer in a subject when administered in combination with an anti-M-CSF antibody and use of an anti-M-CSF antibody in the manufacture of a medicament for treating a cancer in a subject when administered in combination with a PD-L1 antagonist.

In some embodiments, the invention provides for the use of a PD-L1 antagonist and an anti-M-CSF antibody in the manufacture of medicaments for treating a cancer in a subject. In some embodiments, the medicaments comprise a kit, and the kit also comprises a package insert comprising instructions for using the PD-L1 antagonist in combination with an anti-M-CSF antibody to treat a cancer in a subject.

In some embodiments, the invention provides a medicament comprising a PD-L1 antagonist for use in combination with an anti-OX40 antibody for treating a cancer.

In some embodiments, the invention provides a medicament comprising an anti-OX40 antibody for use in combination with a PD-L1 antagonist for treating a cancer.

Other embodiments provide for the use of a PD-L1 antagonist in the manufacture of a medicament for treating a cancer in a subject when administered in combination with an anti-OX40 antibody and use of an anti-OX40 antibody in the manufacture of a medicament for treating a cancer in a subject when administered in combination with a PD-L1 antagonist.

In some embodiments, the invention provides for the use of a PD-L1 antagonist and an anti-OX40 antibody in the manufacture of medicaments for treating a cancer in a subject. In some embodiments, the medicaments comprise a kit, and the kit also comprises a package insert comprising instructions for using the PD-L1 antagonist in combination with an anti-OX40 antibody to treat a cancer in a subject.

In some embodiments, the invention provides a medicament comprising a PD-L1 antagonist for use in combination with an anti-4-1BB antibody and an anti-M-CSF antibody for treating a cancer.

In some embodiments, the invention provides a medicament comprising an anti-4-1BB antibody and an anti-M-CSF antibody for use in combination with a PD-L1 antagonist for treating a cancer.

Other embodiments provide for the use of a PD-L1 antagonist in the manufacture of a medicament for treating a cancer in a subject when administered in combination with an anti-4-1BB antibody and an anti-M-CSF antibody and use of an anti-4-1BB antibody and an anti-M-CSF antibody in the manufacture of a medicament for treating a cancer in a subject when administered in combination with a PD-L1 antagonist.

In some embodiments, the invention provides for the use of a PD-L1 antagonist and an anti-4-1BB antibody and an anti-M-CSF antibody in the manufacture of medicaments for treating a cancer in a subject. In some embodiments, the medicaments comprise a kit, and the kit also comprises a package insert comprising instructions for using the PD-L1 antagonist in combination with an anti-4-1BB antibody and an anti-M-CSF antibody to treat a cancer in a subject.

In some embodiments, the invention provides a medicament comprising a PD-L1 antagonist for use in combination with an anti-4-1BB antibody and an anti-OX40 antibody for treating a cancer.

In some embodiments, the invention provides a medicament comprising an anti-4-1BB antibody and an anti-OX40 antibody for use in combination with a PD-L1 antagonist for treating a cancer.

Other embodiments provide for the use of a PD-L1 antagonist in the manufacture of a medicament for treating a cancer in a subject when administered in combination with an anti-4-1BB antibody and an anti-OX40 antibody and use of an anti-4-1BB antibody and an anti-OX40 antibody in the manufacture of a medicament for treating a cancer in a subject when administered in combination with a PD-L1 antagonist.

In some embodiments, the invention provides for the use of a PD-L1 antagonist and an anti-4-1BB antibody and an anti-OX40 antibody in the manufacture of medicaments for treating a cancer in a subject. In some embodiments, the medicaments comprise a kit, and the kit also comprises a package insert comprising instructions for using the PD-L1 antagonist in combination with an anti-4-1BB antibody and an anti-OX40 antibody to treat a cancer in a subject.

In all of the above treatment methods, medicaments and uses, the PD-L1 antagonist inhibits the binding of PD-L1 to PD-1. In some embodiments of the above treatment methods, medicaments and uses, the PD-L1 antagonist is a monoclonal antibody, or an antigen binding fragment thereof, which specifically binds to PD-L1 or to PD-1 and blocks the binding of PD-L1 to PD-1. In some embodiments, the PD-L1 antagonist is an anti-PD-L1 antibody which comprises three CDRs from a heavy chain variable region comprising the amino acid sequence shown in SEQ ID NO: 8 and three CDRs from a light chain variable region comprising the amino acid sequence shown in SEQ ID NO: 9. In some embodiments, the PD-L1 antagonist is an anti-PD-L1 antibody which comprises heavy and light chain variable regions comprising the amino acid sequences shown in SEQ ID NO: 8 and SEQ ID NO: 9, respectively. In some embodiments, the anti-PD-L1 antibody is Avelumab.

In some embodiments, the anti-4-1BB antibody can comprise a heavy chain variable region comprising three CDRs from the heavy chain variable region having the amino acid sequence shown in SEQ ID NO: 18, and a light chain variable region comprising three CDRs from the light chain variable region having the amino acid sequence shown in SEQ ID NO: 19. In some embodiments, the anti-4-1BB antibody can comprise heavy and light chain variable regions comprising the amino acid sequences shown in SEQ ID NO: 18 and SEQ ID NO: 19, respectively. In some embodiments, the anti-4-1BB antibody is PF-05082566.

In some embodiments, the anti-M-CSF antibody can comprise a heavy chain variable region comprising three CDRs from the heavy chain variable region having the amino acid sequence shown in SEQ ID NO: 30, and a light chain variable region comprising three CDRs from the light chain variable region having the amino acid sequence shown in SEQ ID NO: 31. In some embodiments, the anti-M-CSF antibody can comprise heavy and light chain variable regions comprising the amino acid sequences shown in SEQ ID NO: 30 and SEQ ID NO: 31, respectively. In some embodiments, the anti-M-CSF antibody is PD-0360324.

In some embodiments, the anti-OX40 antibody can comprise a heavy chain variable region comprising three CDRs from the heavy chain variable region having the amino acid sequence shown in SEQ ID NO: 38, and a light chain variable region comprising three CDRs from the light chain variable region having the amino acid sequence shown in SEQ ID NO: 39. In some embodiments, the anti-OX40 antibody can comprise a heavy chain variable region comprising the amino acid sequence shown in SEQ ID NO: 38, and a light chain variable region comprising the amino acid sequence shown in SEQ ID NO: 39. In some embodiments, the anti-OX40 antibody is PF-04518600.

In some embodiments of the above treatment methods, medicaments and uses of the invention, the individual is a human and the cancer is a solid tumor. In some embodiments, the solid tumor is renal cell carcinoma (RCC), bladder cancer, breast cancer, clear cell kidney cancer, head/neck squamous cell carcinoma (SCCHN), lung squamous cell carcinoma, malignant melanoma, non-small-cell lung cancer (NSCLC), ovarian cancer, pancreatic cancer, prostate cancer, small-cell lung cancer (SCLC) or triple negative breast cancer.

In other embodiments of the above treatment methods, medicaments and uses of the invention, the individual is a human and the cancer is a Heme malignancy and in some embodiments, the Heme malignancy is acute lymphoblastic leukemia (ALL), acute myeloid leukemia (AML), chronic lymphocytic leukemia (CLL), chronic myeloid leukemia (CML), diffuse large B-cell lymphoma (DLBCL), EBV-positive DLBCL, primary mediastinal large B-cell lymphoma, T-cell/histiocyte-rich large B-cell lymphoma, follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL).

Also, in some embodiments of any of the above treatment methods, medicaments and uses, the cancer tests positive for the expression of one or both of PD-L1 and PD-L2. In still other embodiments, the cancer has elevated PD-L1 expression.

In some embodiments of the above treatment methods, medicaments and uses, the subject is a human and the cancer is RCC that tests positive for human PD-L1.

In some embodiments of the above treatment methods, medicaments and uses, the cancer is advanced RCC with clear cell subtype and is present in a human who has not been previously treated for RCC.

In some embodiments of the above treatment methods, medicaments and uses, the cancer is relapsed or refractory (R/R) cancer. In some embodiments, the R/R cancer is R/R DLBCL.

In some embodiments of the above treatment methods, medicaments and uses, the cancer is locally advanced cancer. In some embodiments, the locally advanced cancer is locally advanced SCCHN. In some embodiments, the SCCHN is localized to the oral cavity, oropharynx, larynx, or hypopharynx.

BRIEF DESCRIPTION OF THE FIGURES/DRAWINGS

DETAILED DESCRIPTION

I. Definitions

Figure 1:
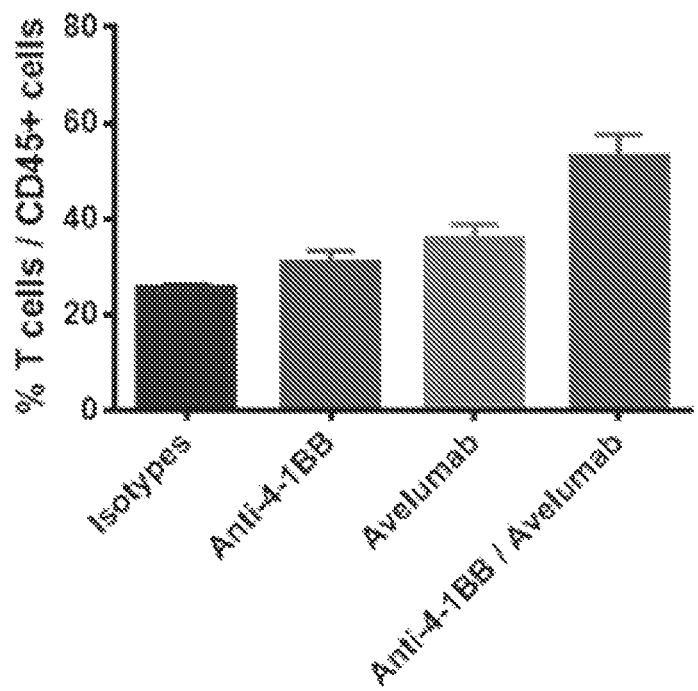
FIG. 1 depicts a graph summarizing infiltration of T cells in response to treatment.

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

"About," when used to modify a numerically defined parameter (e.g., the dose of a PD-L1 antagonist or VEGFR inhibitor, or the length of treatment time with a combination therapy described herein), means that the parameter may vary by as much as 10% below or above the stated numerical value for that parameter. For example, a dose of about 5 mg/kg may vary between 4.5 mg/kg and 5.5 mg/kg.

As used herein, including the appended claims, the singular forms of words such as "a," "an," and "the," include their corresponding plural references unless the context clearly dictates otherwise.

"Administration" and "treatment," as they apply to an animal, human, experimental subject, cell, tissue, organ, or biological fluid, refer to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')2, Fv), single chain (scFv) and domain antibodies (including, for example, shark and camelid antibodies), and fusion proteins comprising an antibody, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, lgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding fragment" or "antigen binding portion" of an antibody, as used herein, refers to one or more fragments of an intact antibody that retain the ability to specifically bind to a given antigen (e.g., PD-L1). Antigen binding functions of an antibody can be performed by fragments of an intact antibody. Examples of binding fragments encompassed within the term "antigen binding fragment" of an antibody include Fab; Fab'; F(ab')2; an Fd fragment consisting of the VH and CH1 domains; an Fv fragment consisting of the VL and VH domains of a single arm of an antibody; a single domain antibody (dAb) fragment (Ward et al., Nature 341:544-546, 1989); and an isolated complementarity determining region (CDR).

An antibody, an antibody conjugate, or a polypeptide that "preferentially binds" or "specifically binds" (used interchangeably herein) to a target (e.g., PD-L1 protein) is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a PD-L1 epitope is an antibody that binds this epitope with greater affinity, avidity, more readily, and/or with greater duration than it binds to other PD-L1 epitopes or non-PD-L1 epitopes. It is also understood that by reading this definition, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (i.e., Kabat et al. Sequences of Proteins of Immunological Interest (5th ed., 1991, National Institutes of Health, Bethesda Md.)); and (2) an approach based on crystallographic studies of antigen-antibody complexes (Al-lazikani et al., 1997, J. Molec. Biol. 273:927-948). As used herein, a CDR may refer to CDRs defined by either approach or by a combination of both approaches.

A "CDR" of a variable domain comprises amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283:1156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

"Isolated antibody" and "isolated antibody fragment" refer to the purification status and in such context mean the named molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Monoclonal antibody," "mAb," or "Mab," as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975), Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991), Nature 352: 624-628 and Marks et al. (1991), J. Mol. Biol. 222: 581-597, for example. See also Presta (2005), J. Allergy Clin. Immunol. 116:731.

"Chimeric antibody" refers to an antibody in which a portion of the heavy and/or light chain is identical or homologous to corresponding sequences in an antibody derived from a particular species (e.g., human) or belonging to a particular antibody class or subclass, while the remainder of the chain(s) is identical or homologous to corresponding sequences in an antibody derived from another species (e.g., mouse) or belonging to another antibody class or subclass, as well as fragments of such antibodies, so long as they exhibit the desired biological activity.

"Human antibody" refers to an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" refers to an antibody that comprises only mouse or rat immunoglobulin sequences, respectively.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum," "hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

The terms "cancer," "cancerous," and "malignant" refer to or describe the physiological condition in mammals that is typically characterized by unregulated cell growth. Examples of cancer include, but are not limited to, carcinoma, lymphoma, leukemia, blastoma, and sarcoma. More particular examples of such cancers include squamous cell carcinoma, myeloma, small-cell lung cancer, non-small cell lung cancer, glioma, Hodgkin's lymphoma, non-Hodgkin's lymphoma, acute myeloid leukemia (AML), multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, and head and neck cancer. Another particular example of cancer includes renal cell carcinoma.

"Biotherapeutic agent" means a biological molecule, such as an antibody or fusion protein, that blocks ligand/receptor signaling in any biological pathway that supports tumor maintenance and/or growth or suppresses the anti-tumor immune response.

"Chemotherapeutic agent" is a chemical compound useful in the treatment of cancer. Classes of chemotherapeutic agents include, but are not limited to: alkylating agents, antimetabolites, kinase inhibitors, spindle poison plant alkaloids, cytotoxic/antitumor antibiotics, topisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists, anti-androgens, aromatase inhibitors, EGFR inhibitors, VEGF inhibitors, and anti-sense oligonucleotides that inhibit expression of genes implicated in abnormal cell proliferation or tumor growth. Chemotherapeutic agents useful in the treatment methods of the present invention include cytostatic and/or cytotoxic agents.

"Conservatively modified variants" or "conservative substitution" refers to substitutions of amino acids in a protein with other amino acids having similar characteristics (e.g., charge, side-chain size, hydrophobicity/hydrophilicity, backbone conformation and rigidity, etc.), such that the changes can frequently be made without altering the biological activity or other desired property of the protein, such as antigen affinity and/or specificity. Those of skill in this art recognize that, in general, single amino acid substitutions in non-essential regions of a polypeptide do not substantially alter biological activity (see, e.g., Watson et al. (1987), Molecular Biology of the Gene, The Benjamin/Cummings Pub. Co., p. 224 (4th Ed.)). In addition, substitutions of structurally or functionally similar amino acids are less likely to disrupt biological activity. Exemplary conservative substitutions are set forth in Table 1 below.

TABLE 1

Exemplary Conservative Amino Acid Substitutions

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |

TABLE 1-continued

Exemplary Conservative Amino Acid Substitutions

| Original residue | Conservative substitution |
| --- | --- |
| Ser (S) | Thr |
| Thr (T) | Ser |
| Trp (W) | Tyr; Phe |
| Tyr (Y) | Trp; Phe |
| Val (V) | Ile; Leu |

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a PD-L1 antagonist that consists essentially of a recited amino acid sequence may also include one or more amino acids, including substitutions of one or more amino acid residues, which do not materially affect the properties of the binding compound.

"Diagnostic anti-PD-L1 monoclonal antibody" means a mAb which specifically binds to PD-L1 that is expressed on the surface of certain mammalian cells. A mature PD-L1 lacks the presecretory leader sequence, also referred to as leader peptide The terms "PD-L1" and "mature PD-L1" are used interchangeably herein, and shall be understood to mean the same molecule unless otherwise indicated or readily apparent from the context.

As used herein, an anti-human PD-L1 mAb or a diagnostic anti-hPD-L1 mAb refers to a monoclonal antibody that specifically binds to mature human PD-L1. A mature human PD-L1 molecule consists of amino acids 19-290 of the following sequence (SEQ ID NO: 1): MRIFAVFIFMTY-WHLLNAFTVTVPKDLYVVEYGSNMTIEC KFPVEKQLDLAALIVYWEMEDKNIIQFVH-GEEDLKVQHSSYRQRARLLKDQLSLGNAAL QITDVKLQ DAGVYRCM ISYGGA-DYKRITVKVNAPYNKINQRILVVDPVTSEHELTCQAE GYPKAEVIWTSSDHQVLSGKTTTTNSKREEKLFNVT-STLRINTTTNEIFYCTFRRLDPEE NHTAELVIPEL-PLAHPPNERTHLVILGAILLCLGVALTFI-FRLRKGRMMDVKKCGIQDTNS KKQSDTHLEET (SEQ ID NO: 1).

"Homology" refers to sequence similarity between two polypeptide sequences when they are optimally aligned. When a position in both of the two compared sequences is occupied by the same amino acid monomer subunit, e.g., if a position in a light chain CDR of two different Abs is occupied by alanine, then the two Abs are homologous at that position. The percent of homology is the number of homologous positions shared by the two sequences divided by the total number of positions compared ×100. For example, if 8 of 10 of the positions in two sequences are matched or homologous when the sequences are optimally aligned then the two sequences are 80% homologous. Generally, the comparison is made when two sequences are aligned to give maximum percent homology. For example, the comparison can be performed by a BLAST algorithm wherein the parameters of the algorithm are selected to give the largest match between the respective reference sequences over the entire length of the respective reference sequences.

The following references relate to BLAST algorithms often used for sequence analysis: BLAST ALGORITHMS: Altschul, S. F., et al. (1990), J. Mol. Biol. 215:403-410; Gish, W., et al. (1993), Nature Genet. 3:266-272; Madden, T. L., et al. (1996), Meth. Enzymol. 266:131-141; Altschul, S. F., et al. (1997), Nucleic Acids Res. 25:3389-3402; Zhang, J., et al. (1997), Genome Res. 7:649-656; Wootton, J. C., et al. (1993), Comput. Chem. 17:149-163; Hancock, J. M. et al. (1994), Comput. Appl. Biosci. 10:67-70; ALIGNMENT SCORING SYSTEMS: Dayhoff, M. O., et al. "A model of evolutionary change in proteins." in Atlas of Protein Sequence and Structure (1978), vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure (1978), vol. 5, suppl. 3." M. O. Dayhoff (ed.), pp. 353-358, Natl. Biomed. Res. Found., Washington, D.C.; Altschul, S. F. (1991), J. Mol. Biol. 219:555-565; States, D. J., et al. (1991), Methods 3:66-70; Henikoff, S., et al. (1992), Proc. Natl. Acad. Sci. USA 89:10915-10919; Altschul, S. F., et al. (1993), J. Mol. Evol. 36:290-300; ALIGNMENT STATISTICS: Karlin, S., et al. (1990), Proc. Natl. Acad. Sci. USA 87:2264-2268; Karlin, S., et al. (1993), Proc. Natl. Acad. Sci. USA 90:5873-5877; Dembo, A., et al. (1994), Ann. Prob. 22:2022-2039; and Altschul, S. F., "Evaluating the statistical significance of multiple distinct local alignments." in Theoretical and Computational Methods in Genome Research (S. Suhai, ed.) (1997), pp. 1-14, Plenum, New York.

"Patient" or "subject" refers to any single subject for which therapy is desired or that is participating in a clinical trial, epidemiological study or used as a control, including humans and mammalian veterinary patients such as cattle, horses, dogs, and cats.

"PD-L1 antagonist" means any chemical compound or biological molecule that blocks binding of PD-L1 expressed on a cancer cell to PD-1. In any of the treatment methods, medicaments and uses of the present invention in which a human subject is being treated, the PD-L1 antagonist blocks binding of human PD-L1 to human PD-1.

PD-L1 antagonists useful in any of the treatment methods, medicaments, and uses of the present invention include a monoclonal antibody (mAb) which specifically binds to PD-L1, and preferably specifically binds to human PD-L1. The mAb may be a human antibody, a humanized antibody or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')2, scFv and Fv fragments.

Examples of mAbs that bind to human PD-L1, and useful in the treatment methods, medicaments and uses of the present invention, are described in WO 2013/079174, WO 2015/061668, WO 2010/089411, WO 2007/005874, WO 2010/036959, WO 2014/100079, WO 2013/019906, WO 2010/077634, and U.S. Pat. Nos. 8,552,154, 8,779,108, and 8,383,796. Specific anti-human PD-L1 mAbs useful as the PD-L1 antagonist in the treatment methods, medicaments and uses of the present invention include, for example without limitation: avelumab (MSB0010718C), nivolumab (BMS-936558), MPDL3280A (an IgG1-engineered, anti-PD-L1 antibody), BMS-936559 (a fully human, anti-PD-L1, IgG4 monoclonal antibody), MEDI4736 (an engineered IgG1 kappa monoclonal antibody with triple mutations in the Fc domain to remove antibody-dependent, cell-mediated cytotoxic activity), and an antibody which comprises the heavy chain and light chain variable regions of SEQ ID NO:24 and SEQ ID NO:21, respectively, of WO 2013/019906.

Other PD-L1 antagonists useful in any of the treatment methods, medicaments and uses of the present invention include an immunoadhesin that specifically binds to PD-L1, and preferably specifically binds to human PD-L1, e.g., a fusion protein containing the PD-L1 binding portion of PD-1 fused to a constant region such as an Fc region of an immunoglobulin molecule.

Table 2 below provides exemplary anti-PD-L1 antibody sequences for use in the treatment methods, medicaments and uses of the present invention.

sections. See, e.g., Thompson, R. H., et al., PNAS 101 (49); 17174-17179 (2004); Thompson, R. H. et al., Cancer Res. 66:3381-3385 (2006); Gadiot, J., et al., Cancer 117:2192-2201 (2011); Taube, J. M. et al., Sci Transl Med 4, 127ra37 (2012); and Toplian, S. L. et al., New Eng. J Med. 366 (26): 2443-2454 (2012).

One approach employs a simple binary end-point of positive or negative for PD-L1 expression, with a positive result defined in terms of the percentage of tumor cells that exhibit histologic evidence of cell-surface membrane staining. A tumor tissue section is counted as positive for PD-L1 expression if at least 1%, and preferably 5% of total tumor cells.

TABLE 2

EXEMPLARY ANTI-HUMAN PD-L1 MONOCLONAL ANTIBODY SEQUENCES

| | |
|---|---|
| Heavy chain CDR1 (CDRH1) | SYIMM (SEQ ID NO :2) |
| Heavy chain CDR2 (CDRH2) | SIYPSGGITFY (SEQ ID NO: 3) |
| Heavy chain CDR3 (CDRH3) | IKLGTVTTVDY (SEQ ID NO: 4) |
| Light chain CDR1 (CDRL1) | TGTSSDVGGYNYVS (SEQ ID NO: 5) |
| Light chain CDR2 (CDRL2) | DVSNRPS (SEQ ID NO: 6) |
| Light chain CDR3 (CDRL3) | SSYTSSSTRV (SEQ ID NO: 7) |
| Heavy chain variable region (VR) | EVQLLESGGGLVQPGGSLRLSCAASGFTFSSYIMMWVRQAPGKGL EWVSSIYPSGGITFYADKGRFTISRDNSKNTLYLQMNSLRAEDTAVY YCARIKLGTVTTVDYWGQGTLVTVSS (SEQ ID NO: 8) |
| Light chain VR | QSALTQPASVSGSPGQSITISCTGTSSDVGGYNYVSWYQQHPGKA PKLMIYDVSNRPSGVSNRFSGSKSGNTASLTISGLQAEDEADYYCS SYTSSSTRVFGTGTKVTVL (SEQ ID NO: 9) |
| Heavy chain | EVQLLESGGGLVQPGGSLRLSCAASGFTFSSYIMMWVRQAPGKGL EWVSSIYPSGGITFYADTVKGRFTISRDNSKNTLYLQMNSLRAEDTA VYYCARIKLGTVTTVDYWGQGTLVTVSSASTKGPSVFPLAPSSKSTS GGTAALGCLVKDYFPEPVTVSWNSGALTSGVHTFPAVLQSSGLYSL SSVVTVPSSSLGTQTYICNVNHKPSNTKVDKKVEPKSCDKTHTCPP CPAPELLGGPSVFLFPPKPKDTLMISRTPEVTCVVVDVSHEDPEVKF NWYVDGVEVHNAKTKPREEQYNSTYRVVSVLTVLHQDWLNGKEYK CKVSNKALPAPIEKTISKAKGQPREPQVYTLPPSRDELTKNQVSLTC LVKGFYPSDIAVEWESNGQPENNYKTTPPVLDSDGSFFLYSKLTVD KSRWQQGNVFSCSVMHEALHNHYTQKSLSLSPGK (SEQ ID NO: 10) |
| Light chain | QSALTQPASVSGSPGQSITISCTGTSSDVGGYNYVSWYQQHPGKA PKLMIYDVSNRPSGVSNRFSGSKSGNTASLTISGLQAEDEADYYCS SYTSSSTRVFGTGTKVTVLGQPKANPTVTLFPPSSEELQANKATLVC LISDFYPGAVTVAWKADGSPVKAGVETTKPSKQSNNKYAASSYLSL TPEQWKSHRSYSCQVTHEGSTVEKTVAPTECS (SEQ ID NO: 11) |

"PD-L1" expression as used herein means any detectable level of expression of PD-L1 protein on the cell surface or of PD-L1 mRNA within a cell or tissue. PD-L1 protein expression may be detected with a diagnostic PD-L1 antibody in an IHC assay of a tumor tissue section or by flow cytometry. Alternatively, PD-L1 protein expression by tumor cells may be detected by PET imaging, using a binding agent (e.g., antibody fragment, affibody and the like) that specifically binds to PD-L1. Techniques for detecting and measuring PD-L1 mRNA expression include RT-PCR and real-time quantitative RT-PCR.

Several approaches have been described for quantifying PD-L1 protein expression in IHC assays of tumor tissue In another approach, PD-L1 expression in the tumor tissue section is quantified in the tumor cells as well as in infiltrating immune cells, which predominantly comprise lymphocytes. The percentage of tumor cells and infiltrating immune cells that exhibit membrane staining are separately quantified as <5%, 5 to 9%, and then in 10% increments up to 100%. For tumor cells, PD-L1 expression is counted as negative if the score is <5% score and positive if the score is ≥5%. PD-L1 expression in the immune infiltrate is reported as a semi-quantitative measurement called the adjusted inflammation score (AIS), which is determined by multiplying the percent of membrane staining cells by the intensity of the infiltrate, which is graded as none (0), mild (score of 1, rare lymphocytes), moderate (score of 2, focal infiltration of tumor by lymphohistiocytic aggregates), or severe (score of 3, diffuse infiltration). A tumor tissue section is counted as positive for PD-L1 expression by immune infiltrates if the AIS is 5.

The level of PD-L1 mRNA expression may be compared to the mRNA expression levels of one or more reference genes that are frequently used in quantitative RT-PCR, such as ubiquitin C.

In some embodiments, a level of PD-L1 expression (protein and/or mRNA) by malignant cells and/or by infiltrating immune cells within a tumor is determined to be "overexpressed" or "elevated" based on comparison with the level of PD-L1 expression (protein and/or mRNA) by an appropriate control. For example, a control PD-L1 protein or mRNA expression level may be the level quantified in nonmalignant cells of the same type or in a section from a matched normal tissue.

"RECIST 1.1 Response Criteria" as used herein means the definitions set forth in Eisenhauer et al., Eur. J Cancer 45:228-247 (2009) for target lesions or nontarget lesions, as appropriate based on the context in which the response is being measured.

"Sustained response" means a sustained therapeutic effect after cessation of treatment with a therapeutic agent, or a combination therapy described herein. In some embodiments, the sustained response has a duration that is at least the same as the treatment duration, or at least 1.5, 2.0, 2.5 or 3 times longer than the treatment duration.

"Tissue Section" refers to a single part or piece of a tissue sample, e.g., a thin slice of tissue cut from a sample of a normal tissue or of a tumor.

"Treat" or "treating" a cancer as used herein means to administer a combination therapy of a PD-L1 antagonist and another therapeutic agent to a subject having a cancer, or diagnosed with a cancer, to achieve at least one positive therapeutic effect, such as for example, reduced number of cancer cells, reduced tumor size, reduced rate of cancer cell infiltration into peripheral organs, or reduced rate of tumor metastasis or tumor growth. Positive therapeutic effects in cancer can be measured in a number of ways (See, W. A. Weber, J. Nucl. Med. 50:1S-10S (2009)). For example, with respect to tumor growth inhibition, according to National Cancer Institute (NCI) standards, a T/C less than or equal to 42% is the minimum level of anti-tumor activity. A T/C<10% is considered a high anti-tumor activity level, with T/C (%)=Median tumor volume of the treated/Median tumor volume of the control ×100. In some embodiments, the treatment achieved by a combination of the invention is any of partial response (PR), complete response (CR), overall response (OR), progression free survival (PFS), disease free survival (DFS) and overall survival (OS). PFS, also referred to as "Time to Tumor Progression" indicates the length of time during and after treatment that the cancer does not grow, and includes the amount of time patients have experienced a CR or PR, as well as the amount of time patients have experienced stable disease (SD). DFS refers to the length of time during and after treatment that the patient remains free of disease. OS refers to a prolongation in life expectancy as compared to naive or untreated subjects or patients. In some embodiments, response to a combination of the invention is any of PR, CR, PFS, DFS, OR, or OS that is assessed using Response Evaluation Criteria in Solid Tumors (RECIST) 1.1 response criteria. The treatment regimen for a combination of the invention that is effective to treat a cancer patient may vary according to factors such as the disease state, age, and weight of the patient, and the ability of the therapy to elicit an anti-cancer response in the subject. While an embodiment of any of the aspects of the invention may not be effective in achieving a positive therapeutic effect in every subject, it should do so in a statistically significant number of subjects as determined by any statistical test known in the art such as the Student's t-test, the chi2-test, the U-test according to Mann and Whitney, the Kruskal-Wallis test (H-test), Jonckheere-Terpstra-test and the Wilcoxon-test.

The terms "treatment regimen," "dosing protocol" and dosing regimen are used interchangeably to refer to the dose and timing of administration of each therapeutic agent in a combination of the invention.

As used herein, "treatment" is an approach for obtaining beneficial or desired clinical results. For purposes of this invention, beneficial or desired clinical results include, but are not limited to, one or more of the following: reducing the proliferation of (or destroying) neoplastic or cancerous cells, inhibiting metastasis of neoplastic cells, shrinking or decreasing the size of tumor, remission of a PD-L1 associated disease (e.g., cancer), decreasing symptoms resulting from a PD-L1 associated disease (e.g., cancer), increasing the quality of life of those suffering from a PD-L1 associated disease (e.g., cancer), decreasing the dose of other medications required to treat a PD-L1 associated disease (e.g., cancer), delaying the progression of a PD-L1 associated disease (e.g., cancer), curing a PD-L1 associated disease (e.g., cancer), and/or prolonging survival of patients having a PD-L1 associated disease (e.g., cancer).

"Ameliorating" means a lessening or improvement of one or more symptoms as compared to not administering a PD-L1 antibody. "Ameliorating" also includes shortening or reducing duration of a symptom.

As used herein, an "effective dosage" or "effective amount" of a drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing incidence or amelioration of one or more symptoms of various PD-L1 associated diseases or conditions (such as for example advanced RCC), decreasing the dose of other medications required to treat the disease, enhancing the effect of another medication, and/or delaying the progression of the PD-L1 associated disease of patients. An effective dosage can be administered in one or more administrations. For purposes of this invention, an effective dosage of a drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

"Tumor burden," also referred to as "tumor load," refers to the total amount of tumor material distributed throughout the body. "Tumor burden" refers to the total number of cancer cells or the total size of tumor(s), throughout the body, including lymph nodes and bone marrow. Tumor burden can be determined by a variety of methods known in the art, such as, e.g., by measuring the dimensions of tumor(s) upon removal from the subject, e.g., using calipers, or while in the body using imaging techniques, e.g., ultrasound, bone scan, computed tomography (CT) or magnetic resonance imaging (MRI) scans.

The term "tumor size" refers to the total size of the tumor which can be measured as the length and width of a tumor. Tumor size may be determined by a variety of methods known in the art, such as, e.g., by measuring the dimensions of tumor(s) upon removal from the subject, e.g., using calipers, or while in the body using imaging techniques, e.g., bone scan, ultrasound, CT or MRI scans.

"Variable regions" or "V region" as used herein means the segment of IgG chains which is variable in sequence between different antibodies. It extends to Kabat residue 109 in the light chain and 113 in the heavy chain.

"VEGFR inhibitor" means a small molecule inhibitor of vascular endothelial growth factor (VEGF) receptor or a monoclonal antibody against vascular endothelial growth factor (VEGF). In an embodiment, a "VEGFR inhibitor" means a small molecule inhibitor of vascular endothelial growth factor (VEGF) receptor. Specific VEGFR inhibitors useful as the VEGFR inhibitor in the treatment methods, medicaments and uses of the present invention include axitinib, sunitinib, sorafenib, tivozanib, and bevacizumab. In an embodiment, specific VEGFR inhibitors useful as the VEGFR inhibitor in the treatment methods, medicaments and uses of the present invention, include axitinib, sunitinib, sorafenib, and tivozanib.

In an embodiment of the treatment methods, medicaments and uses of the present invention, the VEGFR inhibitor is the compound, N-methyl-2-[3-((E)-2-pyridin-2-yl-vinyl)-1H-indazol-6-ylsulfanyl]-benzamide or 6-[2-(methylcarbamoyl) phenylsulfanyl]-3-E-[2-(pyridin-2-yl)ethenyl]indazole, of the following structure:

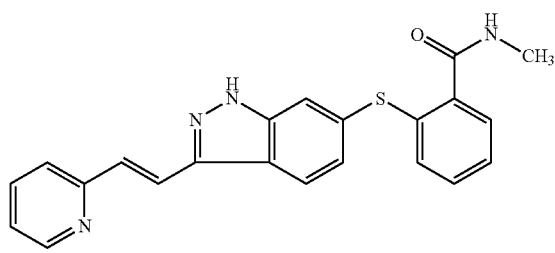 [SMILES: CNC(=O)c1ccccc1Sc1ccc2c(/C=C/c3ccccn3)n[nH]c2c1]

which is known as axitinib or AG-013736.

Axitinib is a potent and selective inhibitor of vascular endothelial growth factor (VEGF) receptors 1, 2 and 3. These receptors are implicated in pathologic angiogenesis, tumor growth, and metastatic progression of cancer. Axitinib has been shown to potently inhibit VEGF-mediated endothelial cell proliferation and survival (Hu-Lowe, D. D., et al., Clin Cancer Res 14: 7272-7283 (2008); Solowiej, S., et al., Biochemistry 48: 7019-31 (2009)). Clinical trials are currently on-going or have been conducted to study the use of axitinib for the treatment of various cancers, including liver cancer, melanoma, mesothelioma, non-small cell lung cancer, prostate cancer, renal cell carcinoma, soft tissue sarcomas and solid tumors. Inlyta® (axitinib) has been approved in the United States, Europe, Japan and other jurisdictions for the treatment of renal cell carcinoma.

Axitinib, as well as pharmaceutically acceptable salts thereof, is described in U.S. Pat. No. 6,534,524. Methods of making axitinib are described in U.S. Pat. Nos. 6,884,890 and 7,232,910, in U.S. Publication Nos. 2006-0091067 and 2007-0203196 and in International Publication No. WO 2006/048745. Dosage forms of axitinib are described in U.S. Publication No. 2004-0224988. Polymorphic forms and pharmaceutical compositions of axitinib are also described in U.S. Publication Nos. 2006-0094763, 2008-0274192 and 2010-0179329 and International Publication No. WO 2013/046133. The patents and patent applications listed above are incorporated herein by reference.

Axitinib is understood to include reference to salts thereof, unless otherwise indicated. Axitinib is basic in nature and capable of forming a wide variety of salts with various inorganic and organic acids. The term "salt(s)," as employed herein, denotes acidic salts formed with inorganic and/or organic acids. Pharmaceutically acceptable salts of axitinib may be formed, for example, by reacting axitinib with an amount of acid, such as an equivalent amount, in a medium such as one in which the salt precipitates or in an aqueous medium followed by lyophilization.

Exemplary acid addition salts of the compound of Formula I include acetates, ascorbates, benzoates, benzenesulfonates, bisulfates, borates, butyrates, citrates, camphorates, camphorsulfonates, fumarates, hydrochlorides, hydrobrom ides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al., Journal of Pharmaceutical Sciences (1977), 66(1) 1-19; P. Gould, International J. of Pharmaceutics (1986), 33 201-217; Anderson et al., The Practice of Medicinal Chemistry (1996), Academic Press, New York; and in The Orange Book (Food & Drug Administration, Washington, D.C., on their website). These disclosures are incorporated herein by reference thereto.

All such acid salts are intended to be pharmaceutically acceptable salts within the scope of axitinib, as used in the present invention and all acid salts are considered equivalent to the free forms of the corresponding compound for purposes of the invention.

Prodrugs of axitinib are also contemplated for use in the methods, medicaments and uses of the present invention. The term "prodrug," as employed herein, denotes a compound that is a drug precursor which, upon administration to a subject, undergoes chemical conversion by metabolic or chemical processes to yield axitinib or a salt thereof. A discussion of prodrugs is provided in T. Higuchi and V. Stella, Pro-drugs as Novel Delivery Systems (1987), 14 of the A.C.S. Symposium Series, and in Bioreversible Carriers in Drug Design (1987), Edward B. Roche, ed., American Pharmaceutical Association and Pergamon Press, both of which are incorporated herein by reference thereto.

The term "4-1BB antibody" as used herein means an antibody, as defined herein, capable of binding to human 4-1BB receptor.

The terms "4-1BB" and "4-1BB receptor" are used interchangeably in the present application, and refer to any form of 4-1BB receptor, as well as variants, isoforms, and species homologs thereof that retain at least a part of the activity of 4-1BB receptor. Accordingly, a binding molecule, as defined and disclosed herein, may also bind 4-1BB from species other than human. In other cases, a binding molecule may be completely specific for the human 4-1BB and may not exhibit species or other types of cross-reactivity. Unless indicated differently, such as by specific reference to human 4-1BB, 4-1BB includes all mammalian species of native sequence4-1BB, e.g., human, canine, feline, equine and bovine. One exemplary human 4-1BB is a 255 amino acid protein (Accession No. NM_001561; NP_001552).

4-1BB comprises a signal sequence (amino acid residues 1-17), followed by an extracellular domain (169 amino acids), a transmembrane region (27 amino acids), and an intracellular domain (42 amino acids) (Cheuk A T C et al., 2004, Cancer Gene Therapy 11: 215-226). The receptor is expressed on the cell surface in monomer and dimer forms and likely trimerizes with 4-1BB ligand to signal.

"4-1BB agonist" as used herein means any chemical compound or biological molecule, as defined herein, which upon binding to 4-1BB, (1) stimulates or activates 4-1BB, (2) enhances, increases, promotes, induces, or prolongs an activity, function, or presence of 4-1BB, or (3) enhances, increases, promotes, or induces the expression of 4-1BB.

4-1BB agonists useful in the any of the treatment methods, medicaments and uses of the present invention include a monoclonal antibody (mAb), or antigen binding fragment thereof, which specifically binds to 4-1BB. Alternative names or synonyms for 4-1BB include CD137 and TNFRSF9. In any of the treatment methods, medicaments and uses of the present invention in which a human individual is being treated, the 4-1BB agonists increase a 4-1BB-mediated response. In some embodiments of the treatment methods, medicaments and uses of the present invention, 4-1BB agonists markedly enhance cytotoxic T-cell responses, resulting in anti-tumor activity in several models.

Human 4-1BB comprises a signal sequence (amino acid residues 1-17), followed by an extracellular domain (169 amino acids), a transmembrane region (27 amino acids), and an intracellular domain (42 amino acids) (Cheuk A T C et al., 2004, Cancer Gene Therapy 11: 215-226). The receptor is expressed on the cell surface in monomer and dimer forms and likely trimerizes with 4-1BB ligand to signal.

Examples of mAbs that bind to human 4-1BB, and useful in the treatment methods, medicaments and uses of the present invention, are described in U.S. Pat. No. 8,337,850 and US 2013-0078240. In some embodiments, an anti-4-1BB antibody useful in the treatment methods, medicaments and uses disclosed herein is a fully humanized IgG2 agonist monoclonal antibody comprising a heavy chain variable region and a light chain variable region comprising the amino acid sequences shown in SEQ ID NO: 18 and SEQ ID NO: 19, respectively.

Table 3A below provides exemplary anti-4-1BB antibody sequences for use in the treatment methods, medicaments and uses of the present invention.

TABLE 3A

EXEMPLARY ANTI-HUMAN 4-1BB MONOCLONAL ANTIBODY SEQUENCES

| | |
|---|---|
| CDRH1 | STYWIS (SEQ ID NO: 12) |
| CDRH2 | KIYPGDSYTNYSPSFQG (SEQ ID NO: 13) |
| CDRH3 | RGYGIFDY (SEQ ID NO: 14) |
| CDRL1 | SGDNIGDQYAH (SEQ ID NO: 15) |
| CDRL2 | QDKNRPS (SEQ ID NO: 16) |
| CDRL3 | ATYTGFGSLAV (SEQ ID NO: 17) |
| Heavy chain VR | EVQLVQSGAEVKKPGESLRISCKGSGYSFSTYWISWVRQMPGKGL<br>EWMGKIYPGDSYTNYSPSFQGQVTISADKSISTAYLQWSSLKASDT<br>AMYYCARGYGIFDYWGQGTLVTVSS (SEQ ID NO: 18) |
| Light chain VR | SYELTQPPSVSVSPGQTASITCSGDNIGDQYAHWYQQKPGQSPVL<br>VIYQDKNRPSGIPERFSGSNSGNTATLTISGTQAMDEADYYCATYT<br>GFGSLAVFGGGTKLTVL (SEQ ID NO: 19) |
| Heavy chain | EVQLVQSGAEVKKPGESLRISCKGSGYSFSTYWISWVRQMPGKGL<br>EWMGKIYPGDSYTNYSPSFQGQVTISADKSISTAYLQWSSLKASDT<br>AMYYCARGYGIFDYWGQGTLVTVSSastkgpsvfplapcsrstsestaalgelvk<br>dyfpepvtvswnsgaltsgvhtfpavlqssglyslssvvtvpssnfgtqtytenvdhkpsntkvd<br>ktverkeevecppepappvagpsvflfppkpkdtlmisrtpevtcvvvdvshedpevqfnwyv<br>dgvevhnaktkpreeqfnstfrvvsvltvvhqdwlngkeykckvsnkglpapiektisktkgqpr<br>epqvytlppsreemtknqvsltclvkgfypsdiavewesngqpennykttppmldsdgsfflys<br>kltvdksrwqqgnvfscsvmhealhnhytqkslslspgk (SEQ ID NO: 20) |
| Light chain | SYELTQPPSVSVSPGQTASITCSGDNIGDQYAHWYQQKPGQSPVL<br>VIYQDKNRPSGIPERFSGSNSGNTATLTISGTQAMDEADYYCATYT<br>GFGSLAVFGGGTKLTVLgqpkaapsvtlfppsseelqankatlvclisdfypgavtva<br>wkadsspvkagvetttpskqsnnkyaassylsltpeqwkshrsyscqvthegstvektvapte<br>cs (SEQ ID NO: 21) |

The term "M-CSF antibody" as used herein means an antibody, as defined herein, capable of binding to human M-CSF receptor.

The terms "M-CSF" and "M-CSF receptor" are used interchangeably in the present application, and refer to any form of M-CSF receptor, as well as variants, isoforms, and species homologs thereof that retain at least a part of the activity of M-CSF receptor. Accordingly, a binding molecule, as defined and disclosed herein, may also bind M-CSF from species other than human. In other cases, a binding molecule may be completely specific for the human M-CSF and may not exhibit species or other types of cross-reactivity. Unless indicated differently, such as by specific reference to human M-CSF, M-CSF includes all mammalian species of native sequence M-CSF, e.g., human, canine, feline, equine and bovine. One exemplary human M-CSF is a 554 amino acid protein (UniProt Accession No. P09603).

"M-CSF antagonist antibody" as used herein means any antibody, as defined herein, which upon binding to M-CSF, inhibits the binding of a M-CSF to c-fms receptor and blocks or prevents activation of c-fms. M-CSF antagonists useful in any of the treatment methods, medicaments and uses of the present invention include a monoclonal antibody (mAb) which specifically binds to M-CSF.

Examples of mAbs that bind to human M-CSF, and useful in the treatment methods, medicaments and uses of the present invention, are described in, for example, U.S. Pat. No. 7,326,414, PCT Patent Application Publication No. WO 2014/167088, and U.S. Patent Application Publication No. 2014-0242071. In some embodiments, an anti-M-CSF antibody useful in the treatment methods, medicaments and uses disclosed herein is a fully human IgG2 antagonist monoclonal antibody comprising a heavy chain variable region and a light chain variable region comprising the amino acid sequences shown in SEQ ID NO: 30 and SEQ ID NO: 31, respectively.

Table 3B below provides exemplary anti-M-CSF antibody sequences for use in the treatment methods, medicaments and uses of the present invention.

TABLE 3B

| EXEMPLARY ANTI-HUMAN M-CSF MONOCLONAL ANTIBODY SEQUENCES | |
|---|---|
| CDRH1 | SFSMT (SEQ ID NO: 24) |
| CDRH2 | YISSRSSTISYADSVKG (SEQ ID NO: 25) |
| CDRH3 | DPLLAGATFFDY (SEQ ID NO: 26) |
| CDRL1 | RASQSVSSSYLA (SEQ ID NO: 27) |
| CDRL2 | GASSRAT (SEQ ID NO: 28) |
| CDRL3 | QQYGSSPLT (SEQ ID NO: 29) |
| Heavy chain VR | MELGLCWVFLVAILEGVQCEVQLVESGGGLVQPGGSLRLSCAASG FTFSSFSMTWVRQAPGKGLEWVSYISSRSSTISYADSVKGRFTISR DNAKNSLYLQMNSLRDEDTAVYYCARDPLLAGATFFDYWGQGTLV TVSSA (SEQ ID NO: 30) |
| Light chain VR | METPAQLLFLLLLWLPDTTGEFVLTQSPGTLSLSPGERATLSCRAS QSVSSSYLAWYQQKPGQAPRLLIYGASSRATGIPDRFSGSGSGTD FTLTISRLEPEDFAVYYCQQYGSSPLTFGGGTKVEIK (SEQ ID NO: 31) |
| Heavy chain | MELGLCWVFLVAILEGVQCEVQLVESGGGLVQPGGSLRLSCAASG FTFSSFSMTWVRQAPGKGLEWVSYISSRSSTISYADSVKGRFTISR DNAKNSLYLQMNSLRDEDTAVYYCARDPLLAGATFFDYWGQGTLV TVSSASTKGPSVFPLAPCSRSTSESTAALGCLVKDYFPEPVTVSWN SGALTSGVHTFPAVLQSSGLYSLSSVVTVPSSNFGTQTYTCNVDHK PSNTKVDKTVERKCCVECPPCPAPPVAGPSVFLFPPKPKDTLMISR TPEVTCVVVDVSHEDPEVQFNWYVDGVEVHNAKTKPREEQFNSTF RVVSVLTVVHQDWLNGKEYKCKVSNKGLPAPIEKTISKTKGQPREP QVYTLPPSREEMTKNQVSLTCLVKGFYPSDIAVEWESNGQPENNY KTTPPMLDSDGSFFLYSKLTVDKSRWQQGNVFSCSVMHEALHNHY TQKSLSLSPGK (SEQ ID NO: 22) |
| Light chain | METPAQLLFLLLLWLPDTTGEFVLTQSPGTLSLSPGERATLSCRAS QSVSSSYLAWYQQKPGQAPRLLIYGASSRATGIPDRFSGSGSGTD FTLTISRLEPEDFAVYYCQQYGSSPLTFGGGTKVEIKRTVAAPSVFIF PPSDEQLKSGTASVVCLLNNFYPREAKVQWKVDNALQSGNSQESV TEQDSKDSTYSLSSTLTLSKADYEKHKVYACEVTHQGLSSPVTKSF NRGEC (SEQ ID NO: 23) |

The term "OX40 antibody" as used herein means an antibody, as defined herein, capable of binding to human OX40 receptor.

The terms "OX40" and "OX40 receptor" are used interchangeably in the present application, and refer to any form of OX40 receptor, as well as variants, isoforms, and species homologs thereof that retain at least a part of the activity of OX40 receptor. Accordingly, a binding molecule, as defined and disclosed herein, may also bind OX40 from species other than human. In other cases, a binding molecule may be completely specific for the human OX40 and may not exhibit species or other types of cross-reactivity. Unless indicated differently, such as by specific reference to human OX40, OX40 includes all mammalian species of native sequence OX40, e.g., human, canine, feline, equine and bovine. One exemplary human OX40 is a 277 amino acid protein (UniProt Accession No. P43489).

"OX40 agonist antibody" as used herein means any antibody, as defined herein, which upon binding to OX40, (1) stimulates or activates OX40, (2) enhances, increases, promotes, induces, or prolongs an activity, function, or presence of OX40, or (3) enhances, increases, promotes, or induces the expression of OX40. OX40 agonists useful in any of the treatment methods, medicaments and uses of the present invention include a monoclonal antibody (mAb) which specifically binds to OX40.

Examples of mAbs that bind to human OX40, and useful in the treatment methods, medicaments and uses of the present invention, are described in, for example, U.S. Pat. No. 7,960,515, PCT Patent Application Publication Nos. WO 2013/028231 and WO 2013/119202, and U.S. Patent Application Publication No. 2015-0190506. In some embodiments, an anti-OX40 antibody useful in the treatment methods, medicaments and uses disclosed herein is a fully human agonist monoclonal antibody comprising a heavy chain variable region and a light chain variable region comprising the amino acid sequences shown in SEQ ID NO: 38 and SEQ ID NO: 39, respectively. In some embodiments, the anti-OX40 antibody is a fully human IgG2 or IgG1 antibody.

Table 3C below provides exemplary anti-OX40 antibody sequences for use in the treatment methods, medicaments and uses of the present invention.

CD20 in the literature include "B-lymphocyte-restricted antigen" and "Bp35." The CD20 antigen is described in Clark et al., *PNAS (USA)* 82:1766 (1985), for example.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the invention. The materials, methods, and examples are illustrative only and not intended to be limiting.

II. Methods, Uses and Medicaments

In one aspect of the invention, the invention provides a method for treating a cancer in a subject comprising admin-

TABLE 3C

EXEMPLARY ANTI-HUMAN OX40 MONOCLONAL ANTIBODY SEQUENCES

| | |
|---|---|
| CDRH1 | SYSMN (SEQ ID NO: 32) |
| CDRH2 | YISSSSSTIDYADSVKG (SEQ ID NO: 33) |
| CDRH3 | ESGWYLFDY (SEQ ID NO: 34) |
| CDRL1 | RASQGISSWLA (SEQ ID NO: 35) |
| CDRL2 | AASSLQS (SEQ ID NO: 36) |
| CDRL3 | QQYNSYPPT (SEQ ID NO: 37) |
| Heavy chain VR | EVQLVESGGGLVQPGGSLRLSCAASGFTFSSYSMNWVRQAPGKG<br>LEWVSYISSSSSTIDYADSVKGRFTISRDNAKNSLYLQMNSLRDEDT<br>AVYYCARESGWYLFDYWGQGTLVTVSS (SEQ ID NO: 38) |
| Light chain VR | DIQMTQSPSSLSASVGDRVTITCRASQGISSWLAWYQQKPEKAPKS<br>LIYAASSLQSGVPSRFSGSGSGTDFTLTISSLQPEDFATYYCQQYNS<br>YPPTFGGGTKVEIK (SEQ ID NO: 39) |
| Heavy chain | EVQLVESGGGLVQPGGSLRLSCAASGFTFSSYSMNWVRQAPGKG<br>LEWVSYISSSSSTIDYADSVKGRFTISRDNAKNSLYLQMNSLRDEDT<br>AVYYCARESGWYLFDYWGQGTLVTVSSastkgpsvfplapcsrstsestaalg<br>clvkdyfpepvtvswnsgaltsgvhtfpavlqssglyslssvvtvpssnfgtqtytcnvdhkpsnt<br>kvdktverkccvecppcpappvagpsvflfppkpkdtlmisrtpevtcvvvdvshedpevqfn<br>wyvdgvevhnaktkpreeqfnstfrvvsvltvvhqdwlngkeykckvsnkglpapiektisktk<br>gqprepqvytlppsreemtknqvsltclvkgfypsdiavewesngqpennykttppmldsdg<br>sfflyskltvdksrwqqgnvfscsvmhealhnhytqkslslspgk (SEQ ID NO: 40) |
| Light chain | DIQMTQSPSSLSASVGDRVTITCRASQGISSWLAVVYQQKPEKAPKS<br>LIYAASSLQSGVPSRFSGSGSGTDFTLTISSLQPEDFATYYCQQYNS<br>YPPTFGGGTKVEIKrtvaapsvfifppsdeqlksgtasvvcllnnfypreakvqwkvdna<br>lqsgnsqesvteqdskdstyslsstltlskadyekhkvyacevthqglsspvtksfnrgec<br>(SEQ ID NO: 41) |

The "CD20" antigen is a ~35 kDa, non-glycosylated phosphoprotein found on the surface of greater than 90% of B cells from peripheral blood or lymphoid organs. CD20 is expressed during early pre-B cell development and remains until plasma cell differentiation. CD20 is present on both normal B cells as well as malignant B cells. Other names for istering to the subject a combination therapy which comprises a PD-L1 antagonist and a VEGFR inhibitor.

In another aspect of the invention, the invention provides a method for treating a cancer in a subject comprising administering to the subject a combination therapy which comprises a PD-L1 antagonist and an anti-4-1BB antibody.

In another aspect of the invention, the invention provides a method for treating a cancer in a subject comprising administering to the subject a combination therapy which comprises a PD-L1 antagonist and an anti-M-CSF antibody.

In another aspect of the invention, the invention provides a method for treating a cancer in a subject comprising administering to the subject a combination therapy which comprises a PD-L1 antagonist and an anti-OX40 antibody.

In another aspect of the invention, the invention provides a method for treating a cancer in a subject comprising administering to the subject a combination therapy which comprises a PD-L1 antagonist, an anti-4-1BB antibody, and an anti-M-CSF antibody.

In another aspect of the invention, the invention provides a method for treating a cancer in a subject comprising administering to the subject a combination therapy which comprises a PD-L1 antagonist, an anti-4-1BB antibody, and an anti-OX40 antibody.

In another aspect of the invention, the invention provides a method for treating a cancer in a subject comprising administering to the subject a combination therapy which comprises a PD-L1 antagonist, an anti-4-1BB antibody, and a CD20 antagonist. In some embodiments, the PD-L1 antagonist is avelumab, the anti-4-1BB antibody is PF-05082566, and the CD20 antagonist is rituximab. In some embodiments, the method comprises a 28-day cycle wherein rituximab is administered on Day 1 of each 28-day cycle at a dose of 375 mg/m$^2$, PF-05082566 is administered on Day 1 or Day 2 at a fixed dose of 100 mg, and avelumab is administered at a dose of 10 mg/kg on Day 2 and Day 15 or 16 of each 28-day cycle. In some embodiments, on Day 2, avelumab is administered at least 3 hours after administration of PF-05082566. In some embodiments, on Day 2, avelumab is administered about 30 minutes after administration of PF-05082566. In some embodiments, on Day 2, avelumab is administered about 60 minutes after administration of PF-05082566.

In another aspect of the invention, the invention provides a method for treating a cancer in a subject comprising administering to the subject a combination therapy which comprises a PD-L1 antagonist, an anti-4-1BB antibody, and azacitidine. In some embodiments, the PD-L1 antagonist is avelumab, and the anti-4-1BB antibody is PF-05082566. In some embodiments, the method comprises a 28-day cycle wherein azacitidine is administered subcutaneously at a daily dose of 75 mg/m$^2$ on Day 1 to Day 7 consecutively of each 28-day cycle, PF-05082566 is administered intravenously at a fixed dose of 100 mg on Day 1 or Day 2, and avelumab is administered at a dose of 10 mg/kg on Day 2 and either Day 15 or Day 16 of each 28-day cycle. In some embodiments, on Day 2, avelumab is administered at least 3 hours after administration of PF-05082566. In some embodiments, on Day 2, avelumab is administered about 30 minutes after administration of PF-05082566. In some embodiments, on Day 2, avelumab is administered about 60 minutes after administration of PF-05082566. In some embodiments, on Day 2, avelumab is administered at least 3 hours after administration of PF-05082566. In some embodiments, on Day 2, avelumab is administered about 30 minutes after administration of PF-05082566. In some embodiments, on Day 2, avelumab is administered about 60 minutes after administration of PF-05082566. In some embodiments, azacitidine is administered at least 3 hours prior to PF-05082566 when dosed on the same day.

In another aspect of the invention, the invention provides a method for treating a cancer in a subject comprising administering to the subject a combination therapy which comprises a PD-L1 antagonist, bendamustine, and a CD20 antagonist. In some embodiments, the PD-L1 antagonist is avelumab, and the CD20 antagonist is rituximab. In some embodiments, the method comprises a 28-day cycle wherein rituximab is administered on Day 1 of each 28-day cycle at a dose of 375 mg/m$^2$, bendamustine is administered intravenously at a dose of 90 mg/m$^2$ on Day 2 and Day 3, and avelumab is administered at a dose of 10 mg/kg on Day 2 and Day 15 or 16 of each 28-day cycle. In some embodiments, the method comprises a 28-day cycle wherein rituximab is administered on Day 1 of each 28-day cycle at a dose of 375 mg/m$^2$, bendamustine is administered intravenously at a dose of 90 mg/m$^2$ on Day 1 and Day 2, and avelumab is administered at a dose of 10 mg/kg on Day 2 and Day 15 or 16 of each 28-day cycle. In some embodiments, on Day 2, avelumab is administered at least 3 hours after administration of bendamustine. In some embodiments, on Day 2, avelumab is administered about 30 minutes after administration of bendamustine. In some embodiments, on Day 2, avelumab is administered about 60 minutes after administration of bendamustine.

In another aspect of the invention, the invention provides a method for treating a cancer in a subject comprising administering to the subject a combination therapy which comprises a PD-L1 antagonist and chemoradiotherapy.

The combination therapy may also comprise one or more additional therapeutic agents. The additional therapeutic agent may be, e.g., a chemotherapeutic other than a VEGFR inhibitor, a biotherapeutic agent (including but not limited to antibodies to VEGF, EGFR, Her2/neu, other growth factor receptors, CD40, CD-40L, CTLA-4, and ICOS), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), a chimeric antigen receptor (CAR)-T cell, and cells transfected with genes encoding immune stimulating cytokines such as but not limited to GM-CSF).

Examples of chemotherapeutic agents include alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelam ines including altretamine, triethylenemelamine, triethylenephosphoramide, triethylenethiophosphoramide and trimethylol melamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g., calicheamicin, especially calicheamicin gamma1I and calicheamicin phill, see, e.g., Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, anthramycin, azaserine, bleomycins, cactinomycin, carabicin, cam inomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum analogs such as carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; and pharmaceutically acceptable salts, acids or derivatives of any of the above.

Each therapeutic agent in a combination therapy of the invention may be administered either alone or in a medicament (also referred to herein as a pharmaceutical composition) which comprises the therapeutic agent and one or more pharmaceutically acceptable carriers, excipients and diluents, according to standard pharmaceutical practice.

Each therapeutic agent in a combination therapy of the invention may be administered simultaneously (i.e., in the same medicament), concurrently (i.e., in separate medicaments administered one right after the other in any order) or sequentially in any order. Sequential administration is particularly useful when the therapeutic agents in the combination therapy are in different dosage forms (one agent is a tablet or capsule and another agent is a sterile liquid) and/or are administered on different dosing schedules, e.g., a chemotherapeutic that is administered at least daily and a biotherapeutic that is administered less frequently, such as once weekly, once every two weeks, or once every three weeks.

In some embodiments, the VEGFR inhibitor or anti-4-1BB antibody is administered before administration of the PD-L1 antagonist, while in other embodiments, the VEGFR inhibitor or anti-4-1BB antibody is administered after administration of the PD-L1 antagonist.

In some embodiments, at least one of the therapeutic agents in the combination therapy is administered using the same dosage regimen (dose, frequency and duration of treatment) that is typically employed when the agent is used as monotherapy for treating the same cancer. In other embodiments, the patient receives a lower total amount of at least one of the therapeutic agents in the combination therapy than when the agent is used as monotherapy, e.g., smaller doses, less frequent doses, and/or shorter treatment duration.

Each small molecule therapeutic agent in a combination therapy of the invention can be administered orally or parenterally, including the intravenous, intramuscular, intraperitoneal, subcutaneous, rectal, topical, and transdermal routes of administration.

A combination therapy of the invention may be used prior to or following surgery to remove a tumor and may be used prior to, during or after radiation therapy.

In some embodiments, a combination therapy of the invention is administered to a patient who has not been previously treated with a biotherapeutic or chemotherapeutic agent, i.e., is treatment-naïve. In other embodiments, the combination therapy is administered to a patient who failed to achieve a sustained response after prior therapy with a biotherapeutic or chemotherapeutic agent, i.e., is treatment-experienced.

A combination therapy of the invention is typically used to treat a tumor that is large enough to be found by palpation or by imaging techniques well known in the art, such as MRI, ultrasound, or CAT scan. In some embodiments, a combination therapy of the invention is used to treat an advanced stage tumor having dimensions of at least about 200 $mm^3$, 300 $mm^3$, 400 $mm^3$, 500 $mm^3$, 750 $mm^3$, or up to 1000 $mm^3$.

In some embodiments, a combination therapy of the invention is administered to a human patient who has a cancer that tests positive for PD-L1 expression. In some embodiments, PD-L1 expression can be detected using a diagnostic anti-human PD-L1 antibody, or antigen binding fragment thereof, in an IHC assay on an FFPE or frozen tissue section of a tumor sample removed from the patient. Typically, the patient's physician would order a diagnostic test to determine PD-L1 expression in a tumor tissue sample removed from the patient prior to initiation of treatment with the PD-L1 antagonist and VEGFR inhibitor, but it is envisioned that the physician could order the first or subsequent diagnostic tests at any time after initiation of treatment, such as for example after completion of a treatment cycle.

Selecting a dosage regimen (also referred to herein as an administration regimen) for a combination therapy of the invention depends on several factors, including the serum or tissue turnover rate of the entity, the level of symptoms, the immunogenicity of the entity, and the accessibility of the target cells, tissue or organ in the subject being treated. Preferably, a dosage regimen maximizes the amount of each therapeutic agent delivered to the patient consistent with an acceptable level of side effects. Accordingly, the dose amount and dosing frequency of each biotherapeutic and chemotherapeutic agent in the combination depends in part on the particular therapeutic agent, the severity of the cancer being treated, and patient characteristics. Guidance in selecting appropriate doses of antibodies, cytokines, and small molecules are available. See, e.g., Wawrzynczak (1996), Antibody Therapy, Bios Scientific Pub. Ltd, Oxfordshire, UK; Kresina (ed.) (1991), Monoclonal Antibodies, Cytokines and Arthritis, Marcel Dekker, New York, N.Y.; Bach (ed.) (1993), Monoclonal Antibodies and Peptide Therapy in Autoimmune Diseases, Marcel Dekker, New York, N.Y.; Baert et al. (2003), New Engl. J. Med. 348:601-608; Milgrom et al. (1999), New Engl. J. Med. 341:1966-1973; Slamon et al. (2001), New Engl. J. Med. 344:783-792; Beniaminovitz et al. (2000), New Engl. J. Med. 342:613-619; Ghosh et al. (2003), New Engl. J. Med. 348:24-32; Lipsky et al. (2000), New Engl. J. Med. 343:1594-1602; Physicians' Desk Reference 2003 (Physicians' Desk Reference, 57th Ed); Medical Economics Company; ISBN: 1563634457; 57th edition (November 2002). Determination of the appropriate dosage regimen may be made by the clinician, e.g., using parameters or factors known or suspected in the art to affect treatment or predicted to affect treatment, and will depend, for example, on the patient's clinical history (e.g., previous therapy), the type and stage of the cancer to be treated and biomarkers of response to one or more of the therapeutic agents in the combination therapy.

Biotherapeutic agents in a combination therapy of the invention may be administered by continuous infusion, or by doses at intervals of, e.g., daily, every other day, three times per week, or one time each week, two weeks, three weeks, monthly, bimonthly, etc. A total weekly dose is generally at least 0.05 μg/kg, 0.2 μg/kg, 0.5 μg/kg, 1 μg/kg, 10 μg/kg, 100 μg/kg, 0.2 mg/kg, 1.0 mg/kg, 2.0 mg/kg, 10 mg/kg, 25 mg/kg, 50 mg/kg body weight or more. See, e.g., Yang et al. (2003), New Engl. J. Med. 349:427-434; Herold et al. (2002), New Engl. J. Med. 346:1692-1698; Liu et al. (1999), J. Neurol. Neurosurg. Psych. 67:451-456; Portielji et al. (2003) Cancer Immunol. Immunother. 52:133-144.

In some embodiments that employ an anti-human PD-L1 mAb as the PD-L1 antagonist in the combination therapy, the dosing regimen will comprise administering the anti-human PD-L1 mAb at a dose of about 1, 2, 3, 5 or 10 mg/kg at intervals of about 14 days (±2 days) or about 21 days (±2 days) or about 30 days (±2 days) throughout the course of treatment.

In other embodiments that employ an anti-human PD-L1 mAb as the PD-L1 antagonist in the combination therapy, the dosing regimen will comprise administering the anti-human PD-L1 mAb at a dose of from about 0.005 mg/kg to about 10 mg/kg, with intra-patient dose escalation. In other escalating dose embodiments, the interval between doses will be progressively shortened, e.g., about 30 days (±2 days) between the first and second dose, about 14 days (±2 days) between the second and third doses. In certain embodiments, the dosing interval will be about 14 days (±2 days), for doses subsequent to the second dose.

In certain embodiments, a subject will be administered an intravenous (IV) infusion of a medicament comprising any of the PD-L1 antagonists described herein.

In some embodiments, the PD-L1 antagonist in the combination therapy is avelumab, which is administered intravenously at a dose selected from the group consisting of: about 1 mg/kg Q2W (Q2W=one dose every two weeks), about 2 mg/kg Q2W, about 3 mg/kg Q2W, about 5 mg/kg Q2W, about 10 mg/kg Q2W, about 1 mg/kg Q3W (Q3W=one dose every three weeks), about 2 mg/kg Q3W, about 3 mg/kg Q3W, about 5 mg/kg Q3W, and about 10 mg/kg Q3W.

In some embodiments of the invention, the PD-L1 antagonist in the combination therapy is avelumab, which is administered in a liquid medicament at a dose selected from the group consisting of about 1 mg/kg Q2W, about 2 mg/kg Q2W, about 3 mg/kg Q2W, about 5 mg/kg Q2W, about 10 mg/kg Q2W, about 1 mg/kg Q3W, about 2 mg/kg Q3W, about 3 mg/kg Q3W, about 5 mg/kg Q3W, and about 10 mg/kg Q3W.

In some embodiments, a treatment cycle begins with the first day of combination treatment and last for 2 weeks. In such embodiments, the combination therapy is preferably administered for at least 12 weeks (6 cycles of treatment), more preferably at least 24 weeks, and even more preferably at least 2 weeks after the patient achieves a CR.

In some embodiments, the 4-1BB agonist in the combination therapy comprises an anti-4-1BB monoclonal antibody comprising heavy chain variable region and a light chain variable region comprising the amino acid sequences shown in SEQ ID NO: 18 and SEQ ID NO: 19, respectively, and is administered in a liquid medicament at a dose selected from the group consisting of 1 mg/kg Q2W, 2 mg/kg Q2W, 3 mg/kg Q2W, 5 mg/kg Q2W, 10 mg/kg Q2W, 1 mg/kg Q3W, 2 mg/kg Q3W, 3 mg/kg Q3W, 5 mg/kg Q3W, and 10 mg/kg Q3W. In some embodiments, the anti-4-1BB monoclonal antibody is administered as a liquid medicament, and the selected dose of the medicament is administered by IV infusion over a time period of about 60 minutes.

In some embodiments, the anti-4-1BB monoclonal antibody is administered at a starting dose of about 0.6 mg/kg Q4W and avelumab is administered at a starting dose of 10 mg/kg Q2W, and if the starting dose combination is not tolerated by the patient, then the dose of avelumab is reduced to 5 mg/kg Q2W and/or the dose of the anti-4-1BB monoclonal antibody is reduced to 0.3 mg/kg Q4W.

In some embodiments, the patient is selected for treatment with the combination therapy of the invention if the patient has been diagnosed with advanced RCC with predominantly clear cell subtype, and the primary tumor has been resected. In some embodiments, the patient has not received prior systemic therapy for advanced RCC.

The present invention also provides a medicament which comprises a PD-L1 antagonist as described above and a pharmaceutically acceptable excipient. When the PD-L1 antagonist is a biotherapeutic agent, e.g., a mAb, the antagonist may be produced in CHO cells using conventional cell culture and recovery/purification technologies.

In some embodiments, a medicament comprising an anti-PD-L1 antibody as the PD-L1 antagonist may be provided as a liquid formulation or prepared by reconstituting a lyophilized powder with sterile water for injection prior to use.

The present invention also provides a medicament which comprises axitinib and a pharmaceutically acceptable excipient.

The anti-PD-L1 and VEGFR inhibitor medicaments described herein may be provided as a kit which comprises a first container and a second container and a package insert. The first container contains at least one dose of a medicament comprising an anti-PD-L1 antagonist, the second container contains at least one dose of a medicament comprising a VEGFR inhibitor, and the package insert, or label, which comprises instructions for treating a patient for cancer using the medicaments. The first and second containers may be comprised of the same or different shape (e.g., vials, syringes and bottles) and/or material (e.g., plastic or glass). The kit may further comprise other materials that may be useful in administering the medicaments, such as diluents, filters, IV bags and lines, needles and syringes. In some embodiments of the kit, the anti-PD-L1 antagonist is an anti-PD-L1 antibody and the instructions state that the medicaments are intended for use in treating a patient having a cancer that tests positive for PD-L1 expression by an IHC assay.

The anti-PD-L1 and anti-4-1BB antibody medicaments described herein may be provided as a kit which comprises a first container and a second container and a package insert. The first container contains at least one dose of a medicament comprising an anti-PD-L1 antagonist, the second container contains at least one dose of a medicament comprising an anti-4-1BB antibody, and the package insert, or label, which comprises instructions for treating a patient for cancer using the medicaments. The first and second containers may be comprised of the same or different shape (e.g., vials, syringes and bottles) and/or material (e.g., plastic or glass). The kit may further comprise other materials that may be useful in administering the medicaments, such as diluents, filters, IV bags and lines, needles and syringes. In some embodiments of the kit, the anti-PD-L1 antagonist is an anti-PD-L1 antibody and the instructions state that the medicaments are intended for use in treating a patient having a cancer that tests positive for PD-L1 expression by an IHC assay.

The anti-PD-L1 antibody and CD20 antagonist medicaments described herein may be provided as a kit which comprises a first container and a second container and a package insert. The first container contains at least one dose of a medicament comprising an anti-PD-L1 antagonist, the second container contains at least one dose of a medicament comprising a CD20 antagonist, and the package insert, or label, which comprises instructions for treating a patient for cancer using the medicaments. The first and second containers may be comprised of the same or different shape (e.g., vials, syringes and bottles) and/or material (e.g., plastic or glass). The kit may further comprise other materials that may be useful in administering the medicaments, such as diluents, filters, IV bags and lines, needles and syringes. In some embodiments of the kit, the anti-PD-L1 antagonist is an anti-PD-L1 antibody and the instructions state that the medicaments are intended for use in treating a patient having a cancer that tests positive for PD-L1 expression by an IHC assay.

These and other aspects of the invention, including the exemplary specific embodiments listed below, will be apparent from the teachings contained herein.

III. General Methods

Standard methods in molecular biology are described Sambrook, Fritsch and Maniatis (1982 & 1989 2nd Edition, 2001 3rd Edition), Molecular Cloning, A Laboratory Manual, Cold Spring Harbor Laboratory Press, Cold Spring Harbor, N.Y.; Sambrook and Russell (2001), Molecular Cloning, 3rd ed., Cold Spring Harbor Laboratory Press, Cold Spring Harbor, N.Y.; Wu (1993), Recombinant DNA, Vol. 217, Academic Press, San Diego, Calif.). Standard methods also appear in Ausbel, et al. (2001), Current Protocols in Molecular Biology, Vols. 1-4, John Wiley and Sons, Inc., New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000), Current Protocols in Protein Science, Vol. 1, John Wiley and Sons, Inc., New York). Chemical analysis, chemical modification, post-translational modification, production of fusion proteins, glycosylation of proteins are described (see, e.g., Coligan, et al. (2000), Current Protocols in Protein Science, Vol. 2, John Wiley and Sons, Inc., New York; Ausubel, et al. (2001), Current Protocols in Molecular Biology, Vol. 3, John Wiley and Sons, Inc., NY, N.Y., pp. 16.0.5-16.22.17; Sigma-Aldrich, Co. (2001), Products for Life Science Research, St. Louis, Mo.; pp. 45-89; Amersham Pharmacia Biotech (2001), BioDirectory, Piscataway, N.J., pp. 384-391). Production, purification, and fragmentation of polyclonal and monoclonal antibodies are described (Coligan, et al. (2001), Current Protocols in Immunology, Vol. 1, John Wiley and Sons, Inc., New York; Harlow and Lane (1999) Using Antibodies, Cold Spring Harbor Laboratory Press, Cold Spring Harbor, N.Y.; Harlow and Lane, supra). Standard techniques for characterizing ligand/receptor interactions are available (see, e.g., Coligan, et al. (2001), Current Protocols in Immunology, Vol. 4, John Wiley, Inc., New York).

Monoclonal, polyclonal, and humanized antibodies can be prepared (see, e.g., Sheperd and Dean (eds.) (2000), Monoclonal Antibodies, Oxford Univ. Press, New York, N.Y.; Kontermann and Dubel (eds.) (2001), Antibody Engineering, Springer-Verlag, N.Y.; Harlow and Lane (1988), Antibodies A Laboratory Manual, Cold Spring Harbor Laboratory Press, Cold Spring Harbor, N.Y., pp. 139-243; Carpenter, et al. (2000), J. Immunol. 165:6205; He, et al. (1998), J. Immunol. 160:1029; Tang et al. (1999), J. Biol. Chem. 274:27371-27378; Baca et al. (1997), J. Biol. Chem. 272: 10678-10684; Chothia et al. (1989), Nature 342:877-883; Foote and Winter (1992), J. Mol. Biol. 224:487-499; U.S. Pat. No. 6,329,511).

An alternative to humanization is to use human antibody libraries displayed on phage or human antibody libraries in transgenic mice (Vaughan et al. (1996), Nature Biotechnol. 14:309-314; Barbas (1995), Nature Medicine 1:837-839; Mendez et al. (1997), Nature Genetics 15:146-156; Hoogenboom and Chames (2000), Immunol. Today 21:371-377; Barbas et al. (2001), Phage Display: A Laboratory Manual, Cold Spring Harbor Laboratory Press, Cold Spring Harbor, N.Y.; Kay et al. (1996), Phage Display of Peptides and Proteins: A Laboratory Manual, Academic Press, San Diego, Calif.; de Bruin et al. (1999), Nature Biotechnol. 17:397-399).

Purification of antigen is not necessary for the generation of antibodies. Animals can be immunized with cells bearing the antigen of interest. Splenocytes can then be isolated from the immunized animals, and the splenocytes can be fused with a myeloma cell line to produce a hybridoma (see, e.g., Meyaard et al. (1997), Immunity 7:283-290; Wright et al. (2000), Immunity 13:233-242; Preston et al., supra; Kaithamana et al. (1999), J. Immunol. 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991), J. Immunol. 146:169-175; Gibellini et al. (1998), J. Immunol. 160:3891-3898; Hsing and Bishop (1999), J. Immunol. 162:2804-2811; Everts et al. (2002), J. Immunol. 168:883-889).

Methods for flow cytometry, including fluorescence activated cell sorting (FACS), are available (see, e.g., Owens, et al. (1994), Flow Cytometry Principles for Clinical Laboratory Practice, John Wiley and Sons, Hoboken, N.J.; Givan (2001), Flow Cytometry, 2nd ed.; Wiley-Liss, Hoboken, N.J.; Shapiro (2003), Practical Flow Cytometry, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probesy (2003), Catalogue, Molecular Probes, Inc., Eugene, Oreg.; Sigma-Aldrich (2003), Catalogue, St. Louis, Mo.).

Standard methods of histology of the immune system are described (see, e.g., Muller-Harmelink (ed.) (1986), Human Thymus: Histopathology and Pathology, Springer Verlag, New York, N.Y.; Hiatt, et al. (2000), Color Atlas of Histology, Lippincott, Williams, and Wilkins, Phila, P A; Louis, et al. (2002), Basic Histology: Text and Atlas, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000), Bioinformatics 16: 741-742; Menne, et al. (2000), Bioinformatics Applications Note 16:741-742; Wren, et al. (2002), Comput. Methods Programs Biomed. 68:177-181; von Heijne (1983), Eur. J. Biochem. 133:17-21; von Heijne (1986), Nucleic Acids Res. 14:4683-4690).

IV. Examples

Example 1: Combination Treatment with Avelumab and Axitinib

This example illustrates a clinical trial study to evaluate safety, efficacy, pharmacokinetics, and pharmacodynamics of avelumab (MSB0010718C) in combination with axitinib (AG-013736) in patients with previously untreated advanced renal cell carcinoma (aRCC).

This study is an open-label, multi-center, multiple-dose trial designed to estimate the maximum tolerated dose (MTD) and select the recommended phase 2 dose (RP2D) of avelumab (MSB0010718C) in combination with axitinib (AG-013736). Once the MTD of avelumab administered in combination with axitinib is estimated (dose finding portion), the dose expansion phase will be opened to further characterize the combination in terms of safety profile, anti-tumor activity, pharmacokinetics, pharmacodynamics and biomarker modulation. Protocol design is set forth in Table 4.

The Dose Finding Phase will estimate the MTD and RP2D in patients with aRCC with clear cell histology who did not receive prior systemic therapy for advanced disease, using the modified toxicity probability interval (mTPI) method. Dose finding will follow an "Up-and-Down" design, with up to 4 potential dose levels (DL) to be tested, shown in Table 4.

The Dose Finding Phase will lead to the identification of an Expansion Test Dose for avelumab in combination with axitinib in patients with aRCC who did not receive prior systemic therapy for their advanced disease. The Expansion Test Dose will either be the MTD (i.e., the highest dose of avelumab and axitinib associated with the occurrence of DLTs in <33% of patients) or the RP2D, i.e., the highest tested dose that is declared safe and tolerable by the investigators and sponsor. Once the Expansion Test Dose is identified, the Dose Expansion Phase will be opened, and avelumab in combination with axitinib will be evaluated in up to approximately 20-40 patients with previously untreated aRCC.

TABLE 4

| Arms | Assigned Interventions |
|---|---|
| Dose finding phase | Group 1: avelumab 10 mg/kg IV Q2W; axitinib 5 mg oral BID<br>Group 2: avelumab 5 mg/kg IV Q2W; axitinib 5 mg oral BID<br>Group 3: avelumab 10 mg/kg IV Q2W axitinib 3 mg oral BID<br>Group 4: avelumab 5 mg/kg IV Q2W; axitinib 3 mg oral BID |
| Dose expansion phase | Group 1: avelumab 10 mg/kg IV Q2W axitinib 5 mg oral BID<br>Group 2: avelumab 5 mg/kg IV Q2W; axitinib 5 mg oral BID<br>Group 3: avelumab 10 mg/kg IV Q2W; axitinib 3 mg oral BID<br>Group 4: avelumab 5 mg/kg IV Q2W; axitinib 3 mg oral BID |

Inclusion Criteria: Histologically or cytologically confirmed advanced RCC with clear cell component. Primary tumor resected. Mandatory archival formalin fixed, paraffin embedded (FFPE) tumor tissue block from primary tumor resection specimen (all patients). For Extension Cohort only, mandatory de novo tumor biopsy from a locally recurrent or metastatic lesion unless obtained from a procedure performed within 6 months of study entry and if the patient has received no intervening systemic anti-cancer treatment. At least one measureable lesion as defined by RECIST version 1.1. Age ≥18 years. Eastern Cooperative Oncology Group (ECOG) performance status 0 or 1. Adequate bone marrow function, renal and liver functions.

The number of patients to be enrolled in the Dose Finding Phase will depend on the observed safety profile, and the number of tested dose levels. Up to approximately 55 patients (including Dose Finding Phase and Dose Expansion Phase) are projected to be enrolled in the study.

Study Treatment: Axitinib will be given orally (PO) twice daily (BID), with or without food, on a continuous dosing schedule. Avelumab will be given as a 1-hour intravenous infusion (IV) every two weeks (Q2W). In all patients, treatment with study drugs may continue until confirmed disease progression, patient refusal, patient lost to follow up, unacceptable toxicity, or the study is terminated by the sponsor, whichever comes first.

In order to mitigate avelumab infusion-related reactions, a premedication regimen of 25 to 50 mg IV or oral equivalent diphenhydramine and 650 mg IV or oral equivalent acetaminophen/paracetamol (as per local practice) may be administered approximately 30 to 60 minutes prior to each dose of avelumab. This may be modified based on local treatment standards and guidelines, as appropriate.

Tumor Assessment: Anti-tumor activity will be assessed by radiological tumor assessments at 6-week intervals, using RECIST version 1.1. Complete and partial responses will be confirmed on repeated imaging at least at 4 weeks after initial documentation. After 1 year from enrollment in the study, tumor assessments should be conducted less frequently, i.e., at 12-week intervals. In addition, radiological tumor assessments will also be conducted whenever disease progression is suspected (e.g., symptomatic deterioration), and at the time of End of Treatment/Withdrawal (if not done in the previous 6 weeks). If radiologic imaging shows progressive disease (PD), tumor assessment should be repeated at least ≥4 weeks later in order to confirm PD.

Brain Computerized Tomography (CT) or Magnetic Resonance Imaging (MRI) scans are required at baseline and when there is a suspected brain metastasis. Bone scan (bone scintigraphy) or 18fluorodeoxyglucose-positron emission tomography/CT (18FDG-PET/CT) are required at baseline, then every 16 weeks only if bone metastases are present at baseline. Otherwise, bone imaging is required only if new bone metastases are suspected. Bone imaging is also required at the time of confirmation of CR for patients who have bone metastases.

Pharmacokinetic/Immunogenicity Assessments: PK/immunogenicity sampling will be collected. To understand the PK effects of avelumab on axitinib, a 7-day lead-in period with single-agent axitinib will be included prior to Cycle 1 in all patients in the Dose Finding Phase and in at least 8 patients in the Dose Expansion Phase of the study. Since avelumab has a long half-life (3-5 days), it would not be feasible to run a lead-in to study the PK of avelumab alone. Therefore, the effect of axitinib on avelumab will be evaluated by comparing avelumab trough concentrations at steady state in the presence of axitinib with those reported for avelumab alone in prior studies.

Biomarker Assessments: A key objective of the biomarker analyses that will be performed in this study is to investigate biomarkers that are potentially predictive of treatment benefit with the combination of avelumab and axitinib. In addition, biomarker studies of tumor and blood biospecimens will be carried out to help further understand the mechanism of action of the avelumab in combination with axitinib, as well as potential mechanisms of resistance.

Tumor biospecimens from archived tissue samples and metastatic lesions will be used to analyze candidate DNA, RNA, or protein markers, or a relevant signature of markers, for their ability to identify those patients who are most likely to benefit from treatment with the study drugs. Markers that may be analyzed include, but are not limited to, PD-L1 expression tumor-infiltrating CD8+ T lymphocytes, and T-cell receptor gene sequence quantitation. Optional tumor biopsies obtained upon disease progression will be used to investigate acquired mechanisms of resistance. Only core needle or excisional biopsies, or resection specimen are suitable.

Peripheral Blood: Specimens will be retained as whole blood, serum, and plasma in a biobank for exploratory biomarker assessments, unless prohibited by local regulation or by decision of the Institutional Review Board or Ethics Committee. Samples may be used to identify or characterize cells, DNA, RNA, or protein markers known or suspected to be of relevance to the mechanisms of action, or the development of resistance to avelumab used in combination with axitinib. These include biomarkers that may aid in the identification of those patients who might preferentially benefit from treatment with avelumab in combination with axitinib, including but not limited to biomarkers related to anti-tumor immune response or target modulation, such as soluble VEGF-A, IL-8, IFNγ and/or tissue FoxP3, PD-1, PD-L2. Biospecimens should be obtained pre-dose and at the same time as PK samples whenever possible.

Example 2: Combination Treatment with Axitinib and Avelumab Versus Sunitinib

This example illustrates a clinical trial study to evaluate safety and efficacy of avelumab (MSB0010718C) in combination with axitinib (AG-013736) and to demonstrate the superiority of this combination versus standard-of-care sunitinib monotherapy in the first-line treatment of patients with advanced RCC (aRCC). Sunitinib malate (SUTENT®) is an oral multitargeted TKI of stem cell receptor factor (KIT), platelet derived growth factor-receptors (PDGFRs), VEG-FRs, glial cell-line neurotrophic factor receptor (RET), and FMS-like tyrosine kinase 3 (FLT3), and colony stimulating factor receptor Type 1 (CSR-1R) approved multinationally for the treatment of aRCC, imatinib-resistant or intolerant gastrointestinal stromal tumor (GIST), and unresectable, well-differentiated metastatic pancreatic neuroendocrine tumors (NET).

The study is a Phase 3, randomized, multination, multicenter, open-label, parallel 2-arm study in which approximately 465 patients are planned to be randomized to receive avelumab in combination with axitinib or sunitinib monotherapy: Arm A: avelumab in combination with axitinib; Arm B: sunitinib. Patients will be stratified according to ECOG performance status (0 versus 1) and LDH (>1.5 ULN vs. ≤1.5 ULN). In arm A (avelumab in combination with axitinib), avelumab will be given as a 1 hour intravenous infusion (IV) every 2 weeks in a 6-week cycle. Axitinib will be given orally (PO) twice daily (BID), with or without food, on a continuous dosing schedule.

Treatment with study drugs may continue until confirmed disease progression, patient refusal, patient lost to follow up, unacceptable toxicity, or the study is terminated by the sponsor, whichever comes first. Axitinib treatment may be adjusted by dosing interruption with or without dose reduction. Intrapatient axitinib dose escalation may occur if the intrapatient escalation criteria are met.

Study Treatment: Axitinib will be given orally twice daily PO on a continuous daily dosing schedule. Avelumab will be given as a 1 hour intravenous infusion every 2 weeks in a 6-week cycle. Sunitinib will be given orally 50 mg taken once daily, on a schedule 4 weeks on treatment followed by 2 weeks off (Schedule 4/2). Patients who develop disease progression on study treatment but are otherwise continuing to derive clinical benefit from study treatment will be eligible to continue with avelumab combined with axitinib, or single-agent avelumab, or single-agent axitinib, or single-agent sunitinib provided that the treating physician has determined that the benefit/risk for doing so is favorable.

Tumor Assessments: Anti-tumor activity will be assessed by radiological tumor assessments and will be based on RECIST guidelines version 1.1 for primary and secondary endpoints and on immune-related RECIST (irRECIST) guidelines for exploratory endpoints. Tumor assessments will be performed every 6 weeks (Q6W) up to 1 year from first dose therapy; thereafter, tumor assessments will be performed every 2 cycles. In addition, radiological tumor assessments will also be conducted whenever disease progression is suspected (e.g., symptomatic deterioration), at the time of the End of Treatment/Withdrawal visit (if not done in the previous 6 weeks), and during the Short term Follow-up period (at the 90-day visit only); subsequent tumor assessments during the Long term Follow-up period can be collected in the absence of withdrawal of consent, regardless of initiation of subsequent anti-cancer therapies.

Tumor assessments will include all known or suspected disease sites. Imaging may include chest, abdomen, and pelvis CT or MRI scans; brain CT or MRI scans (required at baseline and when suspected brain metastasis) and bone scans or 18FDG PET (required at baseline, then every 16 weeks only if bone metastases are present at baseline). Otherwise, bone imaging is required only if new bone metastasis is suspected and at the time of confirmation of complete response for patients who have bone metastases. The CT scans should be performed with contrast agents unless contraindicated for medical reasons. The same imaging technique used to characterize each identified and reported lesion at baseline will be employed in the following tumor assessments. Antitumor activity will be assessed through radiological tumor assessments conducted at baseline, at 6 weeks after the first dose of therapy, then every 6 weeks up to 1 year from the first dose of therapy and every 12 weeks thereafter (if not done in the previous 6 weeks), and during the Short term Follow-up period (at the 90-day visit only); subsequent tumor assessments during the Long term Follow-up period can be collected in the absence of withdrawal of consent, regardless of initiation of subsequent anti-cancer therapies. Further imaging assessments may be performed at any time if clinically indicated (e.g., suspected PD, symptomatic deterioration, etc.). Assessment of response will be made using RECIST version 1.1 and as per immune-related response criteria (irRC) (Nishino 2013). All radiographic images will be collected and may be objectively verified by a BICR independent third-party core imaging laboratory.

Primary Endpoint: Progression-Free Survival (PFS) as assessed by Blinded Independent Central Review (BICR) per RECIST v1.1. Secondary Endpoints: Overall Survival (OS); objective tumor response rate (OR), as assessed by BICR per RECIST version 1.1.; disease Control (DC), as assessed by BICR per RECIST version 1.1.; time to event: time to response (TTR), Duration of Response (DR); adverse Events (AEs) as characterized by type, frequency, severity (as graded by National Cancer Institute Common Terminology Criteria for Adverse Events (NCI CTCAE v.4.03), timing, seriousness, and relationship to study therapy; Laboratory abnormalities as characterized by type, frequency, severity (as graded by NCI CTCAE v.4.03), and timing; PK parameters including trough concentrations (Ctrough) of avelumab and trough concentrations (Ctrough) and maximum concentrations (Cmax) of axitinib; tumor tissue biomarker status (i.e., positive or negative; based on for example, PD-L1 expression and/or quantitation of tumor infiltrating CD8+ T lymphocytes as assessed by immunohistochemistry); measures of clinical outcome (PFS, OS, OR, DCR, DR and TTR) in biomarker-positive and biomarker-negative sub-groups; anti-drug antibodies (ADAs; neutralizing antibodies) of avelumab when in combination with axitinib; patient-Reported Outcomes (PRO): FACT-Kidney Symptom Index (FKSI-19), EuroQol 5 Dimension (EQ 5D).

Example 3: Combination Treatment with Anti-4-1BB Antibody and Avelumab

This example illustrates the therapeutic activity of anti-4-1BB antibody and avelumab combination therapy in murine B16F10 melanoma and MC38 colon carcinoma models.

Six (6)- to 8-week old female C57BL/6 mice were purchased from the Jackson Laboratories. All animals were housed in a pathogen free vivarium facility at Rinat and experiments were conducted according to the protocols in accordance with the Institutional Animal Care and Use Committee (IACUC) guidelines.

The B16F10 melanoma cell line was purchased from American Type Culture Collection (ATCC). The MC38 colon carcinoma cell line was kindly provided by Dr. Antoni Ribas at University of California, Los Angeles, Calif. Cells were cultured in Dulbecco's Modified Eagle's Medium (DMEM) supplemented with 10% fetal bovine serum (FBS), 2 mM L-glutamine at 37° C. in 5% carbon dioxide ($CO_2$), and IMPACT-tested for pathogens at Research Animal Diagnostic Laboratory (RADIL) (Columbia, Mo.). Pathogen-free cells growing in an exponential growth phase were harvested and used for tumor inoculation.

Antibodies used for cell surface or intracellular staining were purchased from BD Biosciences or eBioscience. They were rat anti-mouse CD4-PerCP-Cy5.5 (clone RM4-5, BD Biosciences), rat anti-mouse CD8a-APC-H7 (clone 53-6.7, BD Biosciences), rat anti-mouse CD25-PE-Cy7 (clone PC61, BD Biosciences), rat anti-mouse CD45-BV510 (clone 30-F11, BD Biosciences), rat anti-mouse CD90.2-FITC (clone 53-2.1, BD Biosciences), rat anti-mouse Eomes-PE (clone: Dan11mag, eBioscience), rat anti-mouse FoxP3-eFluor450 (clone FJK-16s, eBioscience), and rat anti-mouse NKp46-BV421 or -AF647 (clone 29A1.4, BD Biosciences). Live cells were separated from dead cells using LIVE/DEAD Fixable Blue Dead Cell Stain Kit (Invitrogen).

Therapeutic mouse anti-mouse 4-1BB mAb (mouse immunoglobulin G1 [mIgG1]), derived from the parental clone MAB9371 (R&D Systems), was prepared in-house. Avelumab was provided by Merck Serono. Isotype control mIgG1 (clone: MOPC-21) was purchased from BioXcell. Human IgG1 was prepared in-house. Anti-4-1BB and avelumab were diluted to concentrations of 0.1 mg/mL and 1 mg/mL, respectively, in phosphate buffered saline (PBS) (Life Technologies), and dosed at 0.2 mL per mouse intraperitoneally (ip) for 3 doses 3 to 4 days apart.

C57BL/6 mice were inoculated subcutaneously at the right flank with $0.2 \times 10^6$ B16F10 or $0.5 \times 10^6$ MC38 cells in 0.1 mL of serum-free DMEM. When tumors reached target size, mice were randomized into treatment groups. Treatment was started on the same day as randomization. Tumor size was measured twice weekly in 2 dimensions using a caliper, and the volume was expressed in cubic millimeters using the formula: $V=0.5 L \times W^2$ where L is the longest diameter of the tumor and W is the diameter perpendicular to L. Body weight was recorded weekly.

Tumors were disseminated into single cell suspension using gentle MACS and Miltenyi Mouse Dissociation Kit (Miltenyi Biotec) according to manufacturer's protocol with modification. Ammonium-Chloride-Potassium (ACK) Lysing Buffer (Life Technologies) was used to remove red blood cells. Cells were washed twice with FACS staining buffer (PBS supplemented with 2% FBS and 0.9% sodium azide [$NaN_3$]), and finally resuspended in FACS staining buffer. An aliquot of cells was pre-incubated with 10 μg/mL of mouse BD Fc Block (BD Biosciences) for 10 minutes before phenotyping mAbs were added to specifically stain immune cells. Cell surface antigens were labeled by incubating cells at 4° C. for 30 minutes. After removing unbound mAbs, cells were washed twice with FACS staining buffer, fixed in fixative buffer (PBS+2% FBS+1% paraformaldehyde), and stored at 4° C. in the dark until analyzed by flow cytometry. Intracellular staining was carried out using Foxp3/Transcription Factor Staining Buffer set (eBioscience) according to the manufacturer's protocol. Flow cytometry data were acquired using LSR Fortessa (BD Biosciences) and analyzed using FlowJo (TreeStar Inc.).

Results were expressed as mean±SEM. Statistical analyses were performed using GraphPad Prism 6.0. One-way or 2-way ANOVA was applied to compare the statistical differences among multiple groups relative to the isotype control. $P<0.05$ was considered as significant difference.

Two murine models were used to evaluate the therapeutic efficacy of anti-4-1BB in combination with avelumab. In the B16F10 melanoma model, the average starting tumor size was 67 to 78 mm³ (range 44 to 114 mm³; n=7 animals per group) (Table 5). By Day 26 post tumor inoculation, the tumors for isotype, anti-4-1BB alone, and avelumab alone groups reached an average of 1206±397 mm³, 1979±425 mm³, and 2112±429 mm³, respectively (Table 5). By contrast, dramatic tumor suppression (average of 341±146 mm³) was observed when animals were administered with anti-4-1BB and avelumab concurrently (p<0.0001 vs single agent alone groups) (Table 5).

TABLE 5

Tumor Measurements (Mean ± SEM) of Subcutaneous B16F10 Melanoma over Time

| Days | Isotypes | | | Anti-4-1BB | | | Avelumab | | | Anti-4-1BB/Avelumab | | |
|---|---|---|---|---|---|---|---|---|---|---|---|---|
| | Mean | SEM | N | Mean | SEM | N | Mean | SEM | N | Mean | SEM | N |
| 13 | 67 | 4 | 7 | 69 | 6 | 7 | 78 | 8 | 7 | 70 | 10 | 7 |
| 17 | 251 | 109 | 7 | 364 | 87 | 7 | 327 | 78 | 7 | 219 | 57 | 7 |
| 20 | 475 | 222 | 7 | 725 | 266 | 7 | 654 | 174 | 7 | 272 | 94 | 7 |
| 24 | 909 | 368 | 7 | 1511 | 417 | 7 | 1304 | 274 | 7 | 243 | 106 | 6 |
| 26 | 1206 | 397 | 7 | 1979 | 425 | 7 | 2112 | 429 | 7 | 341 | 146 | 6 |

Tumor volume is expressed in mm³.
N = Number of animals within each group; SEM = Standard error of the mean.

In the MC38 colon carcinoma model, the average starting tumor size was approximately 60 mm³ (range 41-92 mm³; n=10 animals per group) (Table 6). At the end of study (Day 23 post tumor implantation), the average tumor volumes of isotype, anti-4-1BB alone, avelumab alone, and anti-4-1BB antibody/avelumab combination groups were 1177±252 mm³, 1093±183 mm³, 901±206 mm³, and 530±190 mm³, respectively (Table 6). The reduction in tumor size by the combination treatment was significant, compared to the isotype control (p<0.001) and 4-1BB alone groups (p<0.01), but not to the avelumab group (p>0.05) (Table 6).

TABLE 6

Tumor Measurements (Mean ± SEM) of Subcutaneous MC38 Colon Carcinoma over Time

| Days | Isotypes | | | Anti-4-1BB | | | Avelumab | | | Anti-4-1BB/Avelumab | | |
|---|---|---|---|---|---|---|---|---|---|---|---|---|
| | Mean | SEM | N | Mean | SEM | N | Mean | SEM | N | Mean | SEM | N |
| 7 | 60 | 5 | 10 | 62 | 3 | 10 | 63 | 5 | 10 | 64 | 5 | 10 |
| 10 | 130 | 21 | 10 | 122 | 15 | 10 | 127 | 19 | 10 | 117 | 13 | 10 |
| 14 | 357 | 72 | 10 | 250 | 30 | 10 | 254 | 42 | 10 | 146 | 42 | 10 |
| 16 | 501 | 108 | 10 | 355 | 56 | 10 | 384 | 86 | 10 | 176 | 64 | 10 |
| 18 | 680 | 148 | 10 | 508 | 76 | 10 | 523 | 114 | 10 | 246 | 93 | 10 |
| 21 | 987 | 236 | 9 | 785 | 143 | 10 | 714 | 158 | 9 | 416 | 149 | 10 |
| 23 | 1177 | 252 | 9 | 1093 | 183 | 10 | 901 | 206 | 9 | 530 | 190 | 10 |

Tumor volume is expressed in mm³.
N = Number of animals within each group; SEM = Standard error of the mean.

Figure 2:
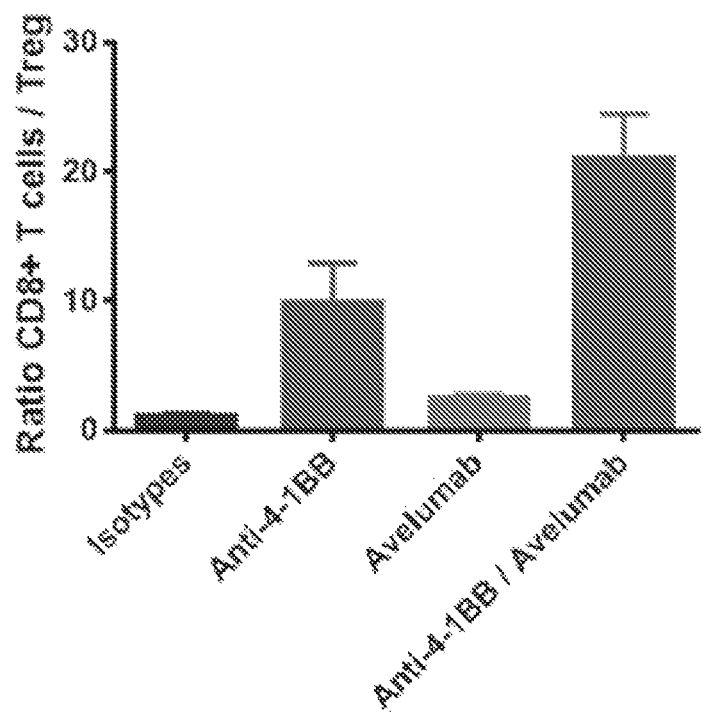
FIG. 2 depicts a graph summarizing the ratio of CD8+ T cells/Treg in response to treatment.
Figure 3:
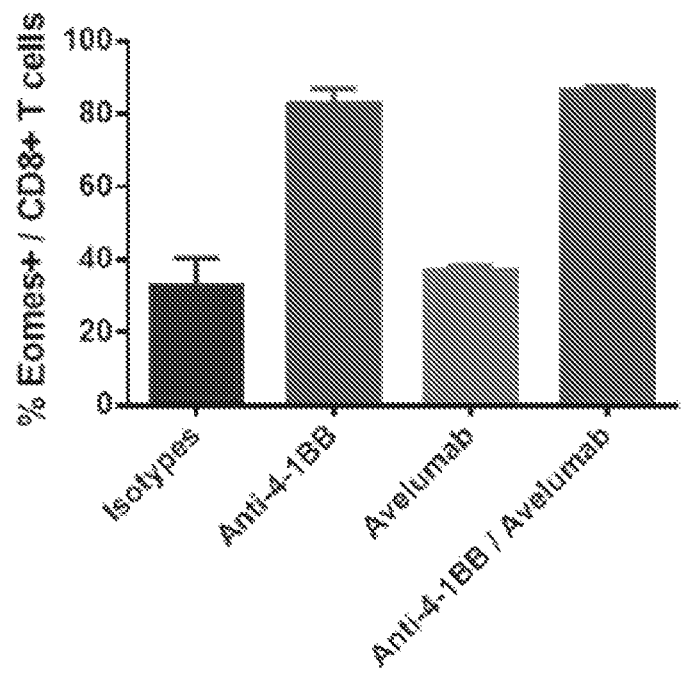
FIG. 3 depicts a graph summarizing Eomes induction in response to treatment.

Tumor-infiltrating lymphocytes (TILs) were isolated from MC38 tumors after treatment and analyzed for markers associated with anti-tumor immune response. The combination treatment facilitated the infiltration of T cells into tumors with an average of 53% of total CD45+ cells, while T-cell frequency (of CD45+ cells) was 25%, 31%, and 36% in the isotype, anti-4-1BB antibody treatment alone, and avelumab alone groups, respectively (FIG. 1). The ratio of CD8+ T cells/regulatory T cell (Treg) in the isotype and avelumab groups was 1.2 and 2.5, respectively. This ratio increased to 10 and 21 in anti-4-1BB antibody treatment alone and in combination with avelumab, respectively (FIG. 2). Furthermore, the induction of Eomes, a marker associated with T-cell effector/memory differentiation, was observed in the anti-4-1BB antibody treatment alone and anti-4-1BB and avelumab combination groups (FIG. 3).

These results demonstrate that treatment with anti-4-1BB antibody in combination with avelumab has a synergistic anti-tumor effect accompanied by the enrichment of T cells in tumor, increased CD8+ T cell/regulatory T cell (Treg) ratio, and induction of eomesodermin (Eomes) expression. Furthermore, the combination therapy elicited an anti-tumor immune response in the tumor microenvironment.

Example 4: Combination Treatment of Advanced Malignancies with Avelumab and PF-05082566

This example illustrates a clinical trial study to evaluate safety, efficacy, pharmacokinetics, and pharmacodynamics of avelumab (MSB0010718C) in combination with PF-05082566, an anti-4-1BB agonist IgG2 antibody, in patients with locally advanced or metastatic solid tumors (e.g., non-small cell lung cancer (NSCLC), melanoma, and squamous cell carcinoma (SCCHN)). Protocol design is set forth in Table 7.

TABLE 7

| Arms | Assigned Interventions |
|---|---|
| Cohort A1: NSCLC patients treated with 10 mg/kg avelumab + 500 mg PF-05082566 | Avelumab 10 mg/kg IV Q2W; PF-05082566 500 mg IV every 4 weeks. Treatment with the combination of avelumab with PF-05082566 will continue until disease progression. |

TABLE 7-continued

| Arms | Assigned Interventions |
|---|---|
| Cohort A2: NSCLC patients treated with 10 mg/kg avelumab + 100 mg PF-05082566 | Avelumab 10 mg/kg IV Q2W; PF-05082566 100 mg IV every 4 weeks. Treatment with the combination of avelumab with PF-05082566 will continue until disease progression. |
| Cohort A3: NSCLC patients treated with 10 mg/kg avelumab + 20 mg PF-05082566 | Avelumab 10 mg/kg IV Q2W; PF-05082566 20 mg IV every 4 weeks. Treatment with the combination of avelumab with PF-05082566 will continue until disease progression. |
| Cohort A4: Melanoma patients treated with 10 mg/kg avelumab + 100 mg PF-05082566 | Avelumab 10 mg/kg IV Q2W; PF-05082566 100 mg IV every 4 weeks. Treatment with the combination of avelumab with PF-05082566 will continue until disease progression. |
| Cohort A5: SCCHN patients treated with 10 mg/kg avelumab + 100 mg PF-05082566 | Avelumab 10 mg/kg IV Q2W; PF-05082566 100 mg IV every 4 weeks. Treatment with the combination of avelumab with PF-05082566 will continue until disease progression. |

Example 5: Combination Treatment of Cancer with Avelumab, Anti-4-1BB Antibody, and Anti-M-CSF Antibody This example illustrates the therapeutic activity of anti-4-1BB antibody, anti-M-CSF antibody, and the anti-PD-L1 antibody Avelumab triple combination therapy in murine MC38 colon carcinoma models.

Six (6)- to 8-week old female C57BL/6 mice were purchased from the Jackson Laboratories. All animals were housed in a pathogen free vivarium facility at Rinat and experiments were conducted according to the protocols in accordance with the Institutional Animal Care and Use Committee (IACUC) guidelines.

The MC38 colon carcinoma cell line was kindly provided by Dr. Antoni Ribas at University of California, Los Angeles, Calif. Cells were cultured in Dulbecco's Modified Eagle's Medium (DMEM) supplemented with 10% fetal bovine serum (FBS), 2 mM L glutamine at 37° C. in 5% carbon dioxide ($CO_2$), and IMPACT-tested for pathogens at Research Animal Diagnostic Laboratory (RADIL) (Columbia, Mo.). Pathogen-free cells growing in an exponential growth phase were harvested and used for tumor inoculation.

Therapeutic mouse anti-mouse 4-1BB mAb (mouse immunoglobulin G1 [mIgG1]), derived from the parental clone MAB9371 (R&D Systems), was prepared in-house. Avelumab was provided by Merck Serono. Rat anti-mouse M-CSF (clone 5A1), rat IgG1 (clone HRPN) and mIgG1 (clone: MOPC-21) isotype controls were purchased from BioXcell. Human IgG1 isotype was prepared in-house. Anti-4-1BB, avelumab and anti-M-CSF mAbs were diluted to concentrations of 0.1 mg/mL and 1 mg/mL, and 1.5 mg/mL, respectively, in phosphate buffered saline (PBS) (Life Technologies), and dosed at 0.2 mL per mouse intraperitoneally (ip) for 3 doses 3 to 4 days apart.

C57BL/6 mice were inoculated subcutaneously at the right flank with 0.5-1×10⁶ MC38 cells in 0.1 mL of DMEM. When tumors reached an average of ~60 mm³ (range 41-93 mm³), mice were randomized into groups of 10 animals per group, and treatment was started at the same day. Tumor size was measured in two dimensions using a caliper, and the volume was expressed in mm³ using the formula: $V=0.5 \, L \times W^2$ where L and W are the long and short diameters of the tumor, respectively. Body weight was recorded weekly.

Results were expressed as mean±SEM (Table 8). Statistical analyses were performed using GraphPad Prism 6.0. One-way or two-way ANOVA was applied to compare the statistical differences among multiple groups relative to isotype controls. P<0.05 was considered as significant difference.

TABLE 8

| Days Post-Tumor Inoculation | Mean Tumor Size (mm³) | SEM | N |
|---|---|---|---|
| Group 1. Isotype control | | | |
| 7 | 60 | 5 | 10 |
| 10 | 130 | 21 | 10 |
| 14 | 357 | 72 | 10 |
| 16 | 501 | 108 | 10 |
| 18 | 680 | 148 | 10 |
| 21 | 987 | 236 | 9 |
| 23 | 1177 | 252 | 9 |
| Group 2. Anti-4-1BB antibody (1 mg/kg) | | | |
| 7 | 62 | 3 | 10 |
| 10 | 122 | 15 | 10 |
| 14 | 250 | 30 | 10 |
| 16 | 355 | 56 | 10 |
| 18 | 508 | 76 | 10 |
| 21 | 785 | 143 | 10 |
| 23 | 1093 | 183 | 10 |
| Group 3. Anti-M-CSF antibody (15 mg/kg) | | | |
| 7 | 58 | 4 | 10 |
| 10 | 138 | 27 | 10 |
| 14 | 196 | 32 | 10 |
| 16 | 268 | 43 | 10 |
| 18 | 350 | 56 | 10 |
| 21 | 432 | 84 | 9 |
| 23 | 572 | 123 | 9 |
| Group 4. Anti-PD-L1 antibody (Avelumab, 10 mg/kg) | | | |
| 7 | 63 | 5 | 10 |
| 10 | 127 | 19 | 10 |
| 14 | 254 | 42 | 10 |
| 16 | 384 | 86 | 10 |
| 18 | 523 | 114 | 10 |
| 21 | 714 | 158 | 9 |
| 23 | 901 | 206 | 9 |
| Group 5. Anti-4-1BB antibody (1 mg/kg) + Anti-PD-L1 antibody (Avelumab, 10 mg/kg) | | | |
| 7 | 64 | 5 | 10 |
| 10 | 117 | 13 | 10 |
| 14 | 146 | 42 | 10 |
| 16 | 176 | 64 | 10 |
| 18 | 246 | 93 | 10 |
| 21 | 416 | 149 | 10 |
| 23 | 530 | 190 | 10 |
| Group 6. Anti-M-CSF antibody (15 mg/kg) + Anti-PD-L1 antibody (Avelumab, 10 mg/kg) | | | |
| 7 | 62 | 4 | 10 |
| 10 | 106 | 10 | 10 |
| 14 | 182 | 29 | 10 |
| 16 | 211 | 32 | 9 |
| 18 | 297 | 65 | 9 |
| 21 | 436 | 112 | 9 |
| 23 | 499 | 145 | 9 |
| Group 7. Anti-4-1BB antibody (1 mg/kg) + Anti-M-CSF antibody (15 mg/kg) + Anti-PD-L1 antibody (Avelumab, 10 mg/kg) | | | |
| 7 | 61 | 4 | 10 |
| 10 | 120 | 16 | 10 |
| 14 | 139 | 15 | 10 |
| 16 | 145 | 20 | 10 |
| 18 | 166 | 20 | 10 |
| 21 | 214 | 28 | 10 |
| 23 | 277 | 39 | 10 |

Treatment with the triple combination of anti-4-1BB antibody, Avelumab, and anti-M-CSF antibody delayed MC38 tumor growth compared to isotype control (Table 8). The triple antibody combination (Table 8, Group 7) was more efficacious than either double combination of avelumab and anti-4-1BB antibody (Table 8, Group 5) or avelumab and anti-CSF-1 antibody (Table 8, Group 6). For example, at day 23 post-tumor inoculation, tumors in animals treated with the triple combination of avelumab, anti-4-1BB antibody, and anti-CSF-1 antibody had a mean size of 277 mm$^3$. In comparison, tumors in animals treated with either the double combination of avelumab and anti-4-1BB antibody or avelumab and anti-CSF-1 antibody had a mean size of 530 mm$^3$ and 499 mm$^3$, respectively, at day 23. Tumors in animals given isotype control had a mean size of 1177 mm$^3$ at day 23. Tumors in animals given anti-4-1BB antibody had a mean size of 1093 mm$^3$ at day 23. Tumors in animals given anti-CSF-1 antibody had a mean size of 572 mm$^3$ at day 23. Tumors in animals given anti-PD-L1 antibody (Avelumab) had a mean size of 901 mm$^3$ at day 23. These results demonstrate that treatment with the triple combination of anti-4-1BB antibody, Avelumab, and anti-M-CSF-antibody is more efficacious in treating cancer than single antibody or double antibody combination treatment.

Example 6: Combination Treatment of Colon Carcinoma with Avelumab, Anti-4-1 BB Antibody, and Anti-OX40 Antibody This example illustrates the therapeutic activity of the anti-PD-L1 antibody Avelumab, anti-4-1 BB antibody, and anti-OX40 antibody triple combination therapy in murine cancer models.

Two murine models were used to evaluate the therapeutic efficacy of combinatorial treatment of anti-OX40 antibody, anti-4-1 BB and Avelumab. Six (6)- to 8-week old female C57BL/6 mice or Balb/C mice were purchased from the Jackson Laboratories. All animals were housed in a pathogen free vivarium facility at Rinat and experiments were conducted according to the protocols in accordance with the Institutional Animal Care and Use Committee (IACUC) guidelines.

The B16F10 melanoma cell line was purchased from American Type Culture Collection (ATCC). The MC38 colon carcinoma cell line was kindly provided by Dr. Antoni Ribas at University of California, Los Angeles, Calif. Cells were cultured in Dulbecco's Modified Eagle's Medium (DMEM) supplemented with 10% fetal bovine serum (FBS), 2 mM L-glutamine at 37° C. in 5% carbon dioxide ($CO_2$). Cells growing in an exponential growth phase were harvested and used for tumor inoculation.

Therapeutic mouse anti-OX40 antibodies with either the mIgG1 or the mIgG2a isotype (anti-OX40 mIgG1 and anti-OX40 mIgG2a, respectively) were derived from parental clone OX86 in house. Therapeutic mouse anti-mouse 4-1BB antibody (mouse immunoglobulin G1 [mIgG1]), derived from the parental clone MAB9371 (R&D Systems), was prepared in-house. Avelumab was provided by Merck Serono. Isotype control mIgG1 (clone: MOPC-21) and mIgG2a (C1.18.4) was purchased from BioXcell. Human IgG1 was prepared in-house. Anti-OX40 antibody, anti-4-1BB antibody, and avelumab were dosed at 3 mg/kg, 1 mg/kg and 20 mg/kg in the B16F10 model and 1 mg/kg, 1 mg/kg and 10 mg/kg in the MC38 model, respectively, in phosphate buffered saline (PBS) (Life Technologies), and dosed at 0.2 mL per mouse intraperitoneally (ip) for 3 doses 3 to 4 days apart.

C57BL/6 mice were inoculated subcutaneously at the right flank with 0.3×10$^6$ B16F10 cells in 0.1 mL of PBS. Balb/C mice were inoculated subcutaneously at the right flank with 0.5×10$^6$ MC38 cells in 0.1 mL of PBS. When tumors reached target size, mice were randomized into treatment groups. Treatment was started on the same day as randomization. Tumor size was measured twice weekly in 2 dimensions using a caliper, and the volume was calculated in cubic millimeters using the formula: V=0.5 L×W$^2$ where L is the longest diameter of the tumor and W is the diameter perpendicular to L. Body weight was recorded weekly.

Results are summarized in Table 9 (B16F10 melanoma) and Table 10 (MC38 colon carcinoma) below (mean tumor size±SEM). Statistical analyses were performed using GraphPad Prism 6.0. 2-way ANOVA was applied to compare the statistical differences among multiple groups relative to the isotype control or other treatment groups. P<0.05 was considered as significant difference. Tumor measurements are in mm$^3$.

TABLE 9

Tumor Measurements of Subcutaneous B16F10 Melanoma over Time

| Days Post-Tumor Inoculation | Mean Tumor Size (mm$^3$) | SEM | N |
|---|---|---|---|
| Group 1. Isotype control | | | |
| 12 | 74 | 11 | 8 |
| 15 | 214 | 46 | 8 |
| 18 | 392 | 67 | 8 |
| 22 | 1015 | 204 | 8 |
| 25 | 1897 | 310 | 8 |
| 29 | 2233 | 249 | 8 |
| 32 | 2311 | 228 | 8 |
| Group 2. Anti-4-1BB antibody | | | |
| 12 | 73 | 9 | 8 |
| 15 | 282 | 67 | 8 |
| 18 | 413 | 98 | 8 |
| 22 | 742 | 155 | 8 |
| 25 | 1392 | 278 | 8 |
| 29 | 2620 | 518 | 8 |
| 32 | 2759 | 493 | 8 |
| Group 3. Anti-OX40 mIgG2a antibody | | | |
| 12 | 71 | 7 | 9 |
| 15 | 198 | 51 | 9 |
| 18 | 370 | 105 | 9 |
| 22 | 783 | 293 | 9 |
| 25 | 1147 | 283 | 9 |
| 29 | 2046 | 433 | 9 |
| 32 | 2576 | 360 | 9 |
| Group 4. Avelumab | | | |
| 12 | 77 | 15 | 5 |
| 15 | 236 | 71 | 5 |
| 18 | 396 | 137 | 5 |
| 22 | 750 | 134 | 5 |
| 25 | 1291 | 210 | 5 |
| 29 | 2159 | 326 | 5 |
| 32 | 2352 | 264 | 5 |
| Group 5. Anti-4-1BB antibody + Anti-OX40 mIgG2a antibody | | | |
| 12 | 78 | 14 | 9 |
| 15 | 155 | 23 | 9 |
| 18 | 313 | 50 | 9 |
| 22 | 595 | 87 | 9 |
| 25 | 861 | 65 | 9 |
| 29 | 1453 | 137 | 9 |
| 32 | 2003 | 245 | 9 |
| Group 6. Anti-OX40 mIgG1 antibody + Avelumab | | | |
| 12 | 76 | 15 | 8 |
| 15 | 228 | 77 | 8 |
| 18 | 336 | 80 | 8 |

TABLE 9-continued

Tumor Measurements of Subcutaneous B16F10 Melanoma over Time

| Days Post-Tumor Inoculation | Mean Tumor Size (mm³) | SEM | N |
|---|---|---|---|
| 22 | 648 | 149 | 8 |
| 25 | 1009 | 248 | 8 |
| 29 | 1381 | 228 | 8 |
| 32 | 1908 | 261 | 8 |
| Group 7. Avelumab + Anti-OX40 mIgG2a antibody | | | |
| 12 | 75 | 11 | 8 |
| 15 | 184 | 37 | 8 |
| 18 | 297 | 61 | 8 |
| 22 | 505 | 111 | 8 |
| 25 | 833 | 191 | 8 |
| 29 | 1731 | 392 | 8 |
| 32 | 2056 | 371 | 8 |
| Group 8. Avelumab + Anti-4-1BB antibody | | | |
| 12 | 73 | 10 | 8 |
| 15 | 229 | 52 | 8 |
| 18 | 274 | 52 | 8 |
| 22 | 537 | 117 | 8 |
| 25 | 803 | 192 | 8 |
| 29 | 1435 | 305 | 8 |
| 32 | 1572 | 307 | 8 |
| Group 9. Avelumab + Anti-4-1BB antibody + Anti-OX40 mIgG1 antibody | | | |
| 12 | 72 | 9 | 9 |
| 15 | 176 | 32 | 9 |
| 18 | 228 | 60 | 9 |
| 22 | 373 | 114 | 9 |
| 25 | 585 | 192 | 9 |
| 29 | 788 | 267 | 9 |
| 32 | 979 | 329 | 9 |
| Group 10. Avelumab + Anti-4-1BB antibody + Anti-OX40 mIgG2a antibody | | | |
| 12 | 74 | 10 | 9 |
| 15 | 104 | 17 | 9 |
| 18 | 120 | 17 | 9 |
| 22 | 155 | 49 | 9 |
| 25 | 208 | 54 | 9 |
| 29 | 365 | 93 | 9 |
| 32 | 442 | 114 | 9 |

TABLE 10

Tumor Measurements of Subcutaneous MC38 Colon Carcinoma over Time

| Days Post-Tumor Inoculation | Mean Tumor Size (mm³) | SEM | N |
|---|---|---|---|
| Group 1. Isotype control | | | |
| 10 | 85 | 7 | 9 |
| 13 | 162 | 23 | 9 |
| 16 | 305 | 41 | 9 |
| 21 | 696 | 66 | 9 |
| 24 | 1064 | 112 | 9 |
| 28 | 1830 | 214 | 9 |
| Group 2. Anti-OX40 mIgG1 antibody | | | |
| 10 | 85 | 6 | 9 |
| 13 | 160 | 15 | 9 |
| 16 | 280 | 28 | 9 |
| 21 | 751 | 79 | 9 |
| 24 | 1238 | 139 | 9 |
| 28 | 2223 | 270 | 9 |
| Group 3. Anti-OX40 mIgG2a antibody | | | |
| 10 | 85 | 7 | 9 |
| 13 | 154 | 11 | 9 |
| 16 | 247 | 18 | 9 |
| 21 | 455 | 64 | 9 |
| 24 | 648 | 102 | 9 |
| 28 | 1053 | 181 | 9 |
| Group 4. Anti-4-1BB antibody | | | |
| 10 | 84 | 7 | 8 |
| 13 | 161 | 11 | 8 |
| 16 | 264 | 19 | 8 |
| 21 | 585 | 37 | 8 |
| 24 | 909 | 65 | 8 |
| 28 | 1494 | 129 | 8 |
| Group 5. Anti-OX40 mIgG1 antibody + Anti-4-1BB antibody | | | |
| 10 | 85 | 7 | 9 |
| 13 | 171 | 11 | 9 |
| 16 | 246 | 20 | 9 |
| 21 | 492 | 27 | 9 |
| 24 | 737 | 62 | 9 |
| 28 | 1241 | 217 | 9 |
| Group 6. Anti-OX40 mIgG2a antibody + Anti-4-1BB antibody | | | |
| 10 | 85 | 7 | 8 |
| 13 | 175 | 15 | 8 |
| 16 | 248 | 29 | 8 |
| 21 | 387 | 74 | 8 |
| 24 | 567 | 119 | 8 |
| 28 | 854 | 163 | 8 |
| Group 7. Anti-4-1BB antibody + Avelumab | | | |
| 10 | 85 | 6 | 9 |
| 13 | 152 | 8 | 9 |
| 16 | 195 | 27 | 9 |
| 21 | 349 | 89 | 9 |
| 24 | 573 | 157 | 9 |
| 28 | 1026 | 255 | 9 |
| Group 8. Anti-OX40 mIgG1 antibody + Anti-4-1BB antibody + Avelumab | | | |
| 10 | 85 | 6 | 9 |
| 13 | 167 | 12 | 9 |
| 16 | 170 | 32 | 9 |
| 21 | 228 | 65 | 9 |
| 24 | 304 | 86 | 9 |
| 28 | 448 | 108 | 9 |
| Group 9. Anti-OX40 mIgG2a antibody + Anti-4-1BB antibody + Avelumab | | | |
| 10 | 85 | 6 | 9 |
| 13 | 153 | 17 | 9 |
| 16 | 127 | 23 | 9 |
| 21 | 116 | 37 | 9 |
| 24 | 165 | 67 | 9 |
| 28 | 260 | 107 | 9 |

Two murine models were used to evaluate the therapeutic efficacy of triple combinatorial treatment of anti-OX40 antibody, anti-4-1BB antibody, and Avelumab. In the B16F10 melanoma model, the average tumor size when treatment was started was 71-78 mm³ (Table 9). By day 32 post tumor inoculation, the tumors in animals treated with isotype control, anti-4-1BB antibody alone, avelumab alone, anti-OX40 mIgG2a antibody alone and anti-OX40 mIgG1 antibody plus Avelumab groups were either very close to or over 2000 mm³; they were 2311±228 mm³, 2759±493 mm³, 2352±264 mm³, 2576±360 mm³ and 1908±261 mm³, respectively. Treatment of animals with anti-4-1BB antibody plus anti-OX40 mIgG2a antibody, anti-OX40 mIgG2a antibody plus Avelumab, or anti-4-1BB antibody plus Avelumab had better treatment efficacy by day 25 as compared to isotype control treated animals; however the difference in tumor size became insignificant on day 32. By contrast, dramatic tumor suppression was observed when animals were administered Avelumab, anti-4-1BB antibody, and anti-OX40 mIgG1 antibody concurrently (Table 9, Group 9), or Avelumab, anti-4-1BB antibody, and anti-OX40 mIgG2a antibody concurrently (Table 9, Group 10). Tumors were 979±329 mm$^3$ (Table 9, Group 9; p<0.001 vs isotype control and single agent alone groups) and 442±114 mm$^3$ (Table 9, Group 10; p<0.00001 vs isotype control and single agent alone groups), respectively. In the case of triple combination with anti-4-1BB antibody, anti-OX40 mIgG2a antibody, and Avelumab combination, it is also significantly better than the double combination groups (p<0.01) (Table 9).

In the MC38 colon carcinoma model, the average tumor size when treatment was started was 84-85 mm$^3$. By day 28 post tumor implantation, tumors in animals treated with anti-OX40 mIgG2a antibody (Table 10, Group 3), anti-OX40 mIgG1 antibody plus anti-4-1BB antibody (Table 10, Group 5), anti-OX40 mIgG2a plus anti-4-1BB antibody (Table 10, Group 6), or anti-4-1BB antibody plus Avelumab (Table 10, Group 7) had tumor sizes of 1053±181 mm$^3$, 1241±217 mm$^3$, 854±163 mm$^3$ and 1026±255 mm$^3$, respectively, which is significantly lower than that of the isotype control treated group (1830±214 mm$^3$) (p<0.001) (Table 10, Group 1). Treatment with anti-OX40 mIgG1 antibody alone (Table 10, Group 2) or anti-4-1BB antibody alone (Table 10, Group 4) did not inhibit tumor growth. By contrast, treatment with the triple combination of anti-4-1BB antibody and Avelumab with either anti-OX40 mIgG1 antibody (Table 10, Group 8) or anti-OX40 mIgG2a antibody (Table 10, Group 9) antibody significantly inhibited tumor growth with the tumor size averaging 448±108 mm$^3$ and 260±107 mm$^3$, respectively. In both cases this is not only significant compared to the isotype control group (p<0.0001), both triple combinations were also significantly better than any of the double combinations (p<0.001) (Table 10).

These results demonstrate that treatment with the triple combination of anti-4-1BB antibody, Avelumab, and anti-OX40 antibody is more efficacious in treating cancer than single antibody or double antibody combination treatment.

Example 7: Combination Treatment of Relapsed or Refractory (R/R) Diffuse Large B-Cell Lymphoma (DLBCL) with Avelumab in Combination with Anti-4-1BB Antibody, Azacitidine, Anti-CD20 Antagonist Antibody, and/or Conventional Chemotherapy (Bendamustine)

In this study example, three treatment regimens are illustrated:
Avelumab in combination with rituximab and PF-05082566 for the treatment of patients with relapsed or refractory DLBCL;
Avelumab in combination with azacitidine and PF-05082566 for the treatment of patients with relapsed or refractory DLBCL; and
Avelumab in combination with rituximab and bendamustine is indicated for the treatment of patients with relapsed or refractory DLBCL.

The target population for the study is patients with R/R DLBCL defined as follows: (i) patients with R/R DLBCL following failure of at least 2 lines (and a maximum of 4 lines) of prior rituximab/multi-agent chemotherapy and/or (ii) failure of ASCT, or (iii) who are not candidates for ASCT (refusal or no available donor), or (iv) who are not candidates for intensive second-line chemotherapy.

The current NCCN Guidelines (version 1.2016) for DLBCL recommend treatment with rituximab, cyclophosphamide, doxorubicin, vincristine, and prednisone (R-CHOP) in patients with newly diagnosed disease in all stages of disease, or mini-CHOP in patients >80 years with comorbidities. Approximately 60% of patients with DLBCL are expected to be cured following treatment with R-CHOP. Thirty to 50% of those with advanced disease will, however, have disease that is either primary refractory (~15%) or resistant (~25%) to R-CHOP (NCCN Guidelines, 2016; Sehn & Gascoyne, 2015; Vacirca et al., 2014).

High-dose chemotherapy followed by ASCT provides the best chance of a cure in patients with R/R DLBCL in the second-line setting; however, due to advanced age and/or comorbidities, only approximately 50% of patients for whom first-line R-CHOP fails are fit for high-dose chemotherapy, and of these, only about ~50% have chemosensitive disease in the second-line setting and are suitable for ASCT (Sehn & Gascoyne, 2015). Even if eligible for high-dose chemotherapy, patients may refuse ASCT, lack a good donor, or be ineligible due to a variety of comorbidities. Even in patients treated with high-dose chemotherapy followed by ASCT, only a minority (<10%) are cured.

The following rituximab-containing chemotherapy regimens are currently recommended by the NCCN Guidelines (version 1.2016) for second-line salvage therapy and beyond in patients who are not eligible for high-dose chemotherapy and ASCT: bendamustine±rituximab, brentuximab, cyclophosphamide/etoposide/procarbazine/prednisone (CEPP), cyclophosphamide/etoposide/vincristine/prednisone (CEOP), dose-adjusted etoposide, prednisone, vincristine, cyclophosphamide and doxorubicin (DA-EPOCH)±rituximab, gemcitabine, dexamethasone and cisplatin (GDP) ±rituximab, gemcitabine/oxaliplatin±rituximab, lenalidomide±rituximab, and rituximab (NCCN Guidelines, 2016).

The outcome of patients for whom treatment with R-CHOP fails, and who are not eligible for high-dose chemotherapy or ASCT, is dismal, with a median PFS of 3.6 months (Vacirca et al., 2014). The treatment options for these patients remain very limited, and there is consequently a high unmet medical need in patients with R/R DLBCL for the development of more effective salvage strategies that can prolong PFS and overall survival (OS).

The proposed Study is a multicenter, international, parallel design, randomized, open-label, 2-component (Phase 1b followed by Phase 3) study of avelumab in various combinations for the treatment of R/R DLBCL. Agents that will be tested include:

(i) PF-05082566, a novel fully human IgG2 monoclonal antibody agonist of 4-1BB, (ii) Azacitidine, a DNA methyltransferase inhibitor (DNMTi) and epigenetic agent which has been shown to have potential immune priming activity through various mechanisms including the induction of PD-1 on tumor infiltrating lymphocytes (TILs) and PD-L1 on tumor cells as well as the induction of tumor neo-antigen expression, (iii) Rituximab, a CD20 antagonist antibody, and (iv) Bendamustine, an alkylating chemotherapy agent which is one of the National Comprehensive Cancer Network (NCCN) recommended agents for the salvage therapy of patients with DLBCL who are ineligible for high dose chemotherapy and autologous stem cell transplant (ASCT).

The treatment regimens proposed in the study include avelumab combined with:
(i) Rituximab and PF-05082566,
(ii) Azacitidine and PF-05082566, and
(iii) Rituximab and bendamustine.

In Phase 3, patients will be randomized in a 1:1 ratio to the treatment regimen selected in Phase 1b versus the Investigator's Choice standard of care (SOC) treatment to determine whether the selected treatment regimen is superior to the Investigator's Choice SOC treatment in prolonging progression-free survival (PFS).

The target study population of this Phase 1 b/Phase 3 registrational study will comprise patients with R/R DLBCL who have completed at least 2 (but not more than 4) lines of prior rituximab/multi-agent chemotherapy, or in whom ASCT has been a failure, or who are not candidates for ASCT, or who are not eligible for intensive chemotherapy. The study will assess the safety, efficacy, pharmacokinetics (PK), immunogenicity, and patient reported outcomes.

The primary objective of the Phase 1 b component is to make a preliminary assessment of safety for each combination regimen. Each arm without a significant safety signal among the first 6 patients will then be expanded to a total of 28 patients per arm in order to select a treatment regimen to be advanced to the Phase 3 component of the study. This decision will be based upon the investigator observed objective response rate (ORR) and safety profile of each combination regimen. The combination regimens to be assessed in the Phase 1 b component of the study in 28-day cycles include:

Arm A: Avelumab/Rituximab/PF-05082566 (4-1BB)

(i) Rituximab 375 mg/m$^2$ (IV) in the morning on Day 1 of each 28-day cycle. Rituximab is administered for a maximum of 8 cycles.

Rituximab will be administered at least 3 hours prior to PF-05082566 when dosed on the same day.

(ii) PF-05082566 100 mg fixed dose (IV) in the morning on Day 2 of Cycles 1 and 2 of each 28-day cycle. If PF-05082566 is well tolerated in Cycles 1 and 2, administration of PF-05082566 may be on Day 1 in Cycle 3 (and all subsequent cycles).

PF-05082566 will be administered at least 3 hours prior to avelumab in Cycle 1. If PF-05082566 is well tolerated in Cycle 1, in Cycle 2 and all subsequent cycles the window of dose administration between PF-05082566 and avelumab may be decreased from at least 3 hours apart to 30-60 minutes apart.

(iii) Avelumab 10 mg/kg (IV) every 2 weeks on Day 2 and Day 16 of each 28-day cycle in Cycle 1 and Cycle 2. If avelumab is well tolerated in Cycle 1 and 2, administration of avelumab may be on Day 1 and Day 15 in Cycle 3 (and all subsequent cycles).

Avelumab will be administered at least 3 hours after PF-05082566 in Cycle 1 and Cycle 2. If avelumab is well tolerated in Cycle 1 Day 2, in Cycle 2 Day 2 and subsequent cycles the window of dose administration between avelumab and PF-05082566 may be decreased from at least 3 hours apart to 30-60 minutes apart.

Arm B: Avelumab/Azacitidine/PF-05082566 (4-1BB)

(i) Azacitidine 75 mg/m$^2$ (SC) in the morning on Day 1-Day 7 consecutively of each 28-day cycle. Azacitidine is administered for a maximum of 6 cycles.

Azacitidine will be administered at least 3 hours prior to PF-05082566 when dosed on the same day.

(ii) PF-05082566 100 mg fixed dose (IV) in the morning on Day 2 for Cycle 1 and Cycle 2, of each 28-day cycle. If PF-05082566 is well tolerated in Cycle 1 and 2, PF-05082566 may be administered on Day 1 commencing with Cycle 3 (and subsequent cycles).

PF-05082566 should be administered at least 3 hours prior to avelumab administration. If PF-05082566 is well tolerated in Cycle 1, in Cycle 2 and all subsequent cycles the window of dose administration between PF-05082566 and avelumab may be decreased from at least 3 hours apart to 30-60 minutes apart.

(iii) Avelumab 10 mg/kg every 2 weeks (IV) on Day 2 and Day 16 of each 28-day cycle in Cycle 1 and Cycle 2. If avelumab is well tolerated in Cycle 1 and 2, avelumab may be administered on Day 1 and Day 15 in Cycle 3 (and all subsequent cycles).

Avelumab administration should be at least 3 hours after PF-05082566 in Cycle 1 and Cycle 2. If avelumab is well tolerated in Cycle 1 Day 2, in Cycle 2 Day 2 and subsequent cycles the window of dose administration between avelumab and PF-05082566 may be decreased from at least 3 hours apart to 30-60 minutes apart.

Arm C: Avelumab/Bendamustine/Rituximab (i) Rituximab 375 mg/m$^2$ (IV) in the morning on Day 1 of each 28-day cycle. Rituximab is administered for a maximum of 8 cycles.

(ii) Bendamustine 90 mg/m$^2$ (IV) on Day 2 and Day 3 of each 28-day cycle in Cycle 1 and Cycle 2. If bendamustine is well tolerated in Cycles 1 and 2, bendamustine may be administered on Day 1 and Day 2 in Cycle 3 (and all subsequent cycles). Bendamustine is administered for a maximum of 6 cycles.

(iii) Avelumab 10 mg/kg every 2 weeks (IV) on Day 2 and Day 16 of each 28-day cycle in Cycle 1 and Cycle 2. If avelumab is well tolerated in Cycles 1 and 2, avelumab may be administered on Day 1 and Day 15 in Cycle 3 (and all subsequent cycles). Avelumab administration should be at least 3 hours after bendamustine.

In Phase 3 (N=220), the primary objective is to demonstrate superiority in PFS (as assessed by Blinded Independent Central Review [BICR]) of the combination regimen identified in Phase 1 b, over the control treatment, namely Investigator's Choice SOC chemotherapy (comprising rituximab/bendamustine or rituximab/gemcitabine/oxaliplatin).

The following treatment regimens will be assessed in the Phase 3 component of the study, with all treatments being administered in 28-day cycles:

Arm D (N=110): Regimen Selected from Phase 1 b.

Arm D will be one of the treatment regimens assessed in Phase 1 b, i.e., Arm A, B, or C, selected based on safety and efficacy assessments.

Cohort E (N=110): Investigator's Choice Option Between the Following Standard of Care Regimens:
(i) Rituximab/bendamustine
Rituximab 375 mg/m$^2$ IV Day 1
Bendamustine 120 mg/m$^2$ IV Day 1 and Day 2
(ii) Rituximab/gemcitabine/oxaliplatin
Rituximab 375 mg/m$^2$ IV Day 1
Gemcitabine 1000 mg/m$^2$ IV on Day 2 and Day 17
Oxaliplatin 100 mg/m$^2$ IV on Day 2 and Day 17

Example 8: Combination Treatment of Patients with Advanced Malignancies Whose Disease has Progressed on an Immune Checkpoint Inhibitor with Avelumab in Combination with anti-4-1BB Antibody This example illustrates a Phase 2 study to assess safety and efficacy of avelumab (MSB0010718C) in combination with anti-4-1BB agonist antibody PF-05082566 in patients with advanced NSCLC, RCC, or urothelial cancer (UC) whose disease has progressed on prior therapy(ies), including a single-agent immune checkpoint inhibitor.

The objective of this study is to evaluate the Objective Response Rate (ORR) based on RECIST 1.1 of avelumab plus PF-05082566. Patients must have advanced NSCLC, RCC, or urothelial cancer which was resistant (responded and then progressed) or refractory (never responded) to prior therapy(ies), including a single-agent immune checkpoint inhibitor (e.g., anti-PD-1/anti-PD-L1 or anti-CTLA-4).

Avelumab will be given as a 1-hour intravenous infusion every 2 weeks at a dose of 10 mg/kg in all three cohorts. PF-05082566 will be administered at 100 mg as a 1-hour IV infusion once every 4 weeks on Day 1 of each cycle.

On days when both drugs are administered, PF 05082566 will be administered first, followed by the avelumab infusion no more than 30 minutes after the end of the PF-05082566 infusion.

Dosing will continue until disease progression is confirmed by the investigator, patient refusal, unacceptable toxicity, patient is lost to follow-up, or until the study is terminated by the Sponsor, whichever occurs first.

The combination of avelumab plus anti-4-1BB antibody PF-05082566 and anti-OX40 antibody PF-04518600 has been evaluated for cytokine release using the standard human PBMC in vitro test. The cytokine release assay was completed for PF-05082566 alone and in combination with avelumab and PF-04518600. Results for the PF-05082566 antibody alone did not show a significant increase in cytokine release. In addition, there was no additive effect on cytokine release when the three monoclonal antibodies were combined.

ORR estimation will be the primary objective in any potential evaluation of avelumab in combination with immunotherapy other than PF-05082566. In each case, the ORR will be evaluated with the totality of the data for potential cohort expansion or testing of multiple tumor types and/or other combination immunotherapeutic agents.

Example 9: Randomized, Phase 3 Study of Avelumab (MSB0010718C) in Combination with Standard of Care Chemoradiotherapy (Cisplatin and Definitive Radiation Therapy) Versus Standard-of-Care Chemoradiotherapy in the Front-Line Treatment of Patients with Locally Advanced Squamous Cell Carcinoma of the Head and Neck This example illustrates a Phase 3, multicenter, multinational, randomized, placebo controlled study of avelumab (MSB0010718C) in combination with standard of care (SOC) chemoradiotherapy (cisplatin and definitive radiation therapy) versus SOC chemotherapy for front-line treatment of patients with locally-advanced squamous cell carcinoma of the head and neck.

Approximately 640 patients who have received no prior therapy for their SCCHN (oral cavity, oropharynx, larynx, or hypopharynx) HPV−: Stage III, IVa, or IVb or HPV+: T4 or N3 who are eligible for definitive chemoradiotherapy with cisplatin will be randomized 1:1 to treatment with avelumab+SOC chemoradiotherapy vs. placebo+chemoradiotherapy followed by maintenance avelumab or placebo for up to 1 year. Patients will be stratified based on:
Tumor (T) stage (<T4 vs T4);
Nodal (N) stage (N0 vs N1/N2a/N2b vs N2c/N3)

Tumor assessment will occur every 12 weeks following the completion of definitive chemoradiotherapy for 2 years, and then every 16 weeks thereafter.

A blinded independent review committee (BICR) will review tumor assessments in addition to investigator reviews.

When the study treatment is discontinued for reasons other than progressive disease (PD), patient withdrawal of consent, or death, patients will be followed and have tumor assessments performed every 12 weeks until: 1) PD, 2) death, 3) patient withdrawal of consent from study, or 4) 2 years from completion of chemoradiotherapy have passed after which tumor assessments can be every 16 weeks, whichever occurs first.

Arm A: Avelumab (MSB0010718C)+SOC Chemoradiotherapy (CRT).
In this study, the lead-in phase is to start seven days prior to initiation of the CRT phase.
The maintenance phase will start after completion of the CRT phase (i.e., two weeks following completion of CRT).
Cisplatin 100 mg/m$^2$ Days 1, 22, 43. Administered in 500 ml normal saline over a 60-120 minute infusion with an additional 1 to 1.5 L of fluid given post-hydration.
Radiation therapy (RT) 70 Gy/33-35 fractions/day, 5 fractions/week intensity modulated radiation therapy (IMRT).
Avelumab: 10 mg/kg administered on Day 1 of the lead-in phase' and Days 8, 29, 39 of the CRT phase, and every 2 weeks (Q2W) thereafter for up to 12 months.
Arm B: SOC Chemoradiotherapy.
Cisplatin 100 mg/m$^2$ Days 1, 22, 43.
RT 70 Gy/33-35 fractions/day, 5 fractions/week IMRT.
Placebo: Day 1 of the lead-in phase, Days 8, 29, 39 of the CRT phase, and Q2W thereafter for up to 12 months.
Avelumab and placebo will be administered as IV infusion.

Patients will receive study treatment until: 1) 12 months after start of maintenance therapy (study intervention completion), 2) PD, 3) death, 4) patient withdrawal of consent, 5) patient is lost to follow-up, 6) unacceptable toxicity occurs, or 7) the study is terminated by the Sponsor, whichever occurs first.

The dose of cisplatin may be modified on Days 22 and/or 43 for toxicity as follows: starting dose level is 100 mg/m$^2$, dose level-1 is 75 mg/m$^2$, and dose level-2 is 50 mg/m$^2$.

Peripheral blood and additional tumor tissue biomarkers consisting of the levels of cells, deoxyribonucleic acid (DNA), ribonucleic acid (RNA), or proteins that may be related to anti-tumor immune response and/or response to or disease progression on avelumab, such as genes related to IFN-γ or transforming growth factor (TGF)-β.

Example 10: Phase 1b Dose-Finding Study of Avelumab (MSB0010718C; Anti-PD-L1)+Axitinib in Treatment-Naïve Patients with Advanced Renal Cell Carcinoma This example illustrates results from the study described in Example 1 above. Eligible patients have histologically confirmed aRCC with a clear-cell component, primary tumour resection, measurable lesion, archival/fresh tumour biopsy, ECOG PS≤1, no preexisting uncontrolled hypertension, and no prior systemic therapy for aRCC. To determine dose modifications for future cohorts, dose escalation/de-escalation rules that follow the modified toxicity probability interval method were used. Adverse events (AEs) were graded by NCI CTCAE v4. Objective response rates (ORR; RECIST v1.1) were evaluated.

The starting dose of avelumab 10 mg/kg (1 h IV infusion) Q2W+axitinib 5 mg PO BID met MTD criteria. By 5 Apr. 2016, 6 patients (median age 59.5 [range, 45-73]) have been treated with avelumab for a median of 17.0 wks (range, 11.9-21.7) and with axitinib for 16.3 wks (range, 12.7-22.7). One DLT of grade 3 proteinuria occurred. The most common treatment-related (TR) AEs of any grade were dysphonia (n=4), hypertension (n=4), fatigue (n=3), and headache (n=3). Grade 3-4 TRAEs were hypertension (n=2), hand-foot syndrome (n=1), elevated lipase (n=1), and proteinuria (n=1). Confirmed ORR is 83.3% (95% CI: 35.9, 99.6) based on 5 PRs and stable disease in 1 patient.

The MTD/RP2D for this expansion phase and further studies in aRCC has been confirmed as avelumab 10 mg/kg IV Q2W+axitinib 5 mg PO BID continuously. The regimen has shown preliminary antitumour activity in treatment-naïve patients with aRCC. Enrollment is ongoing in the expansion cohort. These results demonstrate the efficacy and safety of avelumab +axitinib vs current monotherapies for aRCC.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

It is claimed:

1. A method for treating a cancer in a human subject comprising administering to the subject a combination therapy which comprises an antagonist of a Programmed Death Ligand 1 protein (PD-L1) and a VEGFR inhibitor, wherein the PD-L1 antagonist is an anti-PD-L1 monoclonal antibody comprising: three CDRs from a heavy chain variable region comprising the amino acid sequence shown in SEQ ID NO: 8, and three CDRs from a light chain variable region comprising the amino acid sequence shown in SEQ ID NO: 9, wherein the VEGFR inhibitor is N-methyl-2-[3-((E)-2-pyridin-2-yl-vinyl)-1H-indazol-6-ylsulfanyl]-benzamide or a pharmaceutically acceptable salt thereof and wherein the cancer is renal cell carcinoma.

2. The method of claim 1, wherein the PD-L1 antagonist is avelumab and the VEGFR inhibitor is axitinib.

3. The method of claim 2, wherein the PD-L1 antagonist is administered as an initial dose of at least about 5 mg/kg, or about 10 mg/kg; and the VEGFR inhibitor is administered as an initial dose of at least 3 mg or 5 mg.

4. The method of claim 3, wherein the PD-L1 antagonist is administered about once every two weeks; and the VEGFR inhibitor is administered twice daily.

5. The method of claim 1, wherein the renal cell carcinoma is advanced renal cell carcinoma.

6. The method of claim 5, wherein the advanced renal cell carcinoma is previously untreated advanced renal cell carcinoma.

7. The method of claim 2, wherein the PD-L1 antagonist is administered about once every two weeks.

8. The method of claim 7, wherein the PD-L1 antagonist is administered at a dose of about 10 mg/kg.

9. The method of claim 2, wherein the VEGFR inhibitor is administered twice daily.

10. The method of claim 9, wherein the VEGFR inhibitor is administered at a dose of 5 mg.

11. The method of claim 2, wherein the PD-L1 antagonist is administered as a 1-hour intravenous infusion.

12. The method of claim 2, wherein administration of the PD-L1 antagonist and the VEGFR inhibitor is discontinued if unacceptable toxicity occurs.

13. The method of claim 2, wherein administration of the PD-L1 antagonist and the VEGFR inhibitor is discontinued if disease progression occurs.

14. A method for treating renal cell carcinoma in a human subject comprising administering to the subject a combination therapy which comprises avelumab and axitinib, wherein avelumab is administered about once every two weeks, and axitinib is administered twice daily.

15. The method of claim 14, wherein avelumab is administered at a dose of about 10 mg/kg.

16. The method of claim 14, wherein axitinib is administered at a dose of 5 mg.

17. The method of claim 14, wherein avelumab is administered at a dose of about 10 mg/kg, and axitinib is administered at a dose of 5 mg.

18. The method of claim 14, wherein avelumab is administered as a 1-hour intravenous infusion.

19. The method of claim 14, wherein the administration of avelumab and axitinib is discontinued if unacceptable toxicity occurs.

20. The method of claim 14, wherein the administration of avelumab and axitinib is discontinued if disease progression occurs.

21. A method for treating renal cell carcinoma in a human subject comprising administering to the subject a combination therapy which comprises avelumab and axitinib, wherein avelumab is administered about once every two weeks as a 1-hour intravenous infusion.

22. The method of claim 21, wherein avelumab is administered at a dose of about 10 mg/kg.

23. The method of claim 21, wherein axitinib is administered twice daily.

24. The method of claim 23, wherein axitinib is administered at a dose of 5 mg.

\* \* \* \* \*

UNITED STATES PATENT AND TRADEMARK OFFICE
CERTIFICATE OF CORRECTION

| | | |
|---|---|---|
| PATENT NO. | : 10,869,924 B2 | Page 1 of 1 |
| APPLICATION NO. | : 15/736615 | |
| DATED | : December 22, 2020 | |
| INVENTOR(S) | : Andrews et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 211 days.

Signed and Sealed this
Tenth Day of May, 2022

Katherine Kelly Vidal
*Director of the United States Patent and Trademark Office*